(12) United States Patent
Quirion et al.

(10) Patent No.: US 8,394,362 B2
(45) Date of Patent: Mar. 12, 2013

(54) GEM DIFLUORINATED C-GLYCOPEPTIDES, THEIR PREPARATION AND THEIR USE FOR THE PRESERVATION OF BIOLOGICAL MATERIALS AND/OR IN CRYOSUGERY

(75) Inventors: Jean-Charles Quirion, Bourg Achard (FR); Géraldine Castelot-Deliencourt-Godefroy, Rouen (FR)

(73) Assignee: Institut National des Sciences Appliquees de Rouen (INSA), Cedex (FR)

(*) Notice: Subject to any disclaimer, the term of this patent is extended or adjusted under 35 U.S.C. 154(b) by 919 days.

(21) Appl. No.: 11/720,670

(22) PCT Filed: Dec. 2, 2005

(86) PCT No.: PCT/IB2005/003940
§ 371 (c)(1), (2), (4) Date: Sep. 17, 2009

(87) PCT Pub. No.: WO2006/059227
PCT Pub. Date: Jun. 8, 2006

(65) Prior Publication Data
US 2010/0041584 A1    Feb. 18, 2010

(30) Foreign Application Priority Data
Dec. 2, 2004  (FR) .................................... 04 12782

(51) Int. Cl.
*A01N 1/02*   (2006.01)
*A61K 8/64*   (2006.01)
*A61K 38/14*  (2006.01)
*C07K 9/00*   (2006.01)

(52) U.S. Cl. ........... 424/78.02; 435/1.1; 435/1.3; 435/2; 514/18.8; 514/20.9; 530/322

(58) Field of Classification Search .................. None
See application file for complete search history.

(56) References Cited

U.S. PATENT DOCUMENTS
2006/0142206 A1 * 6/2006 Quirion et al. ............... 514/23
2007/0031516 A1 * 2/2007 Garcia Anton et al. ....... 424/725

FOREIGN PATENT DOCUMENTS
WO   WO 2004/014928 A2 *  2/2004
WO   WO 2004/087191 A1 * 10/2004

*Primary Examiner* — Jeffrey E Russel
(74) *Attorney, Agent, or Firm* — Browdy and Neimark, PLLC

(57) ABSTRACT

The invention concerns a gem-difluorinated C-glycopeptide compound of formula (I)

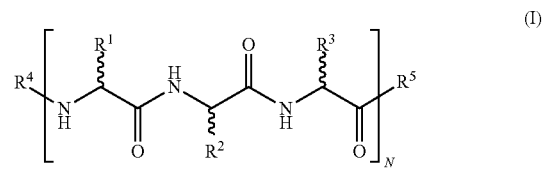

in which N is an integer between 1 and 5, $R^4$=H, $AA_1$, $AA_1$-$AA_2$ and $R^5$=OH, $AA_1$, $AA_1$, $AA_2$, with $AA_1$, and $AA_2$ are independents groups and represent amino acids with a non-functionalized side chain and $R^1$, $R^2$, $R^3$ are independent groups and one of them is equal to formula (II), in which n is an integer between 3 and 4, Y, Y' are independent groups in which Y, Y'=H, OR, $N_3$, NR'R'', SR''', where R=H, benzyl, trimethylsilyl, tert-butyldimethylsilyl, tert-butyldiphenylsilyl, acetate group, R', R'''=H, alkyl, allyl, benzyl, tosylate group, C(=O)-alkyl, C(=O)-Bn, R'''=H, alkyl, acetate group, $R^6$ is notably a group H, $CH_3$, $CH_2OH$, $CH_2$-Glycoside group, $CH_2$-OGP in which GP is a protector group such as an alkyl, benzyl, trimethylsilyl, tert-butyldimethylsilyl, tertbutyldiphenylsilyl, acetate group,; and $R^7$=OH, OGP', $NH_2$, $N_3$, NHGP', NGP'GP'' in which GP' and GP''' is or not a protector group such as an alkyl, benzyl, trimethylsilyl, tert-butyldimethylsilyl, tert-butyldiphenylsilyl, acetate group, and $R^B$ is a hydrogen atom H or a free or protected alcohol function. It applies notably to preservation of biological materials and to cryosurgery.

16 Claims, 30 Drawing Sheets

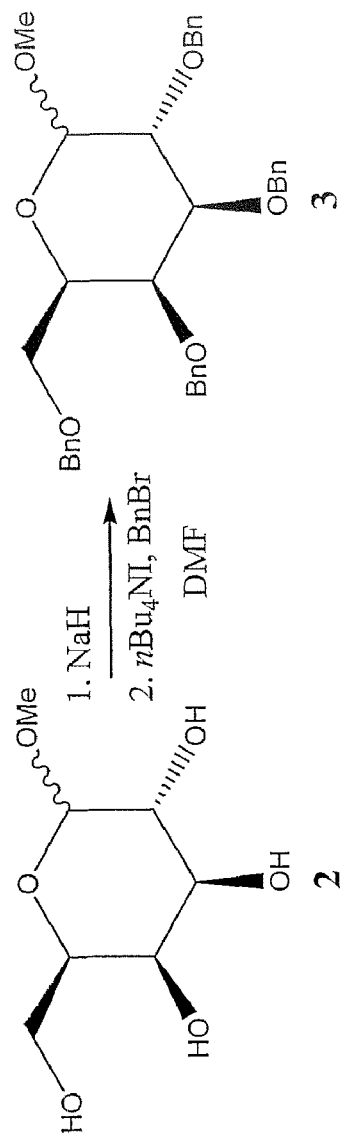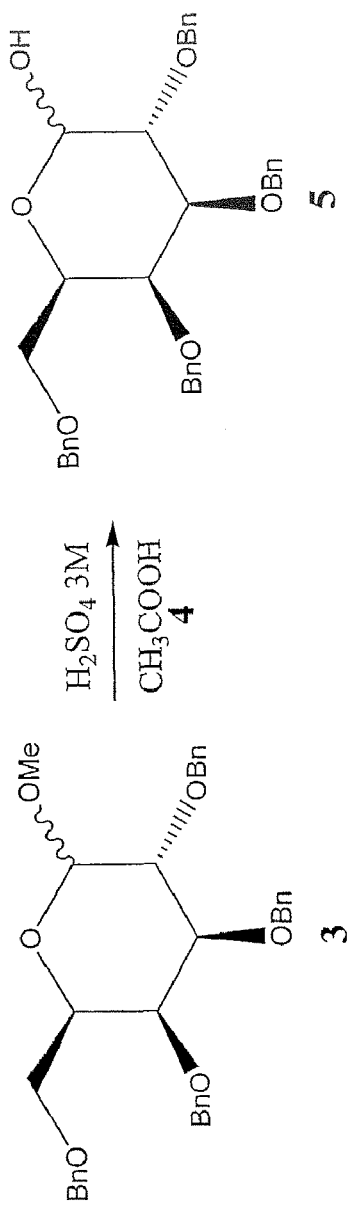

Control Compound 15

GEM DIFLUORINATED C-GLYCOPEPTIDES, THEIR PREPARATION AND THEIR USE FOR THE PRESERVATION OF BIOLOGICAL MATERIALS AND/OR IN CRYOSUGERY

BACKGROUND OF THE INVENTION

1. Field of The Invention

The invention concerns a method for synthesizing gem-difluorinated C-glycopeptide compounds. It applies in particular, but not exclusively, to the preparation of compounds or compositions usable notably in the preservation of biological materials and in cryosurgery.

2. Description of The Prior Art

Antifreeze biological compounds exist in the natural environment, glycoproteins in particular. These are compounds present for example in some fishes, enabling them to survive in a low-temperature environment, i.e. near zero or sub-zero temperatures.

Also, it is known that when water freezes, this phenomenon is accompanied by a volume increase due to the three-dimensional growth of ice.

This increase, and resulting osmosis, cause serious damage in living tissues: cell membranes are ruptured, blood ceases to flow and cell microstructures are disturbed.

For many years, scientists have been investigating how antifreeze compounds taken from the natural environment (fish, amphibians, plants, insects . . . ) have an influence on these phenomena, these compounds being notably proteins and glycoproteins.

Intensive research is focusing on the synthesis of similar compounds that are sufficiently stable and whose activity is at least equal to or even greater than the activity of the natural molecules, for commercial applications.

Due to the presence of an osidic bond (bond involving oxygen said to be in an anomeric position) glycoproteins are fragile relatively to several enzymatic systems, including glycosidase enzymes, and are also sensitive to acid-base hydrolysis making their synthesis more difficult.

It is therefore of interest, in order to allow these compounds to maintain their biological properties, to replace the oxygen in the osidic bond so that this bond is no longer deteriorated by an enzymatic process.

Analogs, in which oxygen is replaced by a $CH_2$ group, have been synthesized, but despite an increase in stability and a steric hindrance similar to that of oxygen, the $CH_2$ group has not always proved to be a good mimic of osidic oxygen. Consequently, the biological properties of the initial compound are not always found.

Other classes of compounds in which oxygen is replaced by a nitrogen or sulphur and more recently by a difluoromethylene group are being researched with a view to imparting increased stability to glycoconjugate compounds in a biological medium.

The $CF_2$ group shows particular resistance to processes of biochemical degradation and therefore allows the synthesis of non-hydrolysable structures.

This $O/CF_2$ transposition seems to be especially well adapted to mimicking oxygen at electronic level; the two fluorine atoms acting as the two oxygen-free doublets.

Said compounds could possibly be used for numerous applications such as the preservation of cells, blood platelets, tissues, organs, or for cryosurgery.

There exists a strong demand for an improvement in the storage and preservation of irreplaceable living cells, including sperm, ovules and embryos so that they undergo much less damage than with methods currently used.

The term preservation generally includes preservation at different temperatures, including cryopreservation down to temperatures as low as −196° C.

Therefore, compounds used as adjuvants for preservation and having good stability could be useful for preserving biological materials, notably:

for storing whole human organs such as kidneys, hearts and livers to be transplanted under no time constraints, for preserving delicate tissues with minimum damage and for a sufficiently long period to allow optionally international distribution, for preserving blood platelets and cells, for protecting certain organisms, bacteria, viruses or vaccines.

Cryosurgery, also called cryotherapy, is the use of extreme cold produced by liquid nitrogen (or argon gas) to destroy abnormal tissues.

It is used to treat external tumours such as skin tumours but is also used to treat tumours inside the body, notably in the prostate and liver. Researchers have tested cryosurgery as a treatment for a certain number of cancers including breast cancer, colon and kidney cancers.

In addition, some studies have reported that at a certain concentration (5-10 mg/ml), antifreeze glycoproteins and proteins produce spicule-shaped ice crystals which increase the probability of cell rupture and death during freezing. This property of ice crystals modified by antifreeze glycoproteins and proteins finds applications of high interest in the treatment of some cancers, if they are used in conjunction with cryosurgery.

OBJECT OF THE INVENTION

On this basis, the object of the invention is to solve the above-cited drawbacks.

SUMMARY OF THE INVENTION

For this purpose, it proposes a gem-difluorinated C-glycopeptide having the general formula I:

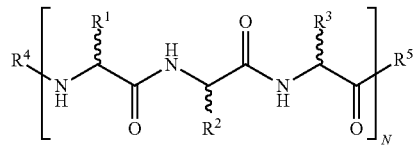

in which:

N is an integer between 1 and 5, $R^4$=H, $AA_1$, $AA_1$-$AA_2$, $R^5$=OH, $AA_1$, $AA_1$-$AA_2$, $AA_1$ and $AA_2$ are independents and representing amino acids with a non-functionalised side chain and $R^1$, $R^2$, $R^3$ are independent groups and if $R^1$=$R^2$=H, $CH_3$, $CH_2Ph$, $CH(CH_3)_2$, $CH_2CH(CH_3)_2$, $CH(CH_3)CH_2CH_3$ then R³=

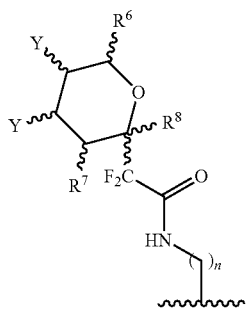

in which: n is an integer between 3 and 4,
Y, Y' are independent groups
in which Y, Y'=H, OR, N₃, NR'R", SR''' . . .
where R=H, Bn, Ac, TMS, TBDMS, TBDPS, . . . ,
R', R"=H, alkyl, allyl, Bn, tosylate (Ts), C(=O)-alkyl, C(=O)-Bn, . . . ,
R'''=H, alkyl, Ac,
R⁶ is notably a group H, CH₃, CH₂OH, CH₂-Glycoside group, CH₂—OGP in which GP is a protector group such as an alkyl, benzyl (Bn), trimethylsilyl (TMS), tert-butyldimethylsilyl (TBDMS), tert-butyldiphenylsilyl (TBDPS), acetate (Ac) group,
R⁷=OH, OGP', NH₂, N₃, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group,
R⁸ is a hydrogen atom H or a free or protected alcohol function,
if R¹=R³=H, CH₃, CH₂Ph, CH(CH₃)₂, CH₂CH(CH₃)₂, CH(CH₃)CH₂CH₃
then R²=

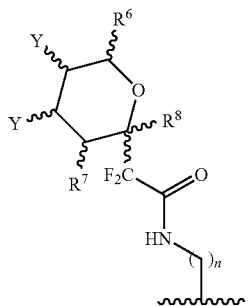

in which: n is an integer between 3 and 4,
Y, Y' are independent groups
in which: Y, Y'=H, OR, N₃, NR'R", SR''' . . .
where R=H, Bn, Ac, TMS, TBDMS, TBDPS, . . . ,
R', R"=H, alkyl, allyl, Bn, tosylate (Ts), C(=O)-alkyl, C(=O)-Bn, . . . ,
R'''=H, alkyl, Ac,
R⁶ is notably a group H, CH₃, CH₂OH, CH₂-Glycoside group, CH₂—OGP group in which GP is a protector group such as an alkyl, benzyl (Bn), trimethylsilyl (TMS), tert-butyldimethylsilyl (TBDMS), tert-butyldiphenylsilyl (TBDPS), acetate (Ac) group,
R⁷=OH, OGP', NH₂, N₃, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group,
R⁸ is a hydrogen atom H or a free or protected alcohol function,
if R²=R³=H, CH₃, CH(CH₃)₂, CH₂CH(CH₃)₂, CH(CH₃)CH₂CH₃
then R¹=

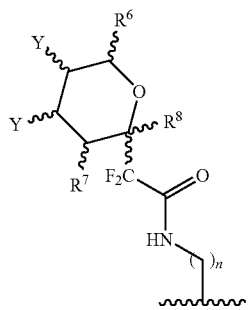

in which: n is an integer between 3 and 4,
Y, Y' are independent groups
in which Y, Y'=H, OR, N₃, NR'R", SR''' . . .
where R=H, Bn, Ac, TMS, TBDMS, TBDPS, . . . ,
R', R"=H, alkyl, allyl, Bn, tosylate (Ts), C(=O)-alkyl, C(=O)-Bn, . . . ,
R'''=H, alkyl, Ac,
R⁶ is notably a group H, CH₃, CH₂OH, CH₂-Glycoside group, CH₂—OGP in which GP is a protector group such as an alkyl, benzyl (Bn), trimethylsilyl (TMS), tert-butyldimethylsilyl (TBDMS), tert-butyldiphenylsilyl (TBDPS), acetate (Ac) group,
R⁷=OH, OGP', NH₂, N₃, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group,
R⁸ is a hydrogen atom H or a free or protected alcohol function.

In the R⁴ and R⁵ functional groups, the amino acids AA₁ and AA₂ are amino acids with a non-functionalised side chain, i.e. non-polar such as Glycine, Alanine, Valine, Leucine, Isoleucine, Phenylalanine . . . .

In the R⁶ functional group, the glycoside may be any sugar such as glucose, galactose, mannose, . . . .

According to one variant, a gem-difluorinated C-glycopeptide compound of the invention may be of formula II:

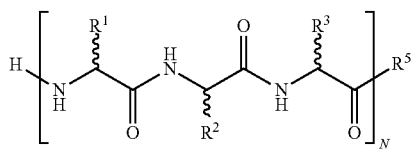

in which: N is an integer between 1 and 5,
and
R¹, R², R³ are independent groups
and
if R¹=R²=H, CH₃, then R³=

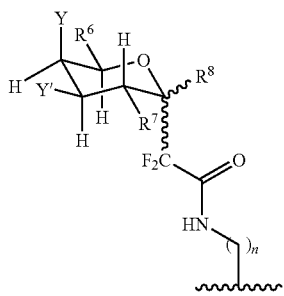

in which: n is an integer between 3 and 4,
  Y, Y' are independent groups
    In which Y, Y'=H, OR, N₃, NR'R", SR"' . . .
      where R=H, Bn, Ac, TMS, TBDMS, TBDPS, . . . ,
      R', R"=H, alkyl, allyl, Bn, tosylate (Ts), C(=O)-alkyl, C(=O)-Bn, . . . ,
      R"'=H, alkyl, Ac,
  R⁶ is notably a group H, CH₃, CH₂OH, CH₂—OGP in which GP is a protector group such as an alkyl, benzyl (Bn), trimethylsilyl (TMS), tert-butyldimethylsilyl (TBDMS), tert-butyldiphenylsilyl (TBDPS), acetate (Ac) group,
  R⁷=OH, OGP', NH₂, N₃, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group,
  R⁸ is a hydrogen atom H or a free or protected alcohol function,
if R¹=R³=H, CH₃,
then R²=

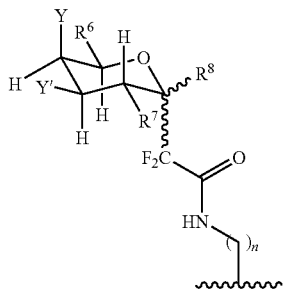

in which: n is an integer between 3 and 4,
  Y, Y' are independent groups
    In which Y, Y'=H, OR, N₃, NR'R", SR"' . . .
      where R=H, Bn, Ac, TMS, TBDMS, TBDPS, . . . ,
      R', R"=H, alkyl, allyl, Bn, tosylate (Ts), C(=O)-alkyl, C(=O)-Bn, . . . ,
      R"'=H, alkyl, Ac,
  R⁶ is notably a group H, CH₃, CH₂OH, CH₂—OGP in which GP is a protector group such as an alkyl, benzyl (Bn), trimethylsilyl (TMS), tert-butyldimethylsilyl (TBDMS), tert-butyldiphenylsilyl (TBDPS), acetate (Ac) group,
  R⁷=OH, OGP', NH₂, N₃, NHGP', NGP'GP" in which GP' and GP" is or not a protector group such as an alkyl, benzyl (Bn), trimethylsilyl (TMS), tert-bu-tyldimethylsilyl (TBDMS), tert-butyldiphenylsilyl (TBDPS), acetate (Ac) group,
  R⁸ is a hydrogen atom H or a free or protected alcohol function,
if R²=R³=H, CH₃,
then R¹=

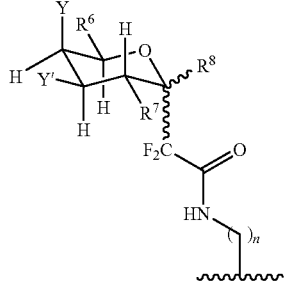

in which: n is an integer between 3 and 4,
  Y, Y' are independent groups
    In which Y, Y'=H, OR, N₃, NR'R", SR"' . . .
      where R=H, Bn, Ac, TMS, TBDMS, TBDPS, . . . ,
      R', R"=H, alkyl, allyl, Bn, tosylate (Ts), C(=O)-alkyl, C(=O)-Bn, . . . ,
      R"'=H, alkyl, Ac,
  R⁶ is notably a group H, CH₃, CH₂OH, CH₂—OGP in which GP is a protector group such as an alkyl, benzyl (Bn), trimethylsilyl (TMS), tert-butyldimethylsilyl (TBDMS), tert-butyldiphenylsilyl (TBDPS), acetate group (Ac),
  R⁷=OH, OGP', NH₂, N₃, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group,
  R⁸ is a hydrogen atom or a free or protected alcohol function.

According to a second variant, the compound may, more precisely, be of general formula III:

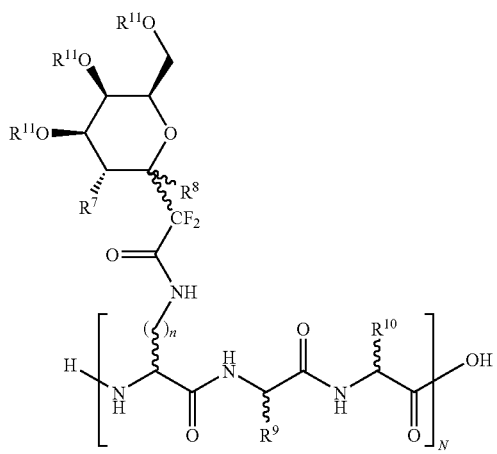

in which:
  N is an integer between 1 and 5,
  n is an integer between 3 and 4,
  R⁷=OH, OGP', NH₂, N₃, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group, $R^8$ is a hydrogen atom or a free or protected alcohol function, $R^9$=H, $CH_3$, $R^{10}$=H, $CH_3$.

$R^{11}$ is a hydrogen atom (H) or a protector group such as an alkyl, benzyl (Bn), trimethylsilyl (TMS), tert-butyldimethylsilyl (TBDMS), tert-butyldiphenylsilyl (TBDPS), acetate (Ac) group.

The compounds of general formulas I-III when in the state of a possible pharmaceutically acceptable base, additive salt to an acid, hydrate or solvate and any derivatives thereof may be produced in different galenic forms suitable for use, for example as solutions or suspensions, optionally injectable.

The compounds of general formulas II and III and some compounds of general formula I may be synthesis intermediates for compounds of general formula I.

Some compositions may contain at least one compound of general formula I, II or II or one of its derivatives or one of its salts obtained by addition to a pharmaceutically acceptable mineral or organic acid.

In addition, this compound of general formula I-III may be prepared by a reaction between a compound with general formula IV:

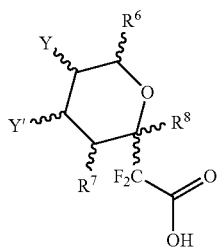

wherein Y, Y' are independent groups
in which Y, Y'=H, OR, $N_3$, NR'R", SR'" ...
where R=H, Bn, Ac, TMS, TBDMS, TBDPS, ...,
R', R"=H, alkyl, allyl, Bn, tosylate (Ts), C(=O)-alkyl, C(=O)-Bn, ...,
R'"=H, alkyl, Ac, $R^6$ is notably a group H, $CH_3$, $CH_2OH$, $CH_2$—OGP in which GP is a protector group such as an alkyl, benzyl (Bn), trimethylsilyl (TMS), tert-butyldimethylsilyl (TBDMS), tert-butyldiphenylsilyl (TBDPS), acetate (Ac), $CH_2$-Glycoside group, $R^7$=OH, OGP', $NH_2$, $N_3$, NHGP', NGP'GP" in which GP' and GP" is or not a protector group such as an alkyl, benzyl (Bn), trimethylsilyl (TMS), tert-butyldimethylsilyl (TBDMS), tert-butyldiphenylsilyl (TBDPS), acetate (Ac) group, $R^8$ is a hydrogen atom H or a free or protected alcohol function, and a compound of general formula V:

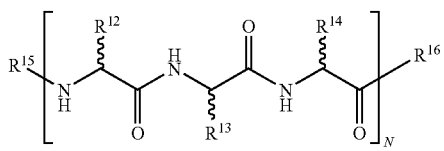

wherein N is an integer between 1 and 5, $R^{15}$=H, $AA_1$, $AA_1$-$AA_2$ or a protective group, $R^{16}$=OH, $AA_1$, $AA_1$-$AA_2$ or a protective group $AA_1$ and $AA_2$ are independent groups and representing amino acids with a non-functionalised side chain, And $R^{12}$, $R^{13}$, $R^{14}$ are independent groups if $R^{12}$=$R^{13}$=H, $CH_3$, $CH_2Ph$, $CH(CH_3)_2$, $CH_2CH(CH_3)_2$, $CH(CH_3)CH_2CH_3$
then $R^{14}$ is —$(CH_2)_n$—$NH_2$ with n is an integer between 3 and 4, if $R^{12}$=$R^{14}$=H, $CH_3$, $CH_2Ph$, $CH(CH_3)_2$, $CH_2CH(CH_3)_2$, $CH(CH_3)CH_2CH_3$
then $R^{13}$ is —$(CH_2)_n$—$NH_2$ with n is an integer between 3 and 4, if $R^{13}$=$R^{14}$=H, $CH_3$, $CH_2Ph$, $CH(CH_3)_2$, $CH_2CH(CH_3)_2$, $CH(CH_3)CH_2CH_3$
then $R^{12}$ is —$(CH_2)_n$—$NH_2$ with n is an integer between 3 and 4.

In addition to pharmaceutically acceptable inert, non-toxic excipients such as distilled water, glucose, starch lactose, talc, vegetable oils, ethylene glycol . . . , the compositions so obtained may also contain preserving agents.

Other active ingredients may be added to these compositions.

The quantity of the compound according the invention and other optional active ingredients in said compositions may vary according to application, the age and weight of the patient when applicable.

BRIEF DESCRIPTION OF THE DRAWINGS

Examples of the preparation of compounds of the invention are described below as non-restrictive examples with reference to the accompanying drawings, in which:

FIG. 1 is a reaction equation to obtain compound 3;
FIG. 2 is a reaction equation to obtain compound 5.

DESCRIPTION OF THE PREFERRED EMBODIMENTS

The abbreviations used are as follows:

| | | | |
|---|---|---|---|
| eq.: equivalent | g: gram | Hz: Hertz | mg: milligram |
| MHz: megaHertz | min.: minute | mL: millilitre | mmol: millimole |
| μmol: micromole | nmol: nanomole | | |

The characteristics of the instruments used to perform the analyses of all the compounds described in the present application are given below:

$^1$H, $^{13}$C, and $^{19}$F NMR spectra were recorded on BRUKER DPX 300 and DPX 600 spectrometers. For $^1$H and $^{13}$C NMR, tetramethylsilane was used as internal reference. For $^{19}$F NMR the external reference was fluorotrichloromethane $CFCl_3$. Chemical shifts are expressed in parts per million (ppm), coupling constants J in Hertz (Hz).

The following abbreviations were used:

s pour singlet, bs for broad singlet, d for doublet, t for triplet, q for quartet, m for multiplet, dd for doublet of doublet . . .

Mass spectra were obtained on a spectrophotometer of the type Micromass TOF-SPEC, E 20 kV, α-cyano. For MALDI ionisation, JEOL AX500, 3 kV, Canon FAB JEOL, Xe, 4 kV, courant limite 10 μA, Gly-NBA 50:50 for FAB ionisation.

Separations by column chromatography were performed under light pressure following chromatography techniques on Kiesel 60 silica gel (230-400 Mesh, Merck).

Follow-up was made by thin-layer chromatography (TLC) using Kieselgel 60F-254-0.25 mm plates. The ratio-to-front (Rf) is the ratio between the migration distance of a compound on a given support and the migration distance of an eluent.

The figures below describe the preparation of gem-difluorinated glycoconjugate compounds having the formula:

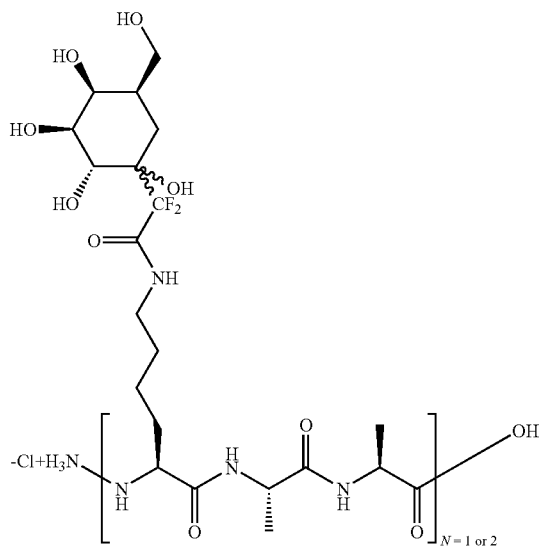

Preparation of Initial Lactone 1

Figure 3:
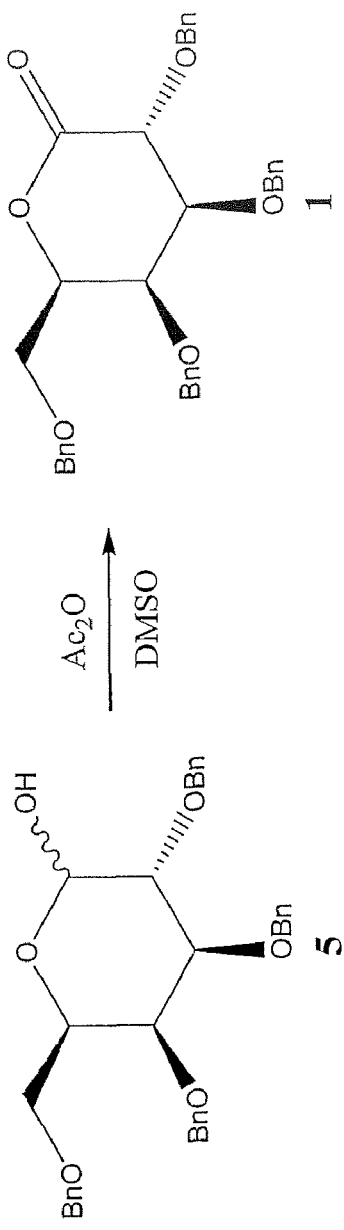
FIG. 3 is a reaction equation to obtain compound 1.

Initially, a lactone 1 is prepared by benzylation of methyl-galactopyrannoside 2 (FIG. 1), deprotection of the anomeric position (FIG. 2), followed by oxidation (FIG. 3):

In a flask under an inert atmosphere containing methyl-D-galactopyranoside 2 (5 g; 26 mmol; 1 eq.) and tetrabutylammonium iodide nBu$_4$NI (500 mg; 1.3 mmol; 0.05 eq.) in dimethylformaldehyde DMF (250 ml), the addition is made of sodium hydride NaH (3.7 g; 0.15 mol; 6 eq.) in small portions. Then benzyl bromide BnBr (18 ml; 0.15 mol; 6 eq.) is added and the mixture is left under stirring for at least 36 hours.

The medium is hydrolysed with water. The aqueous phase is then extracted three times with ether. The organic phases are then collected, washed several times in water, dried over magnesium sulphate, filtered and then evaporated.

The product obtained is purified by chromatography on a column of silica eluting with a cyclohexane/ethyl acetate mixture in a proportion of nine to one. After concentrating the collected fractions, the product 3 is in the form of a white crystals with a weight yield of 95%.

Characterisation of Product 3:

Rf: 0.38 (cyclohexane/ethyl acetate 8/2).

$C_{35}H_{38}O_6$ M=554.67 g.mol$^{-1}$

In a flask containing 1-O-Methyl-2,3,4,6-Tetra-O-Benzyl-D-galactopyranose 3 (5.5 g; 9.92 mmol) in 80 mL acetic acid 4, 11 mL sulphuric acid $H_2SO_4$ are added at a molar concentration of 3M. The reaction medium is heated to 100° C. for one hour. The solution is then diluted in 100 mL cold water.

The mixture is extracted four times with 100 mL toluene. The organic phases are collected, then washed with 100 mL of a saturated solution of sodium hydrogenocarbonate NaHCO$_3$ and finally with 100 mL water. The organic phase is then dried over magnesium sulphate, filtered and concentrated.

The product obtained is purified by silica column chromatography eluting with a cyclohexane/ethyl acetate mixture in the proportion of 8.5 to 1.5. After concentrating the collected fractions, the product 5 is in the form of white crystals with a weight yield of 75%.

Characterization of Product 5:

Rf: 0.65 (cyclohexane/ethyl acetate 6/4).

$C_{34}H_{36}O_6$ M=540.65 g.mol$^{-1}$

In a flask under an inert atmosphere containing 2,3,4,6-Tetra-O-Benzyl-D-Galactopyranose 5 (4 g; 7.4 mmol) the addition is made of dimethylsulphoxide DMSO (25.6 mL) and acetic anhydride Ac$_2$O (16.8 mL). The mixture is left under stirring for 12 hours.

A saturated solution of sodium hydrogenocarbonate NaHCO$_3$ is added, then the aqueous phase is extracted four times with ether. The organic phases are collected then washed five times with water. This organic phase is then dried over magnesium sulphate, filtered and concentrated.

The product is then purified on a silica chromatographic column using as eluent a cyclohexane/ethyl acetate mixture in a proportion of eight to two. After concentrating the collected fractions, the lactone 1 is in the form of a colourless oil with a weight yield of 82%.

Characterization of Product 1:

Rf: 0.61 (cyclohexane/ethyl acetate 8/2).

$C_{34}H_{34}O_6$ M=538.63 g.mol$^{-1}$

NMR $^1$H (CDCl$_3$, 300 MHz)

3.6 (m, 2H, H6); 3.8 (dd, 2.1-9.6, 1H, H3); 4.1 (s, 1H, H4); 4.2 (m, 1H, H5); 4.4-5.1 (m, 9H, H2; 4OC$\underline{H}_2$Bn); 7.2 (m, 20H, H ar.)

NMR $^{13}$C (CDCl$_3$, 75.5 MHz)

67.4 (C6); 72.4 (C5); 72.6 (OCH$_2$Bn); 73.5 (OCH$_2$Bn); 74.5 (C4); 75.1 (OCH$_2$Bn); 77.1 (C2); 79.9 (C3); 127.4-128.3 (Car.); 137.2; 137.3; 137.6 (Car. quat.); 169.8 (CO).

Preparation of a Gem Difluoroester Compound 7

Figure 4:
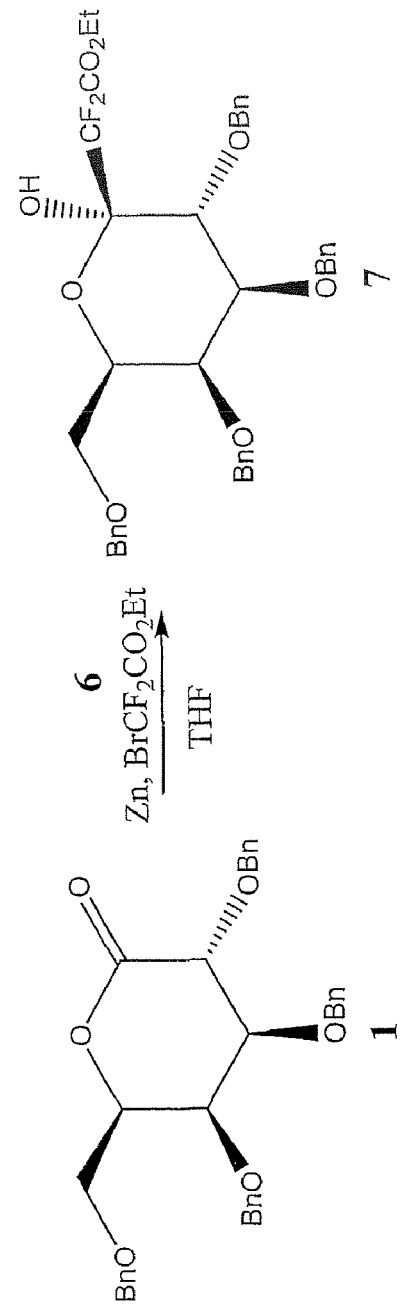
FIG. 4 is a reaction equation to obtain compound 7.

The addition of a bromodifluoroester to the lactone 1 is made using a Reformatsky reaction (FIG. 4).

In a flask, under an inert atmosphere, containing zinc Zn (1.7 g; 26 mmol; 7 eq.) previously activated and scoured, the addition is made of tetrahydrofurane THF (30 mL). The medium is placed under a reflux, then a mixture consisting of lactone 1 (2 g; 3.7 mmol; 1 eq.) and ethyl bromodifluoroacetate 6 (1.42 mL; 11 mmol; 3 eq.) in the THF (30 mL) is added dropwise. The reaction is left under the reflux for 3 hours. On return to ambient temperature, the zinc is filtered; a 1N solution of hydrochloric acid HCl (60 mL) then dichloromethane (6 mL) are added to the reaction medium.

The aqueous and organic phases are separated and the aqueous phase is again extracted two times with dichloromethane. The organic phases are collected, dried over magnesium sulphate, filtered and then concentrated.

The product is subsequently purified on a silica chromatographic column eluting with a cyclohexane/ethyl acetate mixture in a proportion of eight to two. After concentrating the collected fractions, the product 7 is in the form of white crystals with a weight yield of 82%.

Characterization of Product 7:

Rf: 0.35 (cyclohexane/ethyl acetate 8/2).

$C_{38}H_{40}F_2O_8$ M=662.72 g.mol$^{-1}$

NMR $^{19}$F (CDCl$_3$, 282.5 MHz)

−118.4 (d, $J_{F-F}$=256 Hz); −120.2 (d, $J_{F-F}$=256 Hz).

NMR $^1$H (CDCl$_3$, 300 MHz)

1.1 (t, 7.2, 3H, CH$_3$); 3.4-3.5 (m, 2H, H6); 3.7-3.8 (dd, 2.5-9.5, 1H, H3); 3.8 (d, 2, 1H, H4); 4-4.1 (m, 3H, H5; CH$_2$); 4.25-4.85 (m, 9H, H2; 4OCH$_2$Bn); 7.2 (m, 20H, Har).

NMR $^{13}$C (CDCl$_3$, 75.5 MHz)

14.2 (CH$_3$); 63.6 (CH$_2$); 68.6 (C6); 71.7 (C5); 73.2 (OCH$_2$Bn); 73.9 (OCH$_2$Bn); 74.1 (C4); 74.9 (OCH$_2$Bn); 75.1 (C2); 75.8 (OCH$_2$Bn); 81.2 (C3); 96.9 (t, 27 Hz, C1); 113 (t, 264 Hz, CF$_2$); 128.0-128.9 (Car.); 138.2; 138.3; 138.6; 139.1 (Car. quat.); 163.3 (t, 31 Hz, $\underline{C}$O$_2$Et).

Figure 5:
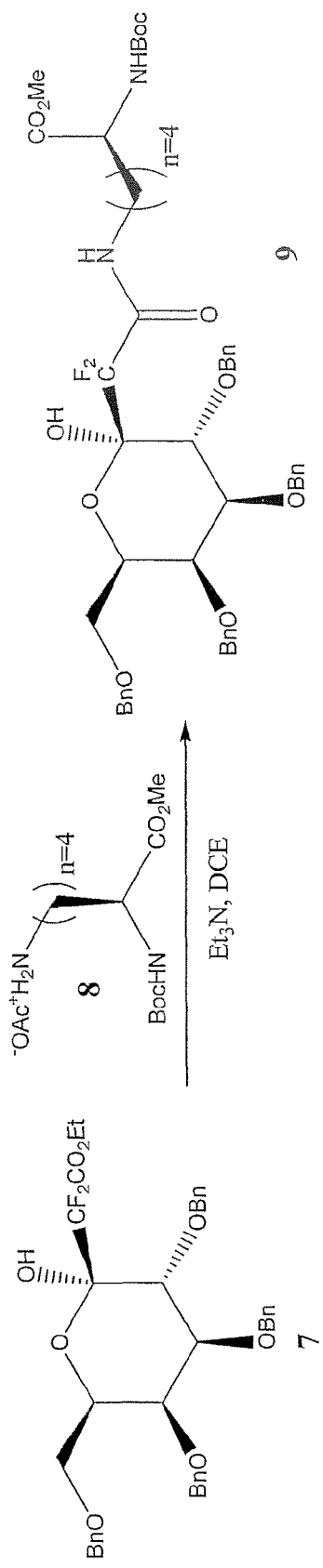
FIG. 5 is a reaction equation to obtain compound 9.
Figure 6:
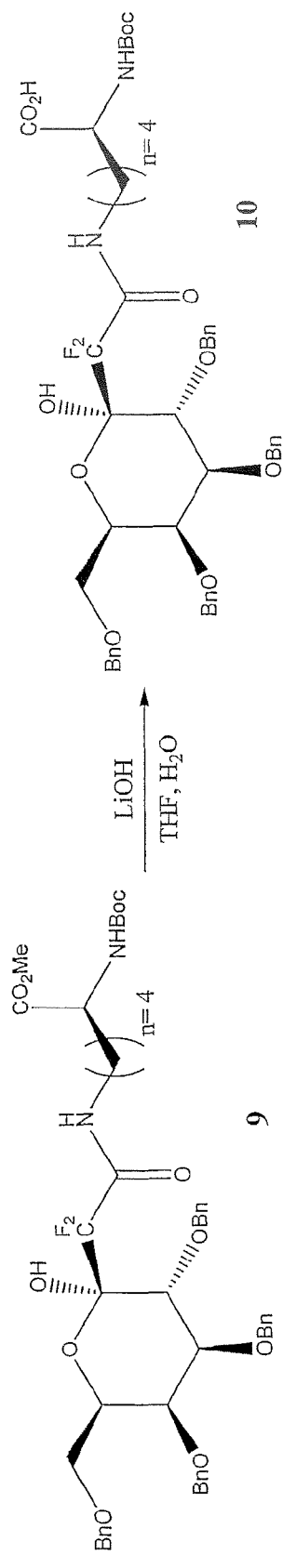
FIG. 6 is a reaction equation to obtain compound 10.
Figure 7:
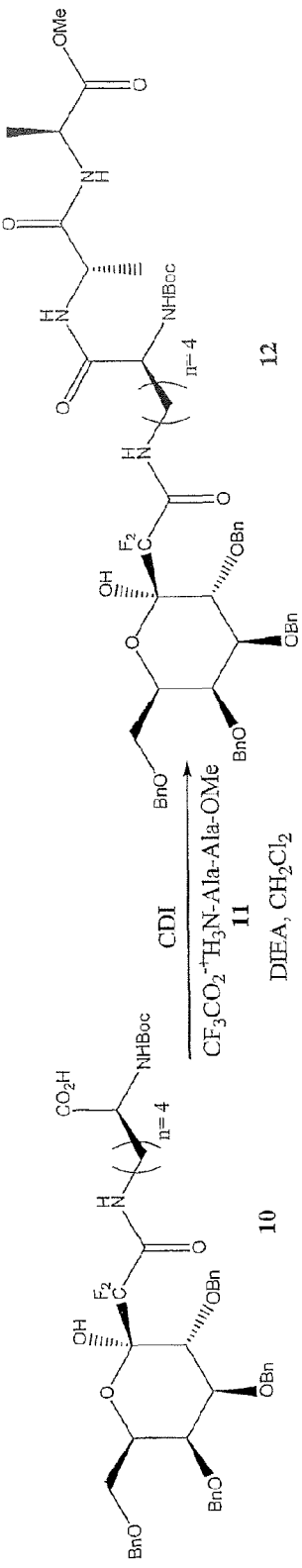
FIG. 7 is a reaction equation to obtain compound 12.

First Access Route For Adding the Peptide Chain:

The addition of the peptide chain may be performed in two different ways. The first was used for the synthesis of a Lysine-Alanine-Alanine monomer. Firstly the first amino acid is added which reacts with the difluoroester function (FIG. 5). After obtaining the first glycoaminoacid, the ester of the lysine is saponified (FIG. 6), then the Alanine-Alanine unit is added via peptide coupling (FIG. 7).

Figure 8:
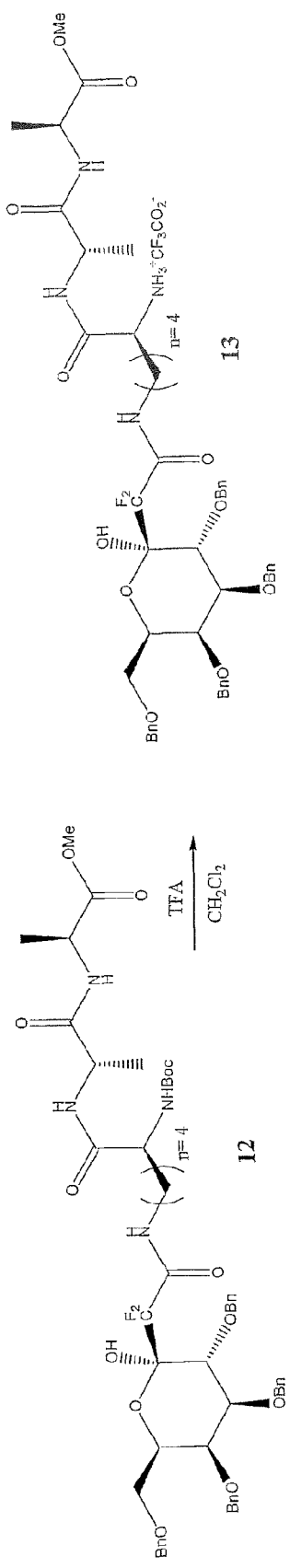
FIG. 8 is a reaction equation to obtain compound 13.
Figure 9:
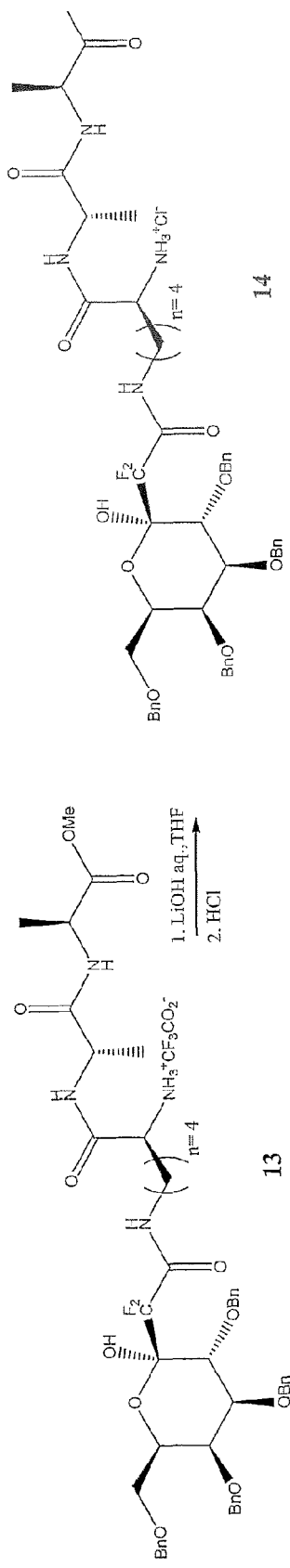
FIG. 9 is a reaction equation to obtain compound 14.
Figure 10:
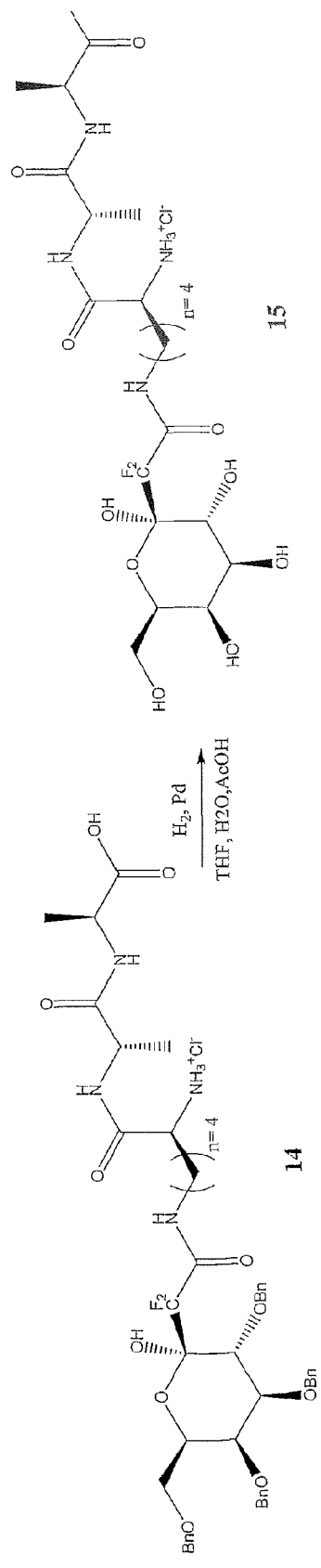
FIG. 10 is a reaction equation to obtain compound 15.

The N then O terminal functions of the monomer so obtained are then deprotected (FIGS. 8 and 9), and finally debenzylation of the galactoside unit is performed (FIG. 10):

A) Addition of the First Aminoacid (FIG. 5):

In a flask, under an inert atmosphere, containing starting product 7 (50 mg; 0.075 mmol; 1 eq.) in solution and the acetate of Boc-lysine-OMe 8 (48 mg; 0.15 mmol; 2 eq.) in dichloroethane (3 mL), the addition is made of triethylamine $Et_3N$ (53 μl; 0.375 mmol; 5 eq.). The mixture is heated under a reflux for 48 hours then hydrolysed with water and extracted three times in dichloromethane. The organic phases are collected, dried over magnesium sulphate, filtered and then concentrated.

The solvent is evaporated then the mixture is purified by chromatography on a silica column using as eluent a cyclohexane/ethyl acetate mixture in the proportion of seven to three. After concentrating the collected fractions, the product 9 is in the form of a white solid with a weight yield of 84%.

Characterization of Product 9:

Rf: 0.58 (cyclohexane/ethyl acetate 7/3).

$C_{48}H_{58}F_2N_2O_{11}$ M=876.98 g.mol$^{-1}$

NMR $^{19}$F (CDCl$_3$, 282.5 MHz)

−117.1 (d, $J_{F-F}$=260 Hz); −121.8 (d, $J_{F-F}$=260 Hz).

NMR $^1$H (CDCl$_3$, 300 MHz)

1.1 (m, 2H, $CH_2$); 1.2-1.5 (m, 2H, $CH_2$); 1.3 (s, 9H, ($CH_3)_3C$); 1.6 (m, 2H, $CH_2$); 3.0-3.1 (m, 2H, $CH_2NH$); 3.4-3.5 (m, 2H, H6); 3.6 (s, 3H, $OCH_3$); 3.8 (m, 2H, H3; H4); 4.1 (m, 2H, CHNH (Lys); H5); 4.2-4.9 (m, 8H, 4$OCH_2Bn$); 4.3 (d, 3.3, 1H, H2); 5 (s, 2H, 2NH); 6.7 (s, 1H, 1NH); 7.2 (m, 20H, H ar.).

NMR $^{13}$C (CDCl$_3$, 75.5 MHz)

22.9 ($CH_2$); 27.3 ($CH_2$); 28.7 (($CH_3)_3C$); 32.4 ($CH_2$); 39.4 ($CH_2N$); 52.7 ($OCH_3$); 53.6 (NCH Lys); 68.7 (C6); 71.1 (C5); 73.4 and 73.7 (2$OCH_2Bn$); 74.5 (C4); 75.0 ($OCH_2Bn$; C2); 75.8 ($OCH_2Bn$); 80.3 (($CH_3)_3C$); 80.9 (C3); 97.1 (t, 28 Hz, C1); 112.8 (t; 260 Hz); 128.0-128.9 (Car.); 138.2; 138.3; 138.7; 139.0 (Car. quat.); 155.9 (CO(Boc)); 164.1 (t, 28 Hz, $CF_2CONH$); 173.6 ($CO_2Et$).

B) Saponification of the Lysine Ester (FIG. 6):

In a flask containing starting product 9 (1.25 g; 1.43 mmol; 1 eq.) in THF (10 mL), the addition is made of lithine LiOH (70 mg; 2.9 mmol; 2 eq.) in solution in water (1 mL) and the mixture is left to react for 24 hours. The reaction medium is then collected in dichloromethane. A 1N solution of hydrochloric acid HCl (5 mL) is added. The aqueous phase is extracted three times in dichloromethane. The organic phases are collected, washed in water (5 mL), dried over magnesium sulphate, filtered and then concentrated. The product 10 obtained is in the form of a white solid with quantitative weight yield.

Characterization of Product 10:

$C_{47}H_{56}F_2N_2O_{11}$ M=862.95 g.mol$^{-1}$

NMR $^{19}$F (CDCl$_3$, 282,5 MHz)

−117.2 (d, $J_{F-F}$=260 Hz); −121.5 (d, $J_{F-F}$=260 Hz).

NMR $^1$H (CDCl$_3$, 300 MHz)

1.2 (m, 2H, $CH_2$); 1.3-1.5 (m, 2H, $CH_2$); 1.3 (s, 9H, ($CH_3)_3C$); 1.6 (m, 2H, $CH_2$); 3.0-3.1 (m, 2H, $CH_2NH$); 3.4-3.5 (m, 2H, H6); 3.8 (m, 2H, H3; H4); 4.1 (m, 2H, CHNH (Lys); H5); 4.2-4.9 (m, 8H, 4$OCH_2Bn$); 4.4 (d, 3.4, 1H, H2); 5.1 (d, 7.5, 1H, NH); 6.6 (s, 1H, NH); 7.2 (m, 20H, Har.).

NMR $^{13}$C (CDCl$_3$, 75.5 MHz) 22.6 ($CH_2$); 27.3 ($CH_2$); 28.7 (($CH_3)_3C$); 32.0 ($CH_2$); 39.4 ($CH_2N$); 53.7 (NCH Lys); 68.7 (C6); 71.1 (C5); 73.4 et 73.7 (2$OCH_2Bn$); 74.4 (C4); 74.9 (C2); 75.0 ($OCH_2Bn$); 75.8 ($OCH_2Bn$); 80.5 (($CH_3)_3C$); 80.9 (C3); 97.0 (t, 28 Hz, C1); 112.8 (t; 260 Hz); 127.9-128.9 (Car.); 138.1; 138.2; 138.6; 139.0 (Car. quat.); 156.2 (CO(Boc)); 164.0 (t, 28 Hz, $CF_2CONH$); 176.7 ($CO_2H$).

C) Addition of an Alanine-Alanine Unit By Peptide Coupling (FIG. 7):

In a flask under an inert atmosphere containing acid 10 (520 mg; 0.6 mmol; 1 eq.) in dichloromethane (15 mL), the addition is made of carbonyldiimadozale CDI (117 mg; 0.72 mmol; 1.2 eq.). The mixture is left under stirring for one hour. Then a solution prepared under an inert atmosphere and consisting, of trifluoroacetate-Alanine-Alanine-OMe 11 (229 mg; 0.79 mmol; 1.3 eq.), of diisopropylethylamine DIEA (347 μL; 1.99 mmol; 3.3 eq.) in dichloromethane (15 mL) is added to this mixture and the reaction medium is left under stirring for 36 hours. The mixture is then hydrolysed with water, followed by extraction three times in dichloromethane. The organic phases are collected, dried over magnesium sulphate, filtered and then concentrated.

The solvent is evaporated then the mixture is purified by chromatography on a silica column using as eluent a cyclohexane/ethyl acetate mixture in a proportion of three to seven. After concentrating the collected fractions, the product 12 is in the form of a white solid with a weight yield of 55%.

Characterization of Product 12:

Rf: 0.46 (ethyl acetate).

$C_{54}H_{68}F_2N_4O_{13}$ M=1019.13 g.mol$^{-1}$

NMR $^{19}$F (CDCl$_3$, 282.5 MHz)

−116.9 (d, $J_{F-F}$=260 Hz); −121.7 (d, $J_{F-F}$=260 Hz).

NMR $^1$H (CDCl$_3$, 300 MHz)

1.2-1.4 (m, 10H, 2$CH_3$; 2$CH_2$); 1.3 (s, 9H, ($CH_3)_3C$); 1.6 (m, 2H, $CH_2$); 3.0-3.2 (m, 2H, $NHCH_2$); 3.4-3.5 (m, 2H, H6); 3.6 (s, 3H, $OCH_3$); 3.8-3.9 (m, 2H, H3; H4); 4.0 (m, 1H, C HNH (Lys)); 4.1 (t, 6.2, 1H, H5); 4.2-4.9 (m, 10H, 4$OCH_2Bn$; 2CH (Ala)); 4.3 (d, ,.3, 1H, H2); 5.3 (d, 6.4, 2H, 2NH); 7 (m, 1H, NH); 7.2 (m, 20H, Har.).

NMR $^{13}$C (CDCl$_3$, 75.5 MHz)

18.3 and 18.6 (2$CH_3$); 22.8 ($CH_2$); 28.7 (($CH_3)_3C$ and $CH_2$); 32.1 ($CH_2$); 39.3 ($C_{H2}N$); 48.5 and 49.2 (2CH Ala); 52.9 ($OCH_3$); 54.8 (NCH Lys); 68.7 (C6); 71.1 (C5); 73.5 and 73.7 (2$OCH_2Bn$); 74.5 (C4); 75.0 ($OCH_2Bn$; C2); 75.7 (O$CH_2Bn$); 80.5 (($CH_3)_3C$); 80.8 (C3); 97.1 (t, 27 Hz, C 1); 127.9-128.9 (Car.); 138.2; 138.3; 138.7; 139.0 (Car. quat.); 156.0 (CO(Boc)); 164.2 (t, 28 Hz, $CF_2CONH$); 172.3 and 172.5 (2CONH); 173.6 ($CO_2Et$).

D) Deprotection of the N Then O Terminal Functions of the Monomer Obtained (FIGS. 8 and 9):

In a flask under an inert atmosphere containing starting product 12 (0.607 mg; 0.6 mmol; 1 eq.) in dichloromethane (10 mL) the addition is made of trifluoroacetic acid TFA (900 μL; 12 mmol; 20 eq.). The mixture is left to react for 12 hours then the reaction medium is concentrated. Four to five co-evaporations with toluene are conducted to obtain product 13 in the form of a colourless oil with quantitative yield.

Characterization of Product 13:

$C_{51}H_{61}F_5N_4O_{13}$ M=1033.04 g.mol$^{-1}$

NMR $^{19}$F (CDCl$_3$, 282.5 MHz)

−75.9; −116.9 (d, $J_{F-F}$=260 Hz); −120.7 (d, $J_{F-F}$=260 Hz).

NMR $^1$H (CDCl$_3$, 300 MHz)

1.2-1.4 (m, 10H, 2$CH_3$; 2$CH_2$); 1.6 (m, 2H, $CH_2$); 3.0 (m, 2H, $NHCH_2$); 3.4 (m, 2H, H6); 3.5 (s, 3H, $OCH_3$); 3.8-3.9 (m,

3H, CHNH (Lys);H3; H4); 4.1 (m, 1H, H5); 4.2-4.9 (m, 11H, 4O$\overline{CH_2}$Bn; 2CH (Ala); $\overline{H}$2); 7.2 (m, 20$\overline{H}$, H ar.).

NMR $^{13}$C (CDCl$_3$, 75.5 MHz)

17.7 et 18.1 (2CH$_3$); 21.9 (CH$_2$); 28.5 (CH$_2$); 31.0 (CH$_2$); 39.1 (CH$_2$N); 48.7 and 50.0 (2$\overline{CH}$ Ala); 52.8 (OCH$_3$); 53.7 (NCH Lys); 68.8 (C6); 71.2 (C5); 73.3 and 73.8 (2OCH$_2$Bn); 74.3 (C4); 75.0 (OCH$_2$Bn); 75.1 (C2); 75.8 (OCH$_2$Bn); 80.9 (C3); 97.1 (t, 27 Hz, C1);127.9-128.9 (Car.); 138.1; 138.3; 138.6; 138.9 (Car. quat.); 162.0 (qdt, 34 Hz, COCF$_3$);164.2 (t, 28 Hz, CF$_2$CONH); 169.4 and 172.7 (2CONH); 173.6 (CO$_2$Et).

In a flask containing starting product 13 (671 mg; 0.65 mmol; 1 eq.) in THF (5 mL) the addition is made of lithine LiOH (47 mg; 1.9 mmol; 3 eq.) in solution in water (1 mL). The mixture is left to react 12 hours then collected in the dichloromethane. A 1N solution of hydrochloric acid HCl (4 mL) is added and the aqueous phase is extracted three times with dichloromethane. The organic phases are collected, washed in water (4 mL) then concentrated.

Four to five co-evaporations with toluene are conducted to remove traces of water and obtain product 14 in the form of a white solid with quantitative yield.

Characterization of Product 14:

$C_{48}H_{59}ClF_2N_4O_H$ M=941.45 g.mol$^{-1}$

NMR $^{19}$F (CD$_3$OD, 282.5 MHz)

−120.4; −120.5.

NMR $^1$H (CD$_3$OD, 300 MHz)

1.2-1.3 (m,12H, 2CH$_3$; 2CH$_2$); 1.6 (m,2H, CH$_2$); 3.0 (m, 2H, NHCH$_2$); 3.1 (m,2H, H6); 3.5 (m, 3H, CHNH (Lys);H3; H4); 3.8-3.9 (m, 1H, H5); 4.2-4.9 (m,11H, 4CH$_2$OBn; 2CH (Ala); H2); 7.2 (m, 20H, H ar.).

NMR $^{13}$C (CD$_3$OD, 75.5 MHz)

17.7 and 18.1 (2CH$_3$); 23.5 (CH$_2$); 29.9 (CH$_2$); 32.7 (CH$_2$); 40.5 (CH$_2$N); 49.7 and 50.0 (2$\overline{CH}$ Ala); 53.7 (NCH Lys); 70.2 (C6); 72.4 (C5); 74.2 and 74.7 (2OCH$_2$Bn); 76.1 and 76.6 (2OCH$_2$Bn); 76.7 (C4and C2); 82.1 (C3); 98.0 (t, 27 Hz, C1) 111.7 (t, 260 Hz; CF$_2$); 129-130.6 (Car.); 139.7;140.1; 140.2; 140.5 (Car. quat.); 165.5 (t, 28 Hz, CF$_2$CONH); 174.0 and 174.5 (CO).

E) Debenzylation of the Galactoside Unit (FIG. 10):

A flask containing starting product 14 (150 mg; 0.16 mmol) in a mixture of acetic acid CH$_3$CO$_2$H (5 mL), tetrahydrofurane THF (1.5 mL) and water (1.5 mL) in the presence of a spatula tip of palladium on charcoal Pd/C is placed under a hydrogen atmosphere. The i mixture left under stirring overnight then filtered through a Millipore® filter. The mixture is then concentrated to obtain product 15 in the form of a white solid with a yield of 70%.

Characterization of Product 15:

$C_{20}H_{35}ClF_2N_4O_{11}$ M=580.96 g.mol$^{-1}$

NMR $^{19}$F (CD$_3$OD, 282.5 MHz)

−120.0 (d, $J_{F-F}$=258 Hz); −121.3 (d, $J_{F-F}$=258 Hz); −121.6 (d, $J_{F-F}$=258 Hz); −123.0 (d, $J_{F-F}$=258 Hz),

NMR $^1$H (CD$_3$OD, 300 MHz) 1.4 (2d, 7.7, 6H, 2C H$_3$);1.3-1.5 (m, 2H, CH$_2$); 1.7 (m, 2H, CH$_2$); 1.9 (m, 2H, C H$_2$); 3.2 (m, 2H, NHCH$_2$); 3.7-3.8 (m, 4H, H6; H5; H3); 4.2 and 4.4 (2m, 2H, H2);3.9 (m, 1H, CHNH (Lys)); 4.3 and 4.5 (2m, 2H, 2CH (Ala)).

NMR$^{13}$C (CD$_3$OD, 75.5 MHz)

18.7 and 18.9 (2CH$_3$); 23.5 (CH$_2$); 30.1 (CH$_2$); 32.8 (CH$_2$); 40.5 (CH$_2$N); 50.9 (2CH Ala); 54.7 (NCH Lys); 64.7 (C6); 72.7 (C5), 76.2, 77.7 (C4 et C2), 82.4 (C3); 100.6 (C1); 115.6 (t, 260 Hz; CF$_2$); 165.5 (CF$_2$CONH); 170.7 and 174.6 (CO).

Mass (FAB+): 545 (M$^+$−Cl)

Second Access Route for the Preparation of the Peptide Chain:

This consists of the saponification of the gem-difluoroester derivative 7 which will subsequently be coupled with different peptides.

Figure 11:
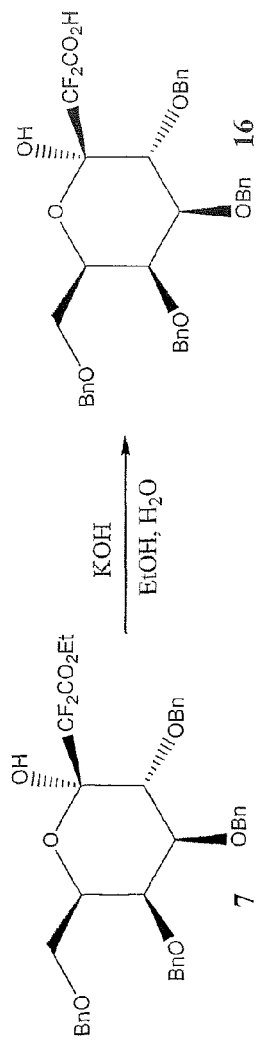
FIG. 11 is a reaction equation to obtain compound 16.

A) Saponification of the Gem-Difluoroester Derivative 7 (FIG. 11)

In a flask containing the ester 7 (0.5 g;1.75 mmol, 1 eq.) in THF (5 mL), the addition is made of an aqueous solution of lithine LiOH (84 mg; 3.5 mmol, 2 eq.) solubilised in a minimum amount of water. The mixture is left under stirring for twelve hours then collected with ethyl acetate. The mixture is acidified with an aqueous 1N solution of hydrochloric acid then extracted several times with ethyl acetate. The organic phases are collected, dried over MgSO$_4$, filtered and concentrated.

Product 16 is obtained in the form of a white oil with quantitative yield.

Characterization of Product 16:

$C_{36}H_{36}F_2O_8$ M=634.66 g.mol$^{-1}$

NMR $^{19}$F (CDCl$_3$, 282.5 MHz)

−117.3 (d, $J_{F-F}$=259 Hz); −119.0 (d, $J_{F-F}$=259 Hz).

NMR $^1$H (CDCl$_3$, 300 MHz) 3.2 (dd, 4.5 Hz and 9.8 Hz,1H, H6); 3.5 (dd, 7.7 Hz and 9.8 Hz,1H, H6); 3.7 (d, 2 Hz, 1H, H4); 3.8 (dd, 2.6 Hz and 9.5 Hz, 1H, H3); 4 (dd, 4.5 Hz and 7.7 Hz;1H, H5); 4.3-4.9 (m, 9H, H2; 4OCH$_2$Bn); 7.2 (m, 20H, Har).

NMR $^{13}$C (CDCl$_3$, 75.5 MHz)

69.4 (C6); 71.7 (C5); 73.5 (OCH$_2$Bn); 74.0 (OCH$_2$Bn); 74.1 (C4); 75.0 (OCH$_2$Bn); 75.1 (C2);75.9 (OCH$_2$Bn); 80.8 (C3); 95.4 (t, 27 Hz, C1); 112.5 (t, 260 Hz, CF$_2$); 127.8-129.0 (Car.); 137.6;138.0; 138.1 (Car. quat.); 163.1 (t, 30 Hz, CO$_2$H).

B) Preparation of the Different Peptides to be Coupled With the Gem-Difluorinated Compound 16.

Figure 12:
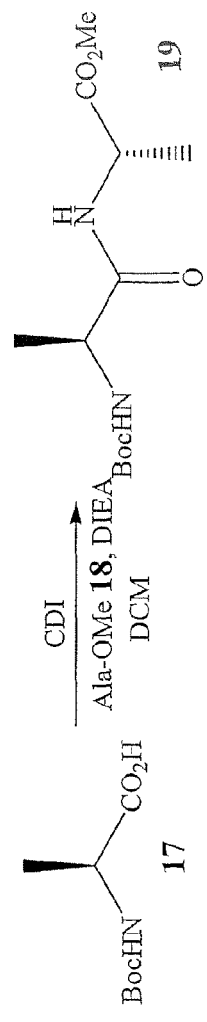
FIG. 12 is a reaction equation to obtain compound 19.

Each of the peptides to be coupled with the gem-difluorinated compound 16 is prepared using a series of deprotection reactions and peptide coupling:

A first coupling between two alanines is performed (FIG. 12):

In a flask under an inert atmosphere containing Boc-Alanine-OH 17 (1 g; 5.29 mmol; 1 eq.) in dichloromethane (25 mL), the addition is made of carbonyldiimadozale CDI (882 mg; 5.44 mmol; 1.03 eq.). The mixture is left under stirring for one hour. To this mixture is added a solution prepared under an inert atmosphere and consisting of Cl$^-$$^+$H$_3$N-Alanine-OMe 18 (738 mg; 5.29 mmol; 1 eq.), and diisopropylethylamine DIEA (1.94 mL; 11.1 mmol; 2.1 eq.) in dichloromethane (15 mL). The mixture is left under stirring for 36 hours then the medium is hydrolysed with water and extracted three times with dichloromethane. The organic phases are collected, dried over magnesium sulphate, filtered and then concentrated.

The solvent is evaporated then the mixture is purified by chromatography on a silica column using as eluent a cyclohexane/ethyl acetate mixture in a proportion of five to five. After concentrating the collected fractions, product 19 is in the form of a white solid with a weight yield of 82%.

Characterization of Product 19:

$C_{12}H_{22}N_2O_5$ M=274.31 g.mol$^{-1}$

NMR $^1$H (CDCl$_3$, 300 MHz)

1.3 (2d, 7.2, 6H, 2CH$_3$); 1.4 (s, 9H, ((CH$_3$)$_3$C); 3.7 (s, 3H, OCH$_3$); 4.2 (m, 1H, CH); 4.6 (m, 1H, CH); 5.2 (d, 7.4, 1H, N H); 6.9 (s, 1H, NH).

NMR $^{13}$C (CDCl$_3$, 75.5 MHz)

18.6 and 18.8 (2CH$_3$); 28.7 ((CH$_3$)$_3$C); 48.3 and 50.2 (2 CH); 52.8 (OCH$_3$); 80.4 ((CH$_3$)$_3$C); 155.8 0 (CO(Boc)); 172.8 and 173.6 (CONH and CO$_2$Et).

Figure 13:
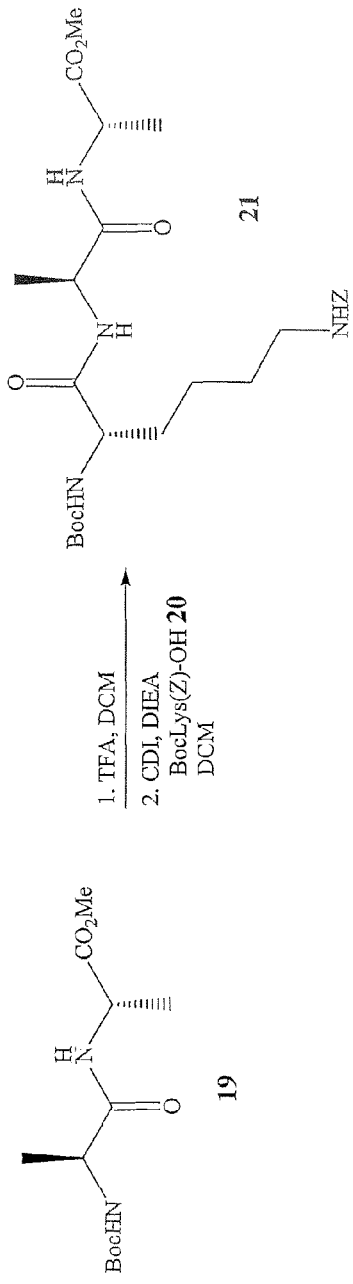
FIG. 13 is a reaction equation to obtain compound 21.

The O-terminal function of the dipeptide 19 obtained is deprotected, then dipeptide 19 is coupled with an N-protected lysine aminoacid (FIG. 13):

1) Deprotection of the Dipeptide Unit

In a flask under an inert atmosphere containing Boc-Alanine-Alanine-OMe 19 (1 g; 3.8 mmol; 1 eq.) in dichloromethane (20 mL), the addition is made of trifluoroacetic acid TFA (5.6 mL; 76 mmol; 20 eq.). Four to five co-evaporations with toluene are performed.

2) Peptide Synthesis

In a flask under an inert atmosphere containing Boc-Lysine (Z)-OH 20 (1.32 g; 3.46 mmol; 1 eq.) in dichloromethane (20 mL), the addition is made of carbonyldiimadozale CDI (560 mg; 3.56 mmol; 1.03 eq.). The mixture is left under stirring for one hour. Then to this product a solution is added prepared under an inert atmosphere and consisting of $CF_3CO_2^{-+}H_3N$-Alanine-Alanine-OMe obtained during the previous reaction (3.8 mmol; 1.1 eq.), and of diisopropylethylamine DIEA (1.26 mL; 7.27 mmol; 2.1 eq.) in dichloromethane (20 mL). The mixture is left under stirring for 36 hours then hydrolysed with water and extracted three times with dichloromethane. The organic phases are collected, dried over magnesium sulphate, filtered and then concentrated.

The solvent is evaporated then the mixture is purified by chromatography on a silica column using ethyl acetate as eluent. After concentrating the collected fractions, product 21 is in the form of a white solid with a weight yield of 66%.

Characterization of Product 21:

$C_{26}H_{40}N_4O_8$ M=536.62 g.mol$^{-1}$

NMR $^1$H (CDCl$_3$, 300 MHz)

1.3 (d, 7.2, 6H, 2CH$_3$); 1.4 (s, 9H, ((CH$_3$)$_3$C) 1.3-1.7(m 6H;3CH$_2$); 3.1 (m, 2H, NHCH$_2$); 3.7 (s, 3H, OCH$_3$); 4.1 (m, 1H, CHLys); 4.6 (m, 2H, CHAla); 5.0 (s, 2H, PhCH$_2$); 5.6 and 5.7 (m, 2H, 2NH); 7.3 (m, 5H, Har.); 7.4 (d, 7Hz, 14Hz, 1H, NH).

NMR $^{13}$C (CDCl$_3$, 75.5 MHz)

18.1 and 18.7 (2CH$_3$); 22.7 (CH$_2$); 28.7 ((CH$_3$)$_3$C); 29.7 (CH$_2$); 32.5 (C$_{H2}$); 40.7 (NCH$_2$); 48.4 and 49.1 (2CH); 52.7 (OCH$_3$); 54.6 (CH Lys); 66.8 (OCH$_2$Bn); 80.2 ((CH$_3$)$_3$C); 128.3-128.8 (Car.); 137.1 (Car. quat.); 156.2 and 157.1 (CO(Boc) and CO(Z)); 172.4, 172.7 and 173.6 (2CONH and CO$_2$Et).

Figure 14:
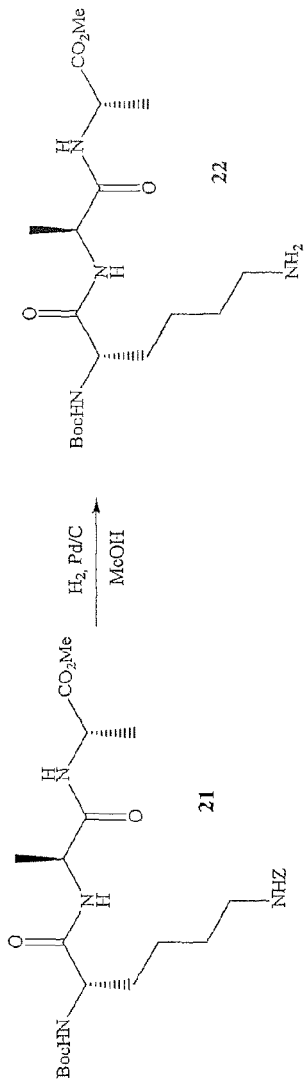
FIG. 14 is a reaction equation to obtain compound 22.

The amino function positioned on the side chain of compound 21 is deprotected by hydrogenation (FIG. 14). Compound 22 obtained may then be directly involved in peptide coupling with product 16 to lead to previously described compound 12 via another synthesis route described below under paragraph C).

A flask containing starting product 21 (1.6 g; 3 mmol) in methanol (20 mL) in the presence of a spatula tip of palladium on charcoal Pd/C is placed under a hydrogen atmosphere. The mixture is left under stirring overnight then filtered through a Millipore filter. The medium is then concentrated. Product 22 is in the form of a white powder with quantitative yield.

Characterization of Product 22:

$C_{18}H_{34}N_4O_6$ M=402.49 g.mol$^{-1}$

RMN $^1$H (CD$_3$OD, 300 MHz)

1.4 (2d, 7.2 Hz, 6H, 2CH$_3$); 1.5 (s, 9H, ((CH$_3$)$_3$C) 1.5-1.8 (m 6H;3CH$_2$); 2.7 (m, 2H, NHCH$_2$); 3.7 (s, 3H, OCH$_3$); 4 (m, 1H, CH Lys); 4,4 (m, 2H, CHAla).

Figure 15:
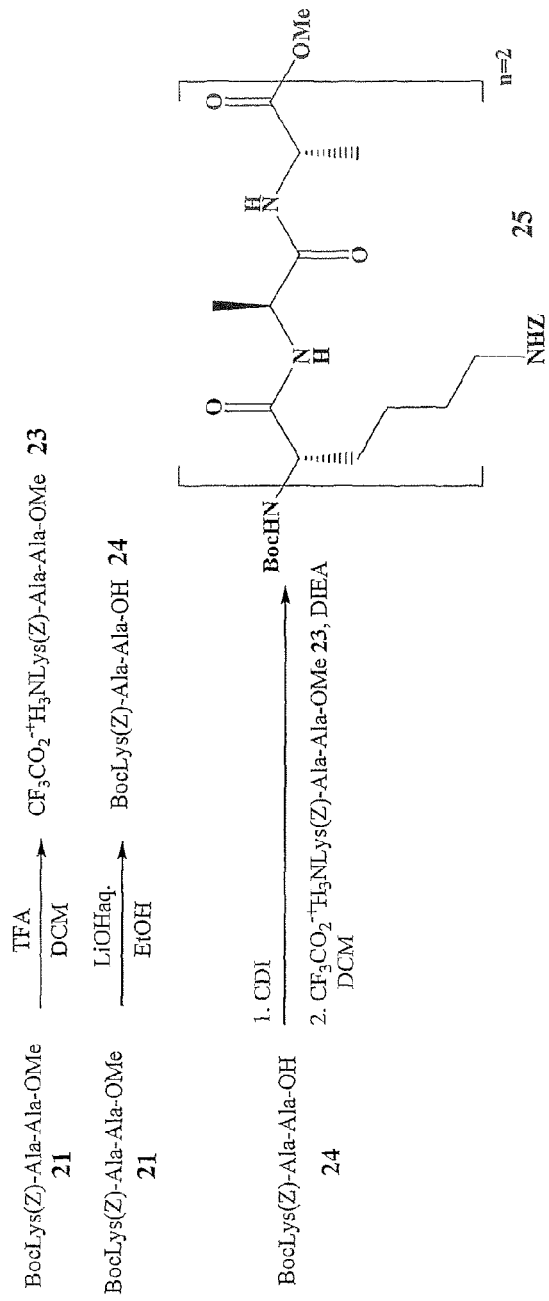
FIG. 15 is a reaction equation to obtain respectively compound 23, 24, 25 (SEQ ID NO:1)

Tripeptide units are deprotected at their N-terminal function (FIG. 15) or O-terminal function (FIG. 15) and peptide synthesis between tripeptide units deprotected at their N-terminal function and tripeptide units deprotected at their O-terminal function is performed. (FIG. 15):

N-deprotection (FIG. 15)

In a flask under an inert atmosphere containing Boc-Lysine (Z)-Alanine-Alanine-OMe 21 (2 g; 3.7 mmol; 1 eq.) in dichloromethane (40 mL), the addition is made of trifluoroacetic acid TFA (5.5 mL; 75 mmol; 20 eq.). The mixture is left to react for 12 hours then concentrated. Four to five co-evaporations with toluene are conducted to obtain $CF_3CO_2^{-+}H_3N$-Lysine(Z)-Alanine-Alanine-OMe 23.

O-deprotection (FIG. 15)

In a flask containing Boc-Lysine(Z)-Alanine-Alanine-OMe 21 (2 g; 3.7 mmol; 1 eq.) in ethanol (45 mL), the addition is made of lithine LiOH (107 mg; 4.5 mmol; 1.2 eq.) in solution in water (2 mL). The mixture is left to react 12 hours. The reaction medium is afterwards evaporated, then collected with the dichloromethane. An aqueous 1N solution of hydrochloric acid HCl (20 mL) is added. The aqueous phase is extracted three times with dichloromethane. The organic phases are collected, dried over magnesium sulphate, filtered then concentrated to obtain Boc-Lys(Z)-Ala-Ala-OH 24.

Peptide synthesis (FIG. 15)

In a flask under an inert atmosphere containing Boc-Lysine (Z)-Alanine-Alanine-OH 24 (3.7 mmol; 1 eq.) in dichloromethane (50 mL), the addition is made of carbonyldiimadozale CDI (665 mg; 4.10 mmol; 1.1 eq.). The mixture is left under stirring for one hour. Then, to this product is added a solution prepared under an inert atmosphere and consisting of $CF_3CO_2^{-+}H_3N$-Lysine(Z)-Alanine-Alanine-Ome 23 (3.7 mmol; 1 eq.), and diisopropylethylamine DIEA (1.62 mL; 9.32 mmol; 2.5 eq.) in the dichloromethane (50 mL). The mixture is left under stirring for 48 hours. The medium is hydrolysed with water, then extracted two times with dichloromethane and two times with chloroform. The organic phases are collected, dried over magnesium sulphate, filtered then concentrated.

The solvent is evaporated and the mixture is purified by chromatography on a silica column eluting with an ethyl/methanol mixture in a proportion of nine to one. After concentrating the collected fractions, product 25 is in the form of a white powder with a weight yield of 56%.

Characterization of Product 25:

$C_{46}H_{68}N_8O_{13}$ M=941.08 g.mol$^{-1}$

NMR $^1$H (DMSO, 300 MHz)

1.3 (m, 12H, 4CH$_3$); 1.4 (s, 9H, ((CH$_3$)$_3$C) 1.3-1.7(m 12H; 6CH$_2$); 3.0 (m, 4H, 2NHCH$_2$); 3.6 (s, 3H, OCH$_3$); 4.1 (m, 1H, CHLys); 4.3 (m, 5H, 5CHAla et Lys); 5.0 (s, 4H, PhCH$_2$); 5.0 (s, 2H, PhCH$_2$); 6.9 (m, 1H, NH); 7.3 (m, 5H, Har.).

NMR $^{13}$C (DMSO, 75.5 MHz)

17.2, 18.3, 18.4 and 18.6 (4CH$_3$); 22.8 and 23.2 (2CH$_2$); 28.5 ((CH$_3$)3C); 29.3 and 29.5 (2CH$_2$); 31.8 and 32.0 (2CH$_2$); 39.5 and 39.8 (2NCH$_2$); 47.8, 43.0, 48.2 and 48.5 (4CHAla); 52.2 (OCH$_3$); 52.6 and 54.6 (2CH Lys); 65.4 (2OCH$_2$Bn); 78.4 ((CH$_3$)$_3$C); 128.0 and 128.6 (Car.); 137.6 (Car. quat.); 155.7 and 156.4 (CO(Boc) and 2 CO(Z)); 171.3, 172.3, 172.4, 172.5 and 173.3 (6CONH and CO$_2$Et).

Figure 16:
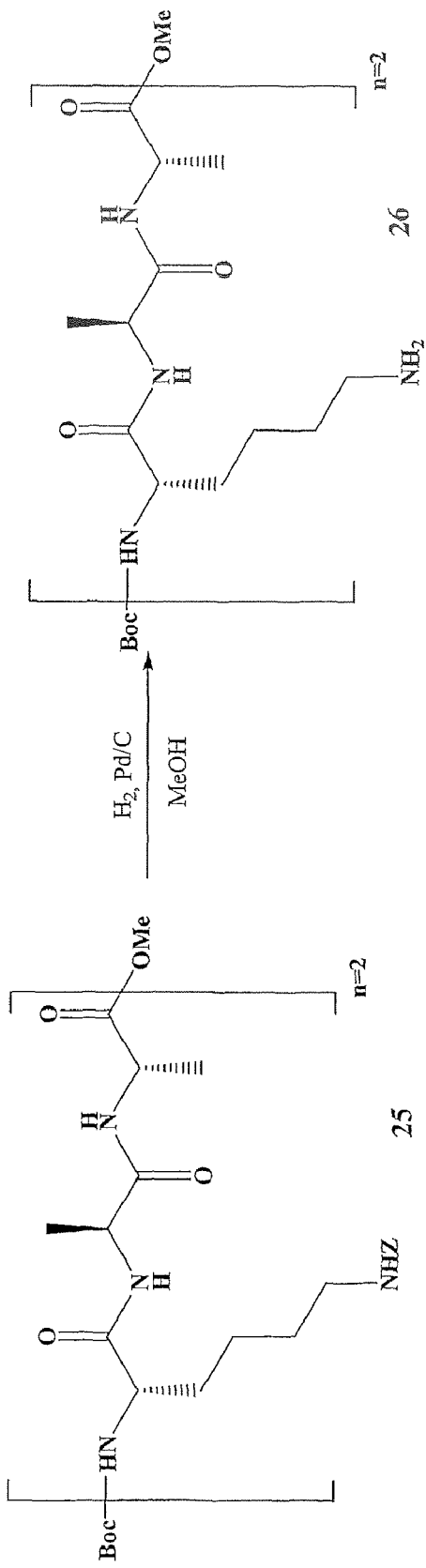
FIG. 16 is a reaction equation to obtain compound 26 (SEQ ID NO:1)

The amino function positioned on the side chain of compound 24 is deprotected by hydrogenation (FIG. 16):

A flask containing starting product 25 (400 mg; 0.43 mmol) in methanol (10 mL) in the presence of a spatula tip of palladium on charcoal Pd/C is placed under a hydrogen atmosphere. The mixture is left under stirring overnight, filtered through a Millipore® filter. The medium is then concentrated. Product 26 is in the form of a white powder with quantitative yield.

Characterization of Product 26:
$C_{30}H_{56}N_8O_9$ M=672.81 g.mol$^{-1}$
NMR $^1$H (DMSO, 300 MHz)
1.2 (m, 12H, 4CH$_3$); 1.4 (s, 9H, ((CH$_3$)$_3$C) 1.3-1.7(m 12H; 6CH$_2$); 2.6 (m, 4H, 2NHCH$_2$); 3.6 (s, 3H, OCH$_3$); 3.8 (m, 1H, CHLys); 4.2 (m, 5H, 5CH Ala and Lys).
Mass (ES+): 696 (M+Na); 674 (M+H)

Figure 17:
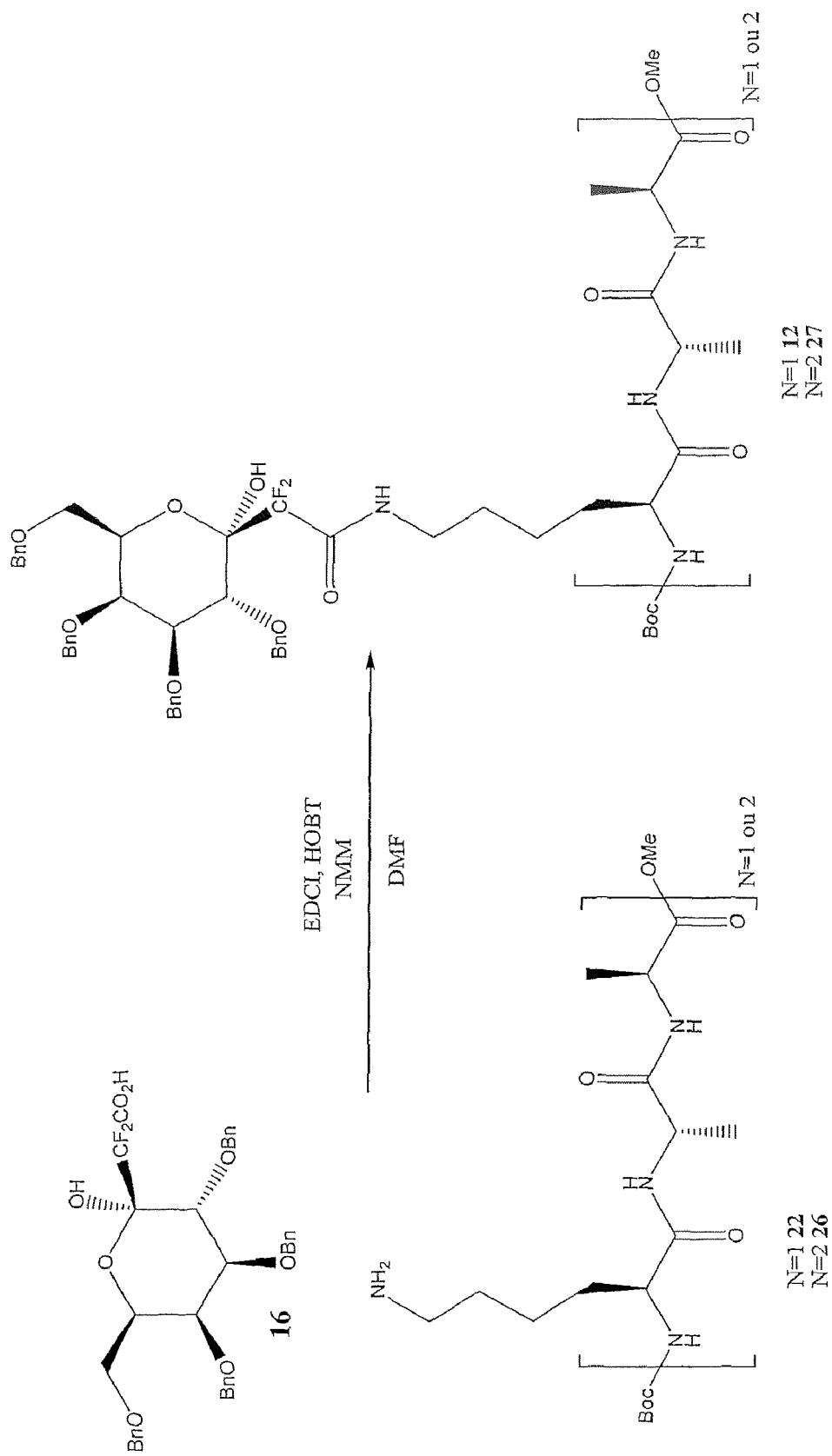
FIG. 17 is a reaction equation to obtain compound 12 or 27 (SEQ ID NO:1)

C) Coupling of the Gem-Difluorinated Compound 16 With Peptide 22 (FIG. 17)

In a flask under an inert atmosphere containing acid 16 (2 g; 3.15 mmol; 1.05 eq.), peptide 22 (1.2 g; 3.0 mmol; 1 eq.), 1-hydroxybenzotriazole HOBT (425 mg; 3.15 mmol; 1.05 eq.) and N-methylmorpholine NMM (346 μL; 3.15 mmol; 1.05 eq.) in DMF (50 mL), the addition is made of EDCI (604 mg; 3.15 mmol; 1.05 eq.). The reaction medium is left under stirring for 48 hours then the solvent is evaporated and the medium collected in a water-dichloromethane mixture. The aqueous phase is extracted three times with dichloromethane. The organic phases are collected, dried on MgSO$_4$, filtered and concentrated.

Product 12 is obtained with a yield of 58%. This product has already been previously characterized.

D) Coupling of the Gem-Difluorinated Compound 16 With Peptide 26 (FIG. 17)

In a flask under an inert atmosphere containing acid 16 (200 mg; 0.32 mmol; 1 eq.), peptide 26 (105 mg; 0.16 mmol; 0.5 eq.), 1-hydroxybenzotriazole HOBT (45 mg; 0.33 mmol; 1.05 eq.) and N-methylmorpholine NMM (32 μL; 0.33 mmol; 1.05 eq.) in DMF (3 mL), the addition is made of EDCI (63 mg; 0.33 mmol; 1.05 eq.). The reaction medium is left under stirring for 48 hours then concentrated. To the medium is added a water-dichloromethane mixture. The aqueous phase is extracted three times with dichloromethane. The organic phases are collected, dried over MgSO$_4$, filtered and concentrated.

Product 27 is obtained in the form of a white powder with a yield of 35%.

Characterization of Product 27:
$C_{102}H_{124}F_4N_8O_{23}$ M=1906.11 g.mol$^{-1}$
$^{19}$F NMR (CDCl$_3$, 282.5 MHz)
−120.4.
$^1$H NMR (CD$_3$OD, 300 MHz)
1.2 (m, 12H, 4CH$_3$); 1.3 (s, 9H, (CH$_3$)$_3$C); 1.3-1.7 (m, 12H, 6CH$_2$); 3.0 (m, 4H, 2NHCH$_2$); 3.4 (m, 4H, H6); 3.6 (s, 3H, OCH$_3$); 3.8 (m, 1H, CHNH (Lys)); 3.9 (m, 4H, H3; H4); 4.0 (m, 2H, H5); 4.1-4.8 (m, 23H, 8OCH$_2$Bn, 4CH (Ala), CHNH (Lys), 2H2); 7.2 (m, 40H, Har.).
$^{13}$C NMR (CD$_3$OD, 75.5 MHz)
16.1, 16.2, 16.3 et 16.7 (4CH$_3$); 22.7 et 22.9 (2CH$_2$); 27.4 et 28.2 ((CH$_3$)$_3$C et 2CH$_2$); 30.8 (2CH$_2$); 38.7 et 39.0 (2 CH$_2$N); 48.1 (OCH$_3$); 48.8, 50.0, 50.1, 51.4, 53.7 et 55.7 (4 CH Ala et 2NCH Lys); 68.2 et 68.5 (2C6); 70.2 et 70.7 (C5); 72.4 (2OCH$_2$Bn); 72.6 (C4); 73.0 (2OCH$_2$Bn); 74.4 (2O CH$_2$Bn); 74.9 (C2); 75.0 (2OCH$_2$Bn); 79.7 ((CH$_3$)$_3$C); 80.3 (C3); 96.2 (t, 27 Hz, C1); 127.3-128.1 (Car.); 138.0-138.9 ( Car. quat.); 157.0 (CO(Boc)); 160.2 (t, 28 Hz, CF$_2$CONH); 172.5, 173.1, 173.2, 174.1 et 174.5 (CONH et CO$_2$Me).
Mass (MALDI+): 1929 (M+Na); 1945 (M+K)

Figure 18:
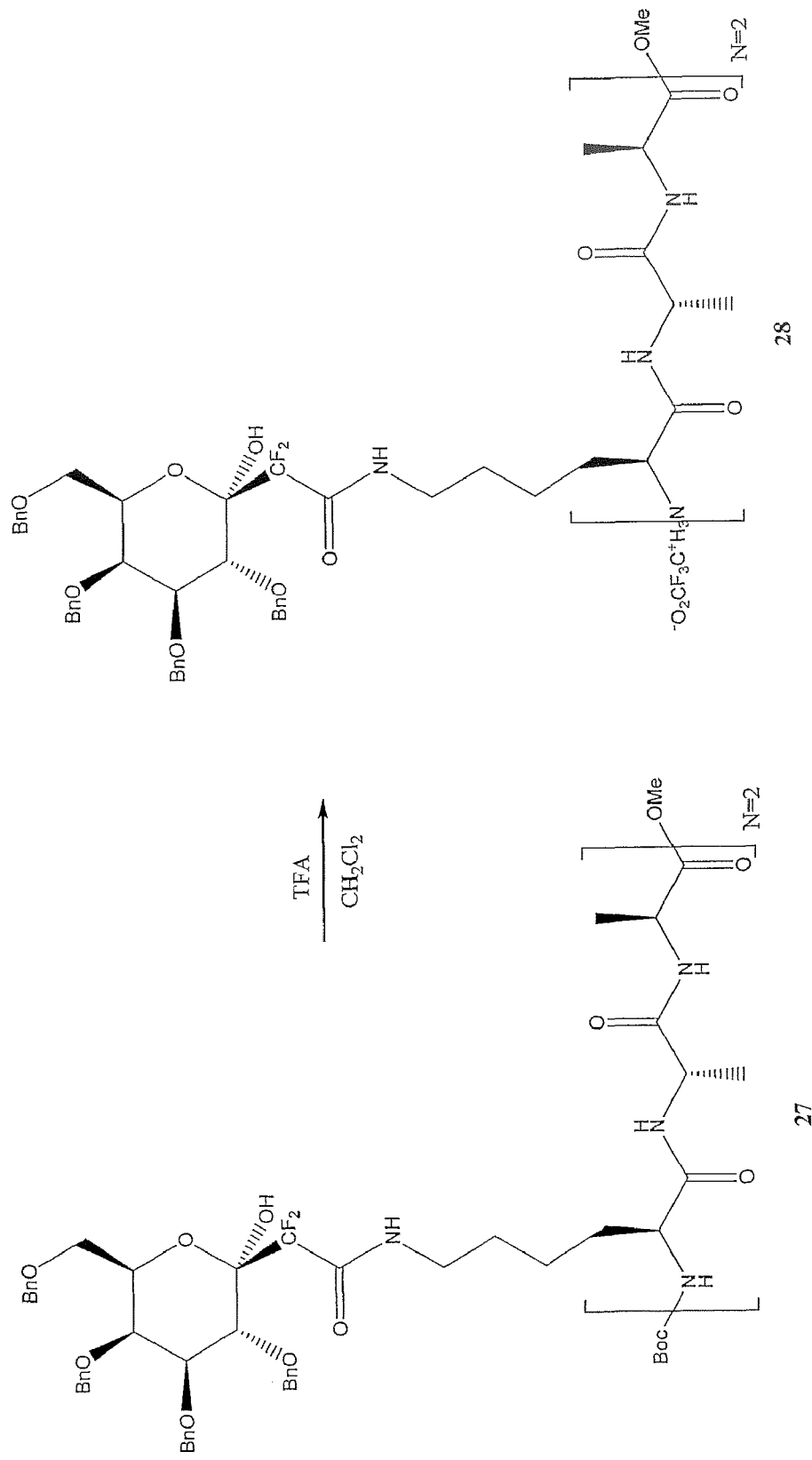
FIG. 18 is a reaction equation to obtain compound 28 (SEQ ID NO:1)
Figure 19:
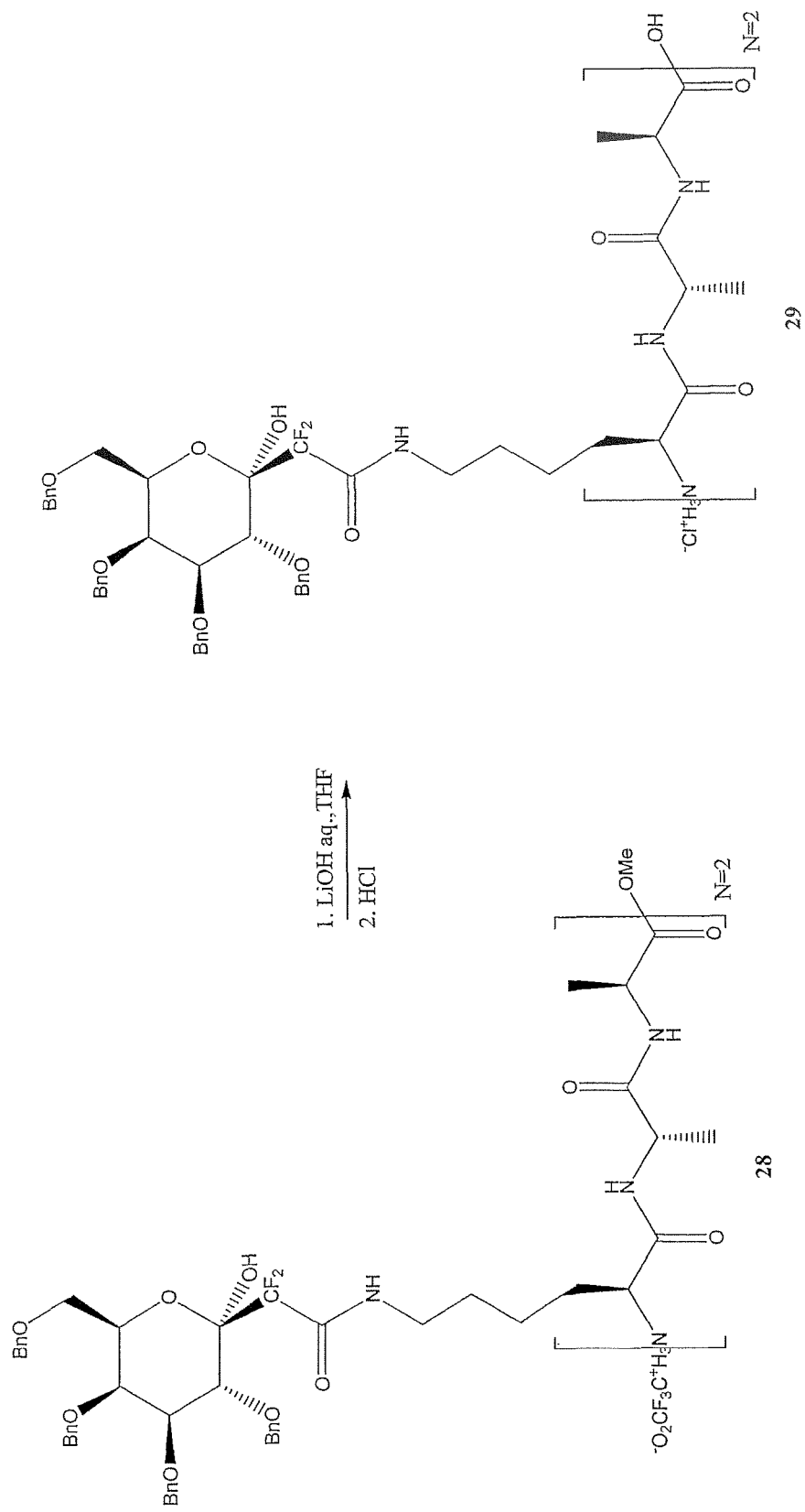
FIG. 19 is a reaction equation to obtain compound 29 (SEQ ID NO:1)

E) Deprotection of the N- Then O-Terminal Functions of the Dimer 27 Obtained (FIGS. 18 and 19):

In a flask under an inert atmosphere containing starting product 27 (107 mg; 0.6 mmol; 1 eq.) in dichloromethane (2 mL) the addition is made of trifluoroacetic acid TFA (89 μL; 1.2 mmol; 20 eq.). The mixture is left to react for 12 hours then the reaction medium is concentrated. Four to five co-evaporations with toluene are performed to obtain product 28 in the form of colourless oil with quantitative yield.

Characterization of Product 28:
$C_{99}H_{117}F_7N_8O_{23}$ M=1920.02 g.mol$^{-1}$
$^{19}$F NMR (CD$_3$OD, 282.5 MHz)
−77.4; −120.2.
$^1$H NMR (CD$_3$OD, 300 MHz)
1.3 (m, 12H, 4CH$_3$); 1.3-1.7 (m, 12H, 6CH$_2$); 3.0 (m, 4H, 2NHCH$_2$); 3.5 (m, 4H, H6); 3.5 (s, 3H, OCH$_3$); 3.7 (m, 1H, C HNH (Lys)); 3.8 (m, 4H, H3; H4); 4.0 (m, 2H, H5); 4.2-4.8 (m, 23H, 8OCH$_2$Bn, 4CH (Ala), CHNH (Lys), 2H2); 7.2 (m, 40H, Har.).

In a flask containing starting product 28 (115 mg; 0.06 mmol; 1 eq.) in THF (2 mL), the addition is made of lithine LiOH (6 mg; 0.24 mmol; 4 eq.) in solution in minimum of water. The mixture is left to react 12 hours then collected in dichloromethane. A 1N solution of hydrochloric acid HCl (4 mL) is added and the aqueous phase is extracted three times with dichloromethane. The organic phases are collected, washed in water (4 mL) then concentrated.

Four to five co-evaporations with toluene are conducted to remove water traces and obtain product 29 in the form of a white solid with a yield of 89%.

Characterization of Product 29:
$C_{96}H_{115}ClF_4N_8O_{21}$ M=1828.43 g.mol$^{-1}$
$^{19}$F NMR (CD$_3$OD, 282.5 MHz)
120
$^1$H NMR (CD$_3$OD, 300 MHz)
1.3 (m, 12H, 4CH$_3$); 1.3-1.7 (m, 12H, 6CH$_2$); 3.0 (m, 4H, 2NHCH$_2$); 3.5 (m, 4H, H6); 3.7 (m, 1H, CHNH (Lys)); 3.9 (m, 4H, H3; H4); 4.1 (m, 2H, H5); 4.2-4.8 (m, 23H, 8OC H$_2$Bn, 4CH (Ala), CHNH (Lys), 2H2); 7.2 (m, 40H, Har.).

Figure 20:
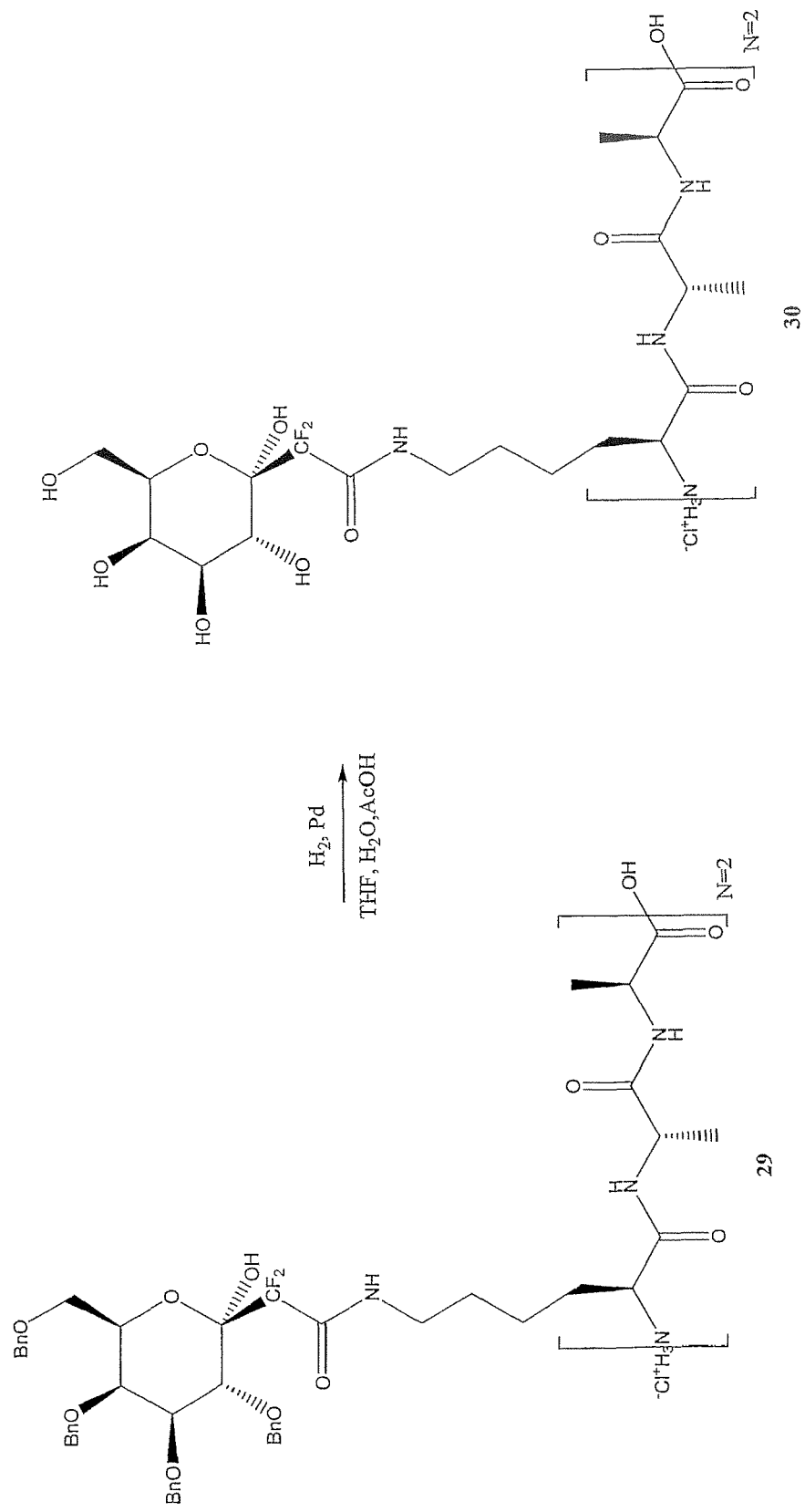
FIG. 20 is a reaction equation to obtain compound 30 (SEQ ID NO:1)
Figure 21:
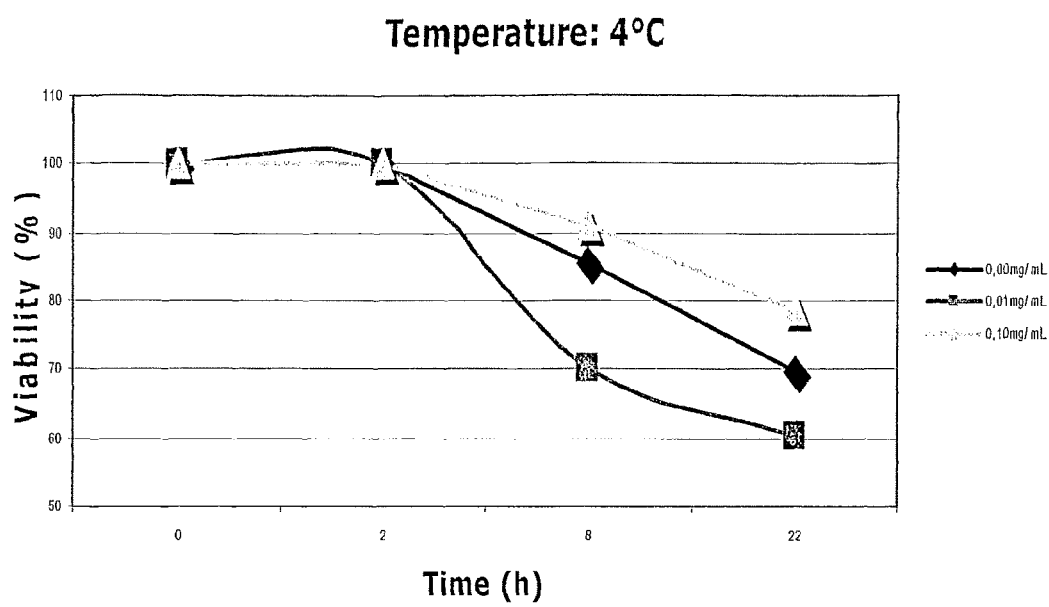
FIG. 21 is a representation of effects of compound 15 on HEK293 viability at 4° C.
Figure 22:
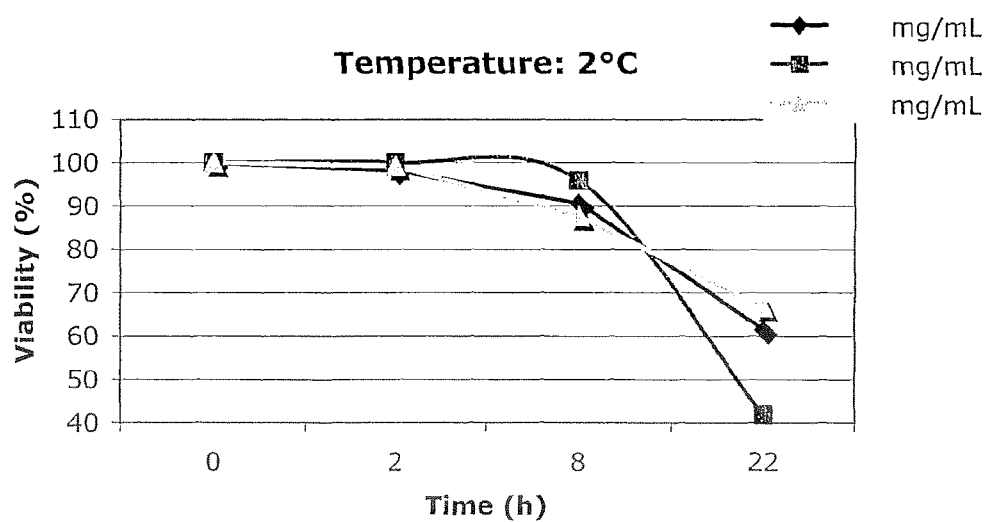
FIG. 22 is a representation of effects of compound 15 on HEK293 viability at 2° C.
Figure 23:
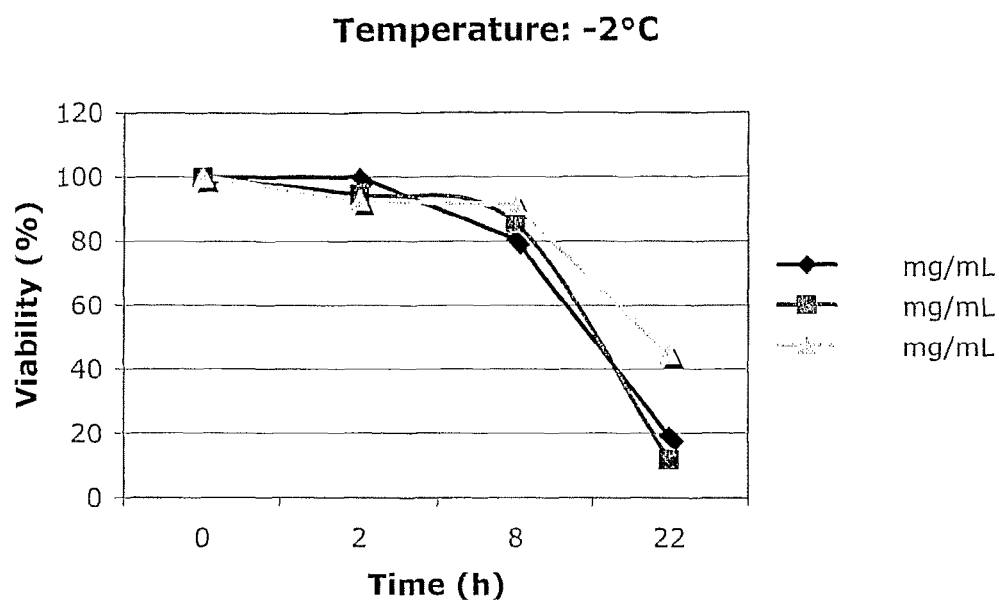
FIG. 23 is a representation of effects of compound 15 on HEK293 viability at 0° C.
Figure 24:
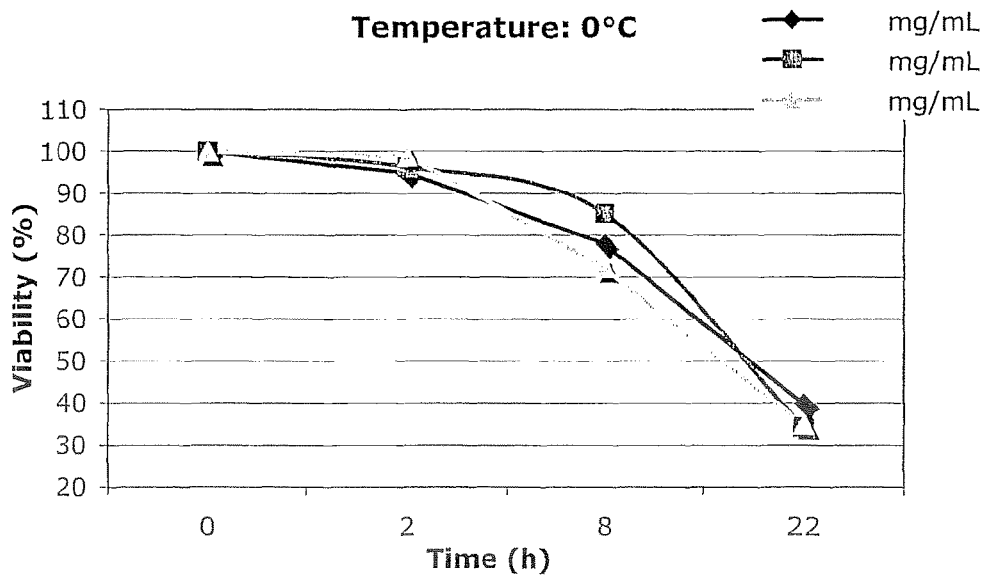
FIG. 24 is a representation of effects of compound 15 on HEK293 viability at −2° C.
Figure 25:
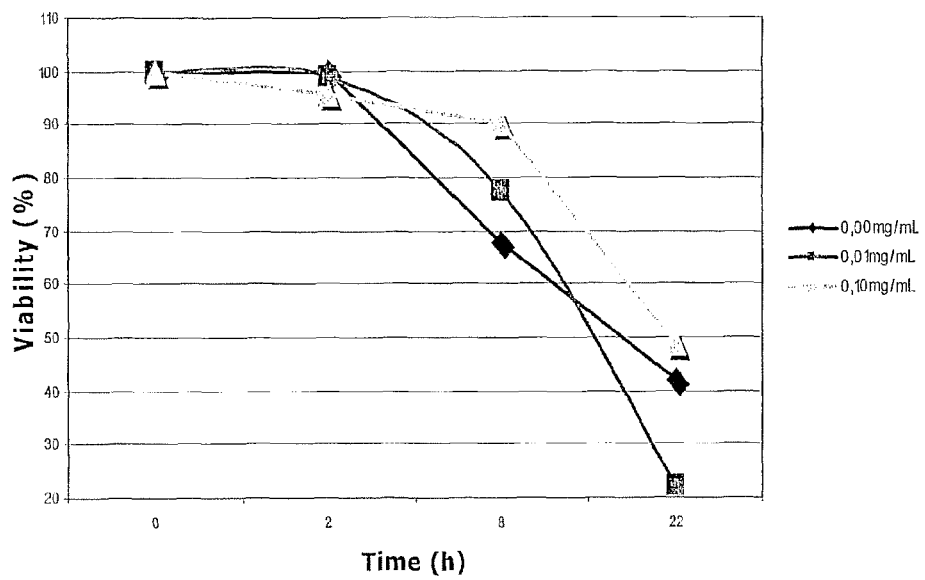
FIG. 25 is a representation of effects of compound 15 on HEK293 viability at −4° C.
Figure 26:
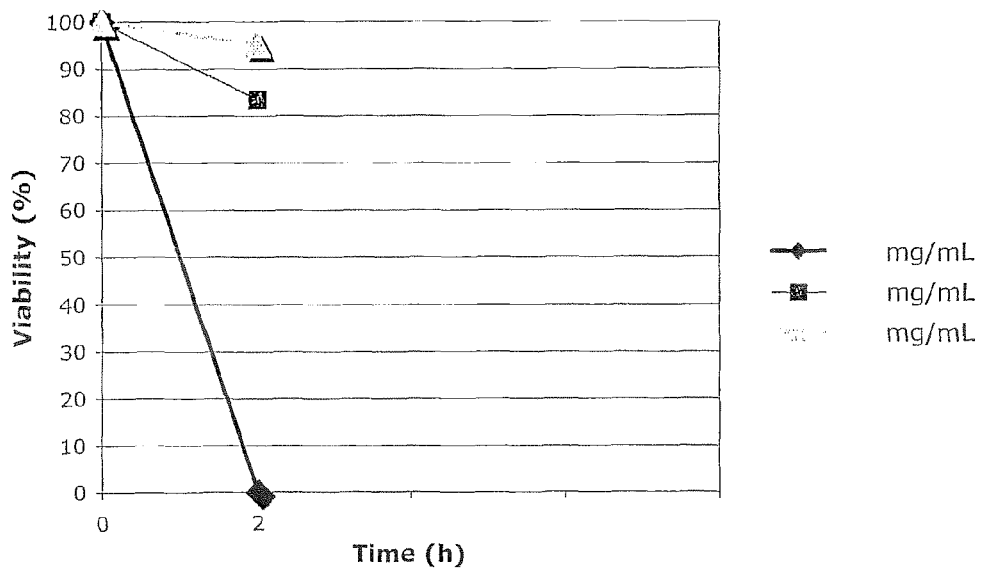
FIG. 26 is a representation of effects of compound 15 on HEK293 viability at −20° C.

F) Debenzylation of the Galactoside Units (FIG. 20):

A flask containing starting product 29 (90 mg; 0.05 mmol) in a mixture of acetic acid CH$_3$CO$_2$H (2.5 mL), tetrahydrofurane THF (0.8 mL) and water (0.8 mL) in the presence of a spatula tip of palladium on charcoal Pd/C is placed under a hydrogen atmosphere. The mixture is left under stirring overnight then filtered on a Millipore® filter. The mixture is concentrated to obtain product 30 in the form of a white solid with quantitative yield.

Characterization of Product 30:
$C_{40}H_{67}ClF_4N_8O_{21}$ M=1107.45 g.mol$^{-1}$
$^1$H NMR (D$_2$O, 300 MHz)
1.5 (m, 12H, 4CH$_3$); 1.7-2.0 (m, 12H, 6CH$_2$); 3.4 (m, 4H, 2NHCH$_2$); 3.7-4.5 (m, 18H, 2H6, CHNH (Lys), 2H3; 2H4; 2H5, 4CH (Ala), CHNH (Lys), 2H2); 7.2 (m, 40H, Har.).
$^{13}$C NMR (D$_2$O, 75.5 MHz)
16.9 et 17.0 (4CH$_3$); 21.7 et 22.6 (2CH$_2$); 27.9 et 30.8 (4 CH$_2$); 39.3 et 39.6 (2CH$_2$N); 49.6, 49.8 et 50.0 (4CH Ala); 53.2 et 53.8 (2NCH Lys); 61.1 et 62.6 (2C6); 67.1, 68.9, 70.6, 70.9, 72.4, 73.9, 75.5 80.2 (2C5, 2C4, 2C2, 2C3); 173.9, 174.5 et 175.1 (CONH et CO$_2$Me).
Masse (ESI+): 1071 (MH+); 1093 (M+Na); 1109 (M+K)

The invention is not restricted to the previously described examples.

The synthesis of a compound belonging to the general formula I, bearing a diaminoacid unit AA$_1$-AA$_2$ in R$^4$, will be easily obtained via two different processes using very classical chemical reactions already described in this text:
  starting from the glycopeptide 12 or 22, after deprotection of the NBoc moiety, the coupling reaction with the carboxylic function of the AA$_1$-AA$_2$ will lead to the desired compound after the usual N,O deprotection and debenzylation of the sugar unit.
  the introduction of the diaminoacid AA$_1$-AA$_2$ can also be done on a previous step and especially on the peptide 21 or 25 after deprotection of the Nboc via usual coupling reaction.

Then the deprotection of the side chain of the Lysine, and the coupling reaction with the carbohydrate derivatives 16 will give the glycopeptides after the usual deprotection steps.

Preliminary Preservation Tests of Biological Materials

Preliminary biological tests were conducted on the glycoproteins and notably the synthesized products. They enabled us to determine the effect of these compounds on different cell cultures at different temperatures and for varying periods of time. The purpose being to observe whether these compounds have a protective effect on cells.

The compounds 15 and 30 may be named in the following part AAGP or AFGP.

A) Effects of Product 15 on the Preservation of HEK 293 Kidney Cells

HEK 293 cells were cultured to 100% viability in a 75 cm$^2$ culture dish. The cells were then diluted to 75,000 cells/mL. Subsequently they were distributed over 6 plates with six 3 mL-wells per plate. This concentration is a good compromise between a concentration sufficiently low to prevent cell death by autocytotoxicity and sufficiently high to permit cell sampling and counting without any pre-concentration likely to reduce their survival. Each plate had two control wells not containing product 15, two wells with concentrations of product 15 adjusted to 0.01 mg/mL, and two others with 0.1 mg/mL. Each plate was then incubated at the following temperatures: 4° C., 2° C., 0° C., −2° C., −4° C., and −20° C. Each well was subsequently sampled at the following incubation times: 2, 8, and 22 hours.

Materials

| | |
|---|---|
| HEK 293 cells (Graham et al.) | DMEM cat # D5671, Sigma |
| Trypsin, Cat# 25-052-CI, MultiCell | PBS, Cat#SH30028.02, HyClone |
| Trypan Blue Cat# 72-57-1 | |

Consumables
    Micropipette tips, 200 µL, Axygen
    6 well plates for cell culture, cat#353046, Falcon
    T-Flask for cell culture75 cm2, cat #430725, Corning
    Pipettes, 2 mL, 5 mL, 10 mL and 25 mL, Falcon
Equipment

| | |
|---|---|
| Refrigerator, Danby | Freezer, Frigidaire |
| Incubator, Sanyo | Microscope, Zeiss |
| Inverted microscope, Olympus | Bench-top centrifuger, IEC |
| Hemocytometer, Rechter | Traceable digital thermometer, Fisher Scientific |
| Thermometers, VWR | Cell Counter, No. 8-004, HOPE |

Results

Cell counts showed that duplicated experiments are coherent with each other, since the differences do not exceed 10% with a sole exception showing a variation of 13%.

The cell cultures used to start the experiment were 100% and their morphological characteristics under the microscope showed good condition.

At five of the six tested temperatures (FIGS. 21-26), the presence of product 15 at 0.10 mg/mL (the highest concentration used for this experiment) led to the best cell survival rates even if the improvement remained low. The concentration of 0.01 mg/mL of product 15 does not appear to improve cell survival in comparison with the negative control.

At −20° C., after two hours, all the wells were frozen and the media had a gelatinous appearance. After thawing, microscopic observation showed that the control cells have a phantom appearance and immediately absorb Trypan blue, whilst the cells with compound 15 maintained the appearance of spherical retractile cells and did not absorb Trypan blue similar to living cells. Therefore, cell structure and morphology and some permeability functions were maintained in the presence of product 15 which was not the case with the control.

After this thawing, the plates were re-incubated at −20° C., but similar procedure after eight hours' incubation led to complete disappearance of all cells for both concentrations of product 15.

B) Effects of Product 15 on the Preservation of Erythrocytes.

The death of erythrocytes can be ascertained by rupture of the plasma membrane. This phenomenon is called haemolysis. Detection of haemolysis is the chief tool used in this experiment to determine the effect of product 15 at different temperatures on the preservation of erythrocytes.

Plan of Experiment

Blood sampling→Aliquots→Addition of AAGP (compound 15)→Various temperatures→Observation of haemolysis Product 15 was tested at concentrations of 0 mg/mL, 0.1 mg/mL, 1.0 mg/mL at temperatures of 3, 0, −3, −5, −10, −15, −23, −78° C.

From a sample of human blood in a borosilicate heparinized tube, microtubes of 275 µL were filled to full capacity. One third of the microtubes were completed with 2.75 µL of product 15 (10 mg/mL in H$_2$O), and one third of the microtubes were completed with 27.5 µL of product 15 (10 mg/mL in H$_2$O). The blood was divided among the tubes to full capacity to prevent air contact as much as possible.

The microtubes were incubated at different temperatures for different periods ranging from 2 to 9 hours. The microtubes were frozen on a microtube support and the experiment was conducted using a slow-freeze apparatus at −78° C., whilst thawing was always conducted at room temperature on the microtube rack. After thawing, the microtubes were delicately homogenized by inverting a few times and a sample of erythrocytes was taken. The erythrocytes (Ery) were diluted in PBS 500× and 2× in Trypan Blue before observation and before obtaining the haemolysis percentage such as defined in this equation:

$$\% \text{ Haemolysis} = [1-(Co-Cexp)]*100$$

in which: Co is the initial Ery count
    Cexp is the experimental Ery count

Materials

| |
|---|
| 15 mL human blood sample in borosilicate heparinized tube |
| PBS, Cat#SH30028.02, HyClone    Trypan Blue, Cat# 72-57-1 |

Consumables:

| | |
|---|---|
| Micropipette tips, 200 µL, Axygen | 200 µL PCR microtubes |
| 2 sterile heparinized tubes, Cat# 366480, Becton-Dickinson | |

Equipment:

| | |
|---|---|
| Fisher Isotemp low temperature Incubator, Fisher Scientific | |
| Refrigerator, Danby | Freezer, Frigidaire |
| Ultra-Low temperature Freezer | Slow-rate freezing device, Nalgene |

-continued

| Microscope, Zeiss | Digital camera, Olympus |
|---|---|
| Hemocytometer, Rechter | Traceable digital thermometer, Fisher Scientific |
| Thermometers, VWR | Cell Counter, No. 8-004, HOPE |

In table 1, it can be seen that there is no haemolysis in the temperature range of 2 to −10° C. The erythrocytes appear to remain intact from 0 to 24 hours after incubation at these temperatures whether with or without product 15.

TABLE 1

% Haemolysis vs. Incubation Time at Different Concentrations of product 15 and at 3, 0, −3, −5 and −10° C.

| Conc. Product 15 (mg/mL) | Incubation Time (h) | % Haemolysis | % Ery |
|---|---|---|---|
| 0.0 | 0 | 0 | 100 |
| 0.0 | 2 | 0 | 100 |
| 0.1 |  | 0 | 100 |
| 1.0 |  | 0 | 100 |
| 0.0 | 4 | 0 | 100 |
| 0.1 |  | 0 | 100 |
| 1.0 |  | 0 | 100 |
| 0.0 | 9 | 0 | 100 |
| 0.1 |  | 0 | 100 |
| 1.0 |  | 0 | 100 |
| 0.0 | 24 | 0 | 100 |
| 0.1 |  | 0 | 100 |
| 1.0 |  | 0 | 100 |

The blood samples were placed at −15° C. for the same times. In table 2, after two hours, it can be seen that product 15 partly protects the erythrocytes at a concentration of 0.1 mg/mL and completely at 1.0 mg/mL. At 4 and 9 hours, complete protection is only obtained with a concentration of 1.0 mg/mL.

TABLE 2

% Haemolysis vs. Incubation Time at Different Concentrations of product 15 at −15° C.

| Conc. Product 15 (mg/mL) | Incubation time (h) | Number of erythrocytes | % Haemolysis | % Ery |
|---|---|---|---|---|
| 0.0 | 0 | 123 | 0 | 100 |
| 0.0 | 2 | 0 | 100 | 0 |
| 0.1 |  | 90 | 27 | 73 |
| 1.0 |  | 120 | 2 | 98 |
| 0.0 | 4 | 0 | 100 | 0 |
| 0.1 |  | 0 | 100 | 0 |
| 1.0 |  | 133 | 0 | 100 |
| 0.0 | 9 | 0 | 100 | 0 |
| 0.1 |  | 0 | 100 | 0 |
| 1.0 |  | 121 | 2 | 98 |

More extreme conditions were also tested. At −23° C. and −78° C., the erythrocytes ruptured if these temperatures are reached rapidly.

Therefore, a test was conducted using slow cooling to reach −78° C. A blood sample without product 15 was incubated for different times to determine the freezing point. As can be seen in table 3, the freezing point is reached after 40 minutes. At this instant a direct correlation is observed between % haemolysis and concentrations of product 15.

TABLE 3

% Haemolysis vs. Different Concentrations of product 15 at −78° C. with slow cooling

| Conc. Produit 15 (mg/mL) | Time (min) | % Haemolysis | % erythrocytes |
|---|---|---|---|
| 0.0 | 0 | 0 | 100 |
| 0.0 | 15 | 0 | 100 |
| 0.0 | 35 | 0 | 100 |
| 0.0 | 40 | 0 | 100 |
| 0.1 |  | 36 | 64 |
| 1.0 |  | 97 | 3 |
| 0.0 | 50 | 100 | 0 |

In most cases, except after 2-hours incubation at −15° C., either complete or no haemolysis at all is observed. It is evident that the haemolysis process is very rapid and occurs on freezing. The fact that at a temperature below −15° C., no protection is observed by product 15 at 1.0 mg/mL, may mean that this compound protects the erythrocytes by reducing the freezing process rather than by stopping it, at least with concentrations of 1.0 mg/mL. The phenomenon of crystallization leads to rupture of the erythrocyte membranes. However, by decreasing the time (less than two hours) it could be gained more details on the dynamics of haemolysis in the vicinity of the freezing point. It is observed however that product 15 really protects the erythrocytes at −15° C.

C) Effects of Product 15 on the Preservation of Blood Platelets.

The purpose is to test product 15 on the preservation of blood platelets to improve current protocols which only allow their preservation for 5 days. The test was conducted at four different temperatures 22° C., 15° C., 4° C. and finally 0° C. Platelet follow-up lasted 21 days to examine platelet clustering. Clustering is one of the first and most definitive indicators of platelet degradation. During their degradation, the platelets become active, lose their morphology, become fibrous, form clusters and finally degenerate. A platelet count is made but the result is rather more based on the extent of clustering.

Figure 27:
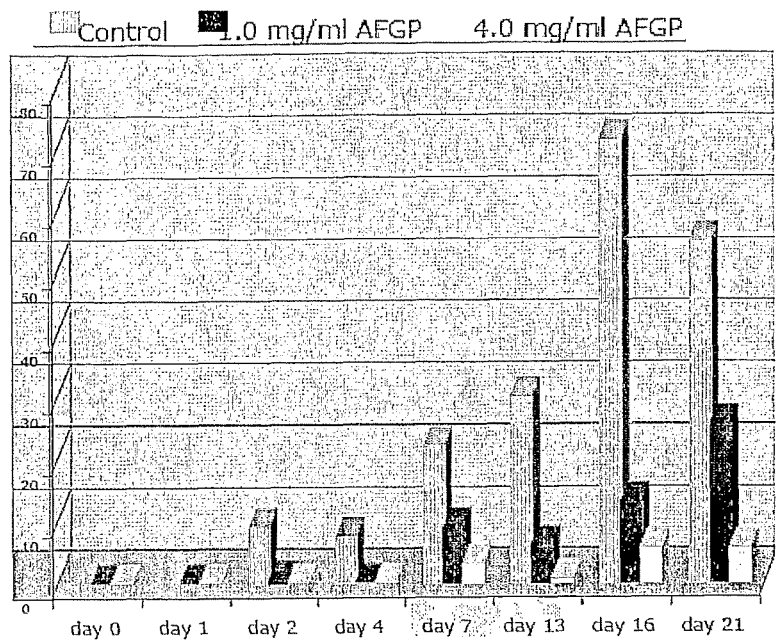
FIG. 27 is a representation of effects of compound 15 on platelet aggregation at 22° C.
Figure 29:
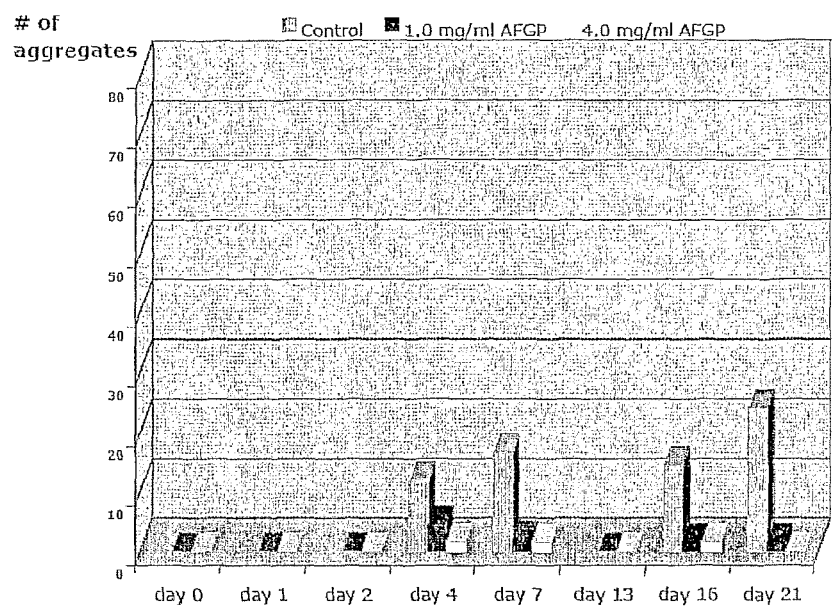
FIG. 29 is a representation of effects of compound 15 on platelet aggregation at 4° C.

FIGS. 27 and 29 show a positive effect on platelet clustering due to the presence of product 15. In FIG. 27, at 22° C., the results (negative control, 1 mg/mL and 4 mg/mL of product 15) are compared. It is observed that almost immediately (after two days), clustering starts to occur in the control and continues to increase, whereas the samples with glycoprotein 15 do not show any clusters before up to 7 days. In the course of time at 13, 17 and 21 days a much more marked difference is seen and hence a true inhibition of platelet clustering by product 15. It is the most concentrated samples (4 mg/mL) which show the least clustering.

Figure 28:
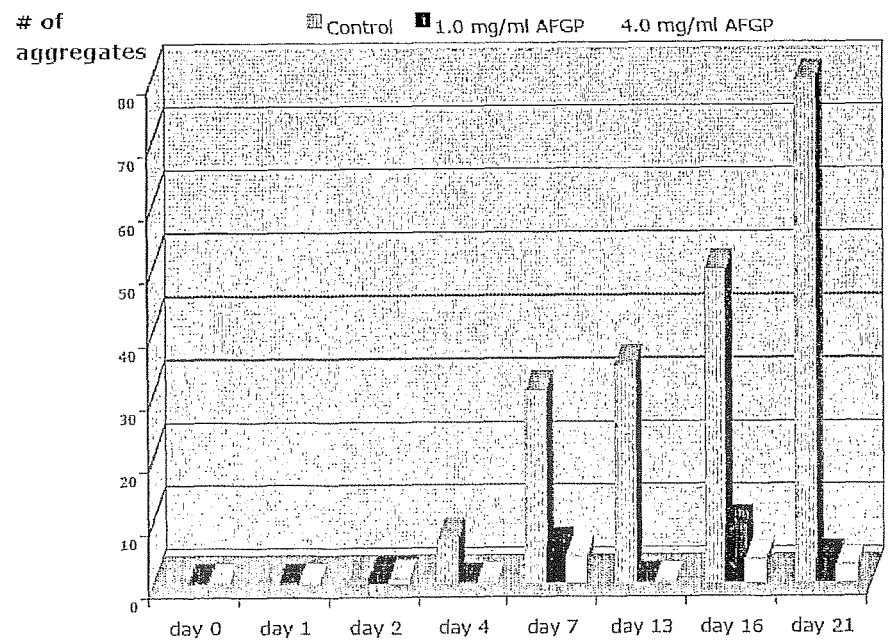
FIG. 28 is a representation of effects of compound 15 on platelet aggregation at 15° C.

FIG. 28 at 15° C. shows the same type of results as previously. Clustering at this temperature starts becoming notably apparent after 4 days. Over time, a greater increase in clustering is observed in the control than in the samples containing the compound. However there are fewer clusters at this temperature than at 22° C.

At 4° C. (FIG. 29), almost no clustering is observed with product 15 irrespective of concentrations. In the control, the number of clusters is also markedly lower than at the other temperatures.

At 0° C. no clustering is seen, whether with or without glycoprotein 15.

D) Effects of Products 15 and 30 on the Preservation of Heart Myoblasts.

The purpose of this experiment was to examine the effect of gem-difluoro glycoproteins on the cells of heart tissue, and also to make a comparison between the monomer (product 15) and dimer (product 30) of synthesized compounds.

The test was conducted on rat heart myoblasts to consider application of these compounds for the preservation of organs such as the heart for subsequent transplant.

Preliminary Experiment
1) The cells are thawed and cultured until doubling is stable in DMEM medium, at 5% $CO_2$ and 37° C.
2) The cells are amplified in a flask.
3) 300 μL with 100 000 cells are divided among the microtubes
4) 3 μL PBS is added to a negative control tube
5) In three microtubes 0.3, 1.5 and 3 μL of 100 mg/mL of product 15 are respectively added to obtain a concentration of 0.1, 0.5 and 1 mg/mL,
6) In three microtubes 0.3, 1.5 and 3 μL of 100 mg/mL of product 30 are respectively added to obtain a concentration of 0.1, 0.5 and 1 mg/mL.
6) The cells are incubated at −2° C.
7) The cells are sampled at 0, 2, 7, 20 and 43 hours after incubation.

Main Experiment
1) The cells are amplified in a flask
2) 300 μL with 100 000 cells are divided among the microtubes
3) 3 μL PBS are added to four negative control tubes
4) In four tubes 3 μL of product 15 are added to obtain 1 mg/mL
5) In four tubes 3 μL of product 30 are added to obtain 1 mg/mL
6) A set of tubes (Control-Monomer-Dimer) is incubated at room temperature (22° C.)
7) A set of tubes (Control-Monomer 15-Dimer 30) is incubated at 4° C.
8) A set of tubes (Control-Monomer 15-Dimer 30) is incubated at −3° C.
9) A set of tubes (Control-Monomer 15-Dimer 30) is incubated at −10° C.
10) Each tube is sampled to count living and dead cells at 0, 8, 16 and 22 hours after incubation
11) Only the tube of monomer 15 at −3° C. is sampled at 0, 8, 12, 16, 20 and 22 hours for the count of living and dead cells.

Materials

| | |
|---|---|
| H9c2(2-1) cells, ATCC Number CRL-1446, adherent cell line derived from rat myocardial tissue (1, 2, 3) | |
| DMEM 4 mM L-Glutamine | |
| Incubators, 37, 22, 4, −3, −2 and −10° C. | |
| Pipetters | Micropipette tips |
| Hemacytometer | Trypan Blue |
| Microscope | Cell counter |
| Microtubes | Microtubes rack |

Figure 30:
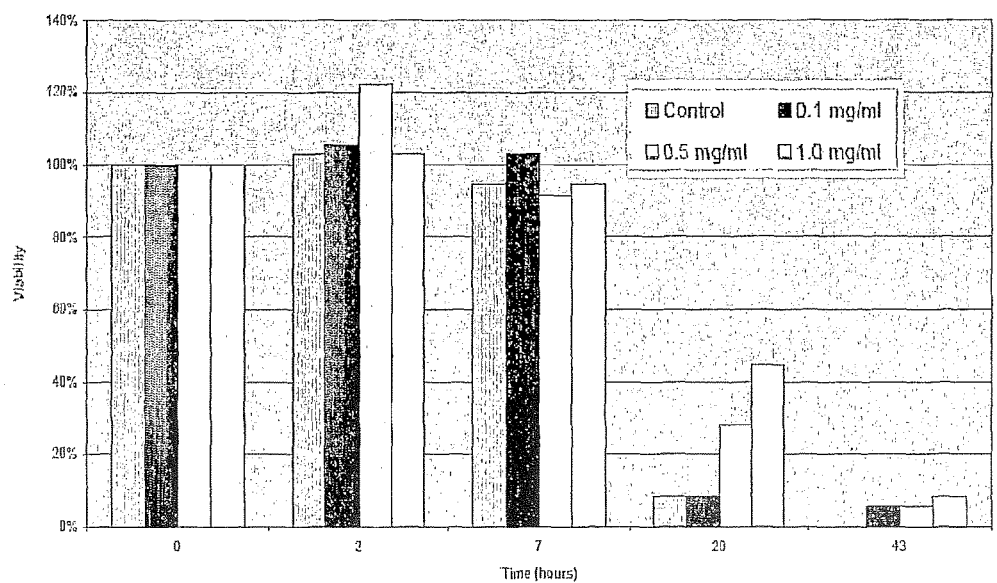
FIG. 30 is a representation of effects of compound 15 (monomer) on preservation of H9c2(2-1) cells at −2° C.

For the Preliminary Experiment:

For monomer 15 at 2° C. (FIG. 30), the survival percentage is very close to 100% with all concentrations at 0, 2 and 7 hours. At 20 hours, this percentage decreases to 44% for 1 mg/mL, to 28% for 0.5 mg/mL while 0.1 mg/mL is identical to the control. This leads to supposing a protective effect dependent upon the concentration of glycoproteins.

Figure 31:
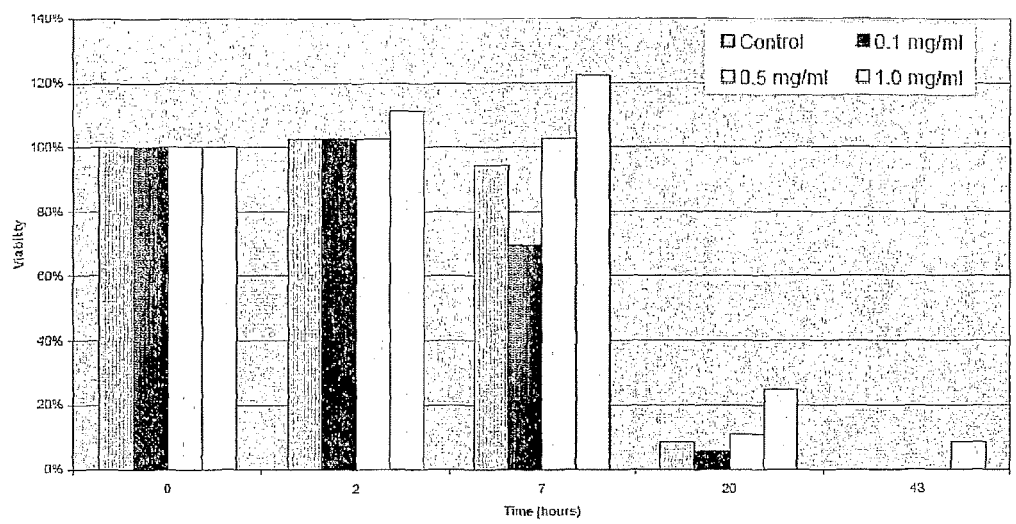
FIG. 31 is a representation of effects of compound 30 (dimer) on preservation of H9c2(2-1) cells at −2° C.

For dimer 30 (FIG. 31) using the same procedure, identical results are observed. After 20 hours, the cell survival percentage is 25% at 1 mg/mL, 11% at 0.5 mg/mL and 6% at 0.1 mg/mL.

Figure 32:
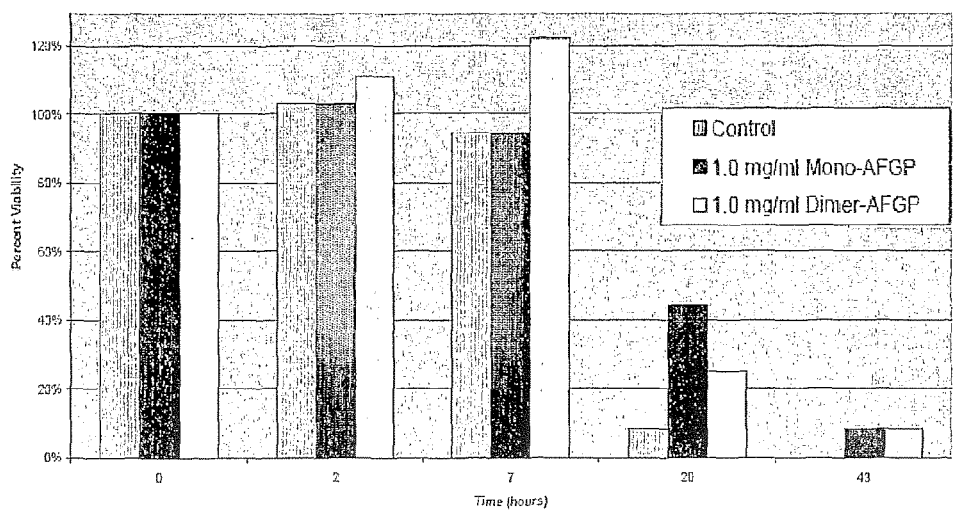
FIG. 32 is a representation of a comparison of Monomer 15 vs. Dimer 30 at various time.

When the two glycoproteins are compared in parallel (FIG. 32), the most significant result is with 1 mg/mL for which a protective effect of the two compounds 15 and 30 is observed on the cells after 20 hours with 44% survival for monomer 15 and 25% for dimer 30, compared with only 8% for the control.

Figure 33:
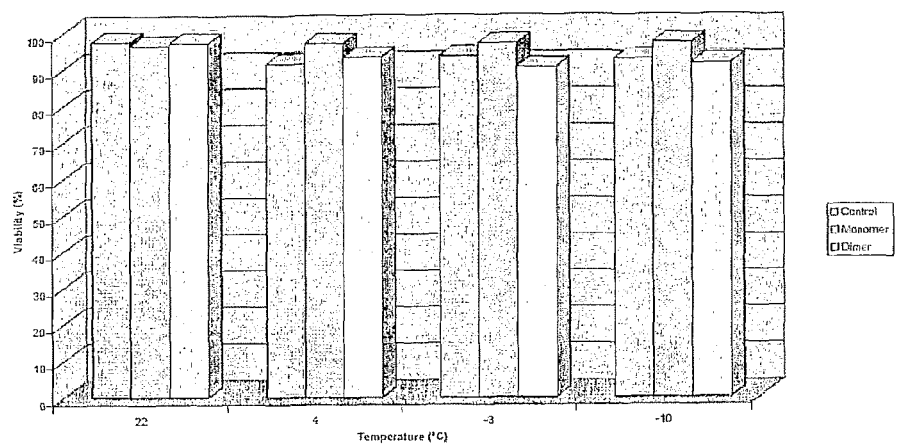
FIG. 33 is a representation of viability of heart cells after exposure of 8 Hours with 1 mg/mL of monomer 15 and dimer 30.
Figure 34:
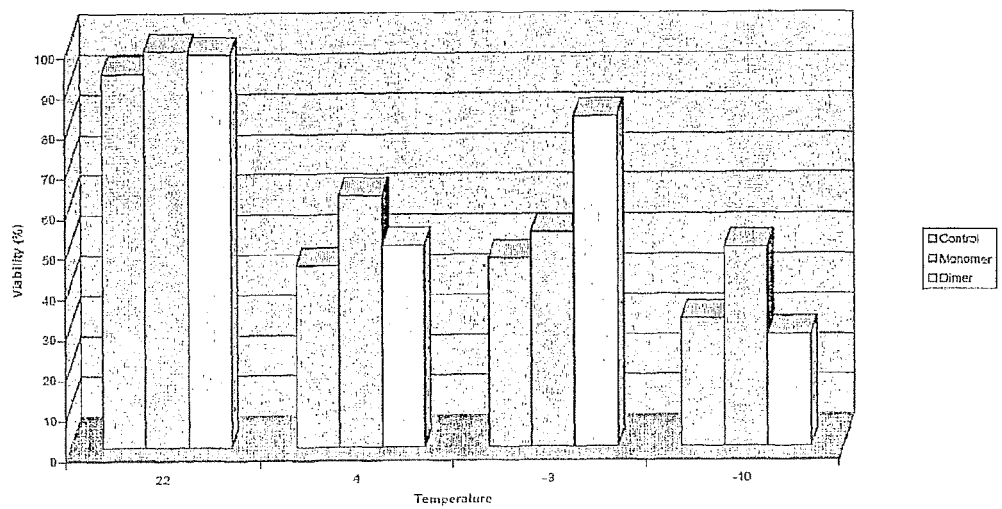
FIG. 34 is a representation of viability of heart cells after exposure of 16 Hours with 1 mg/mL of monomer 15 and dimer 30.
Figure 35:
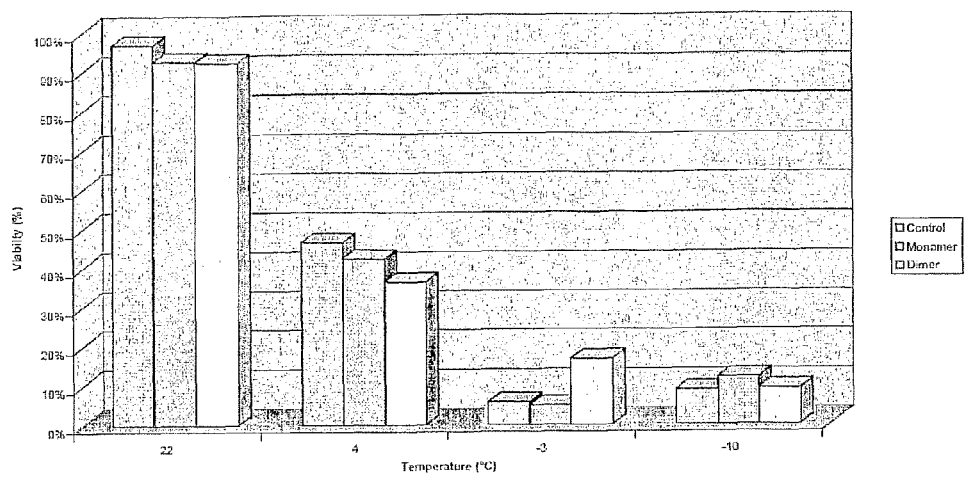
FIG. 35 is a representation of viability of heart cells after exposure of 22 Hours with 1 mg/mL of monomer 15 and dimer 30.

For the Main Experiment:

This is performed with 1 mg/mL concentrations of monomer 15 or dimer 30 at 4 different temperatures: 22, 4, −3 and −10° C. There is no significant difference for up to 8 hours at all temperatures (FIG. 33). After 16 hours (FIG. 34), a strong correlation is observed between the presence of glycoprotein and cell survival percentage compared with the negative control at temperatures of 4 and −3° C. Unfortunately these results do hot make it possible for a conclusion to be drawn as to which of the two forms has the best protective effect; at 4° C. it is monomer 15 which gives the best results, while at −3° C. it is the dimer 30. After 22 hours (FIG. 35), there is a major fall in the number of living cells. However, at −3° C., the dimer form is noted to have an effect with a survival percentage of 17%.

Figure 36:
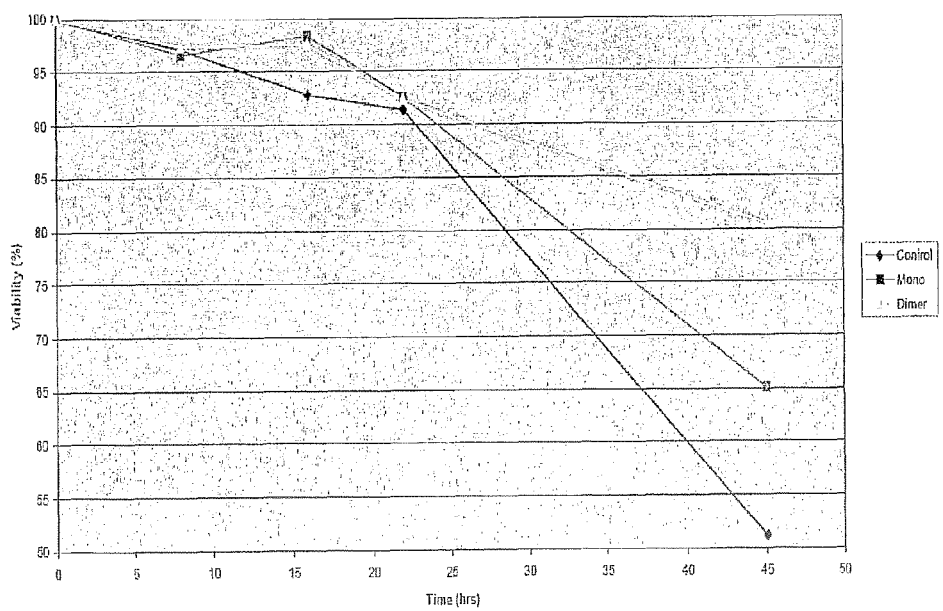
FIG. 36 is a representation of viability of heart cells over time at room temperature (22° C.) in presence of 1 mg/mL of monomer 15 and dimer 30.

At 22° C. (FIG. 36), after 45 hours, a 51% survival is observed in the control while the monomer 15 and dimer 30 only fall to 65 and 80% respectively.

Figure 37:
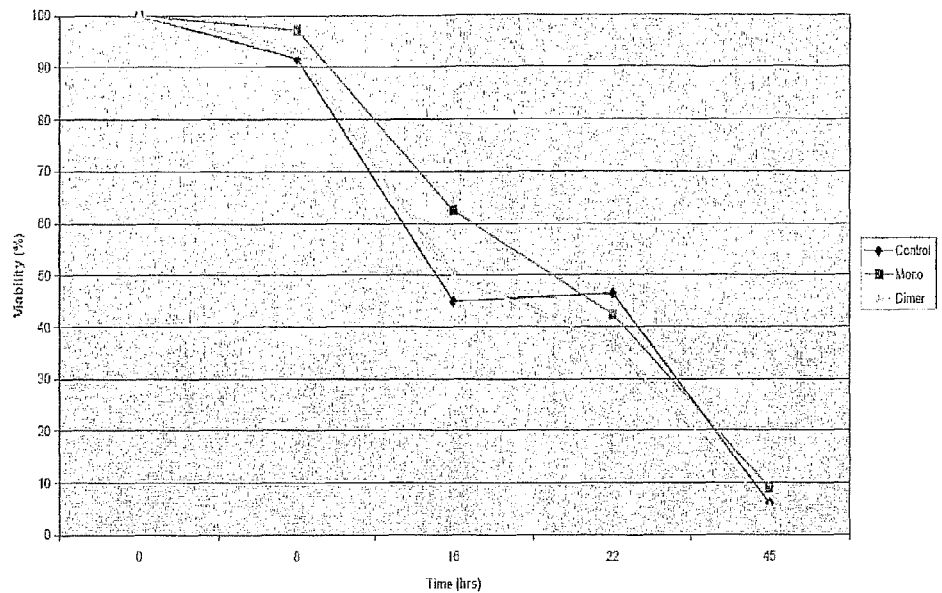
FIG. 37 is a representation of viability of heart cells over time at 4° C. in presence of 1 mg/mL of monomer 15 and dimer 30.
Figure 38:
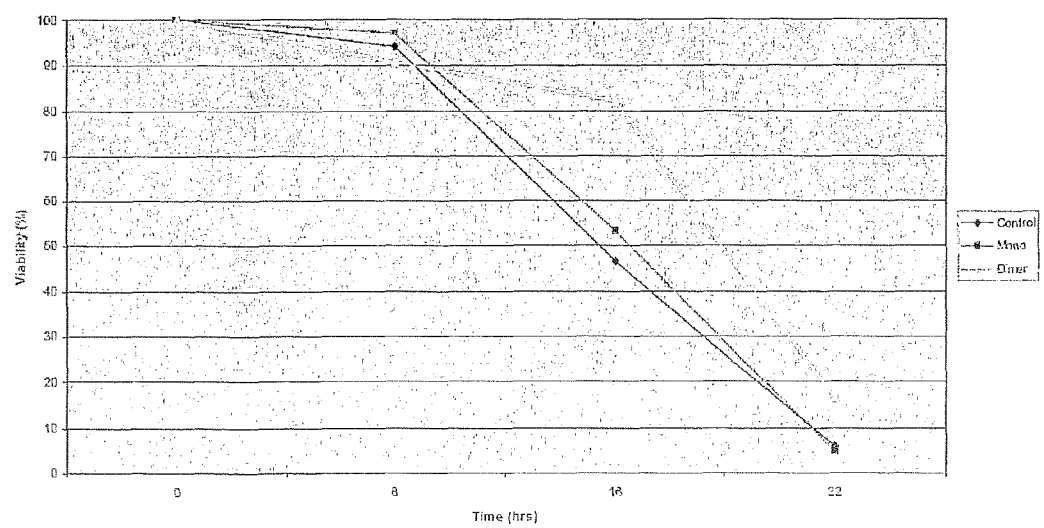
FIG. 38 is a representation of viability of heart cells over time at −3° C. in presence of 1 mg/mL of monomer 15 and dimer 30.

The same type of curve is obtained at 4° C. (FIG. 37), with a final result that is less convincing at 45 hours, but showing a better survival percentage over the entire duration of the experiment for the monomer. At −3° C. (FIG. 38), the result is similar with the dimer, especially in the range of 8-22 hours.

Figure 39:
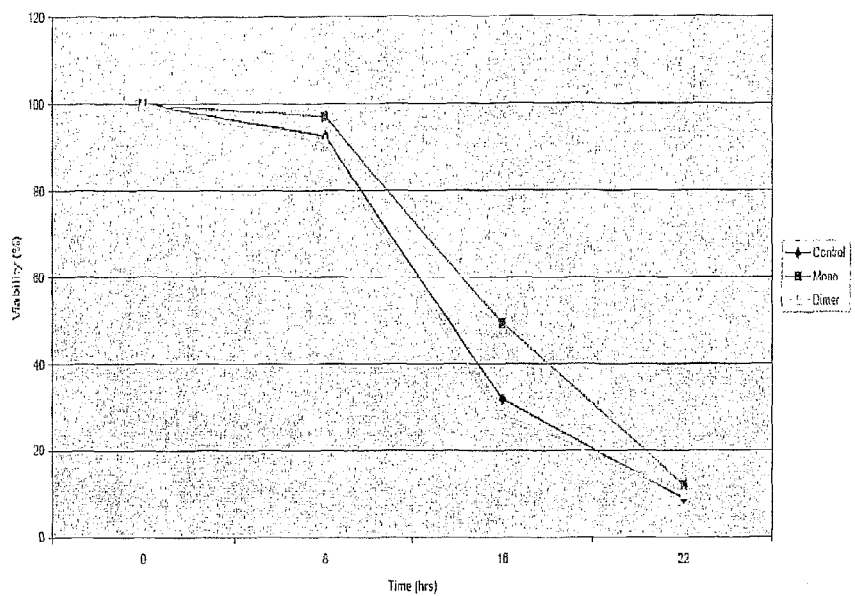
FIG. 39 is a representation of viability of heart cells over time at −10° C. in presence of 1 mg/mL of monomer 15 and dimer 30.

At −10° C. (FIG. 39), similar results are observed for the dimer and the control, and a slight improvement for the monomer.

Figure 40:
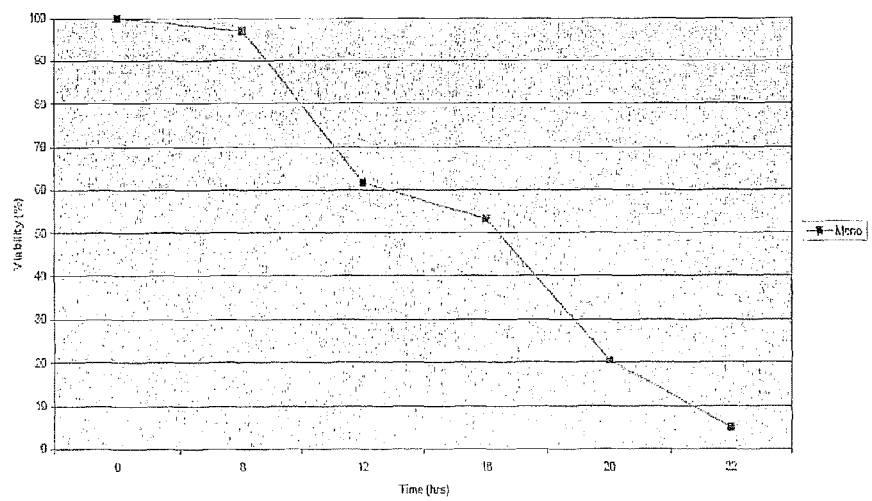
FIG. 40 is a representation of viability of heart cells over time at 3° C. in presence of 1 mg/mL of monomer 15.

FIG. 40, at −3° C., shows the slow decrease over incubation time in the number of living cells with the presence of the monomer.

During these experiments on myoblasts, it was found that the monomer and dimer compounds have a protective effect on these cells. It appears that:

There exists a correlation between the increase in concentration of glycoproteins 15 and 30 and cell survival rate, monomer 15 and dimer 30 giving better results at 1 mg/mL than at 0.1 and 0.5 mg/mL.

The effect is only seen to be marked after 8 hours. All the experiments show results of interest essentially between 8 and 20 hours.

The protective effect of most interest is apparent at 4° C. and −3° C.

It is impossible to confirm whether it is the monomer or dimer which is the most active.

Another test was conducted on myoblasts at temperatures of 3° C. and −3° C. The purpose of the experiment this time was to increase the concentrations of glycoproteins 15 and 30 equimolar fashion (the molecular weight of the dimer being 2× greater than that of the monomer). The increase in concentration was 2.5 mg/mL for monomer 15 and 5 mg/mL for dimer 30. The temperatures were chosen over a range frequently used for the preservation of cells and tissues. The idea being subsequently to continue this experiment directly on tissues.

Method
1) The cells are expanded in a flask.
2) Three tubes with 1.0 mL cells are prepared with 0.2×10⁶ cells/mL
3) To one tube, 25 μL of monomer 15 at 100 mg/mL are added to obtain 2.5 mg/mL (4.3 mM)
4) To another tube, 50 μL of dimer 30 at 100 mg/mL are added to obtain 5.0 mg/mL (4.5 mM)

5) The tubes are sampled in plates of 2×96 wells with 100 μL per well
6) One plate is incubated at 3° C. and the other at −3° C.
7) The count of living and dead cells is made at 0, 8, 12, 16, 20 and 24 hours.

Figure 41:
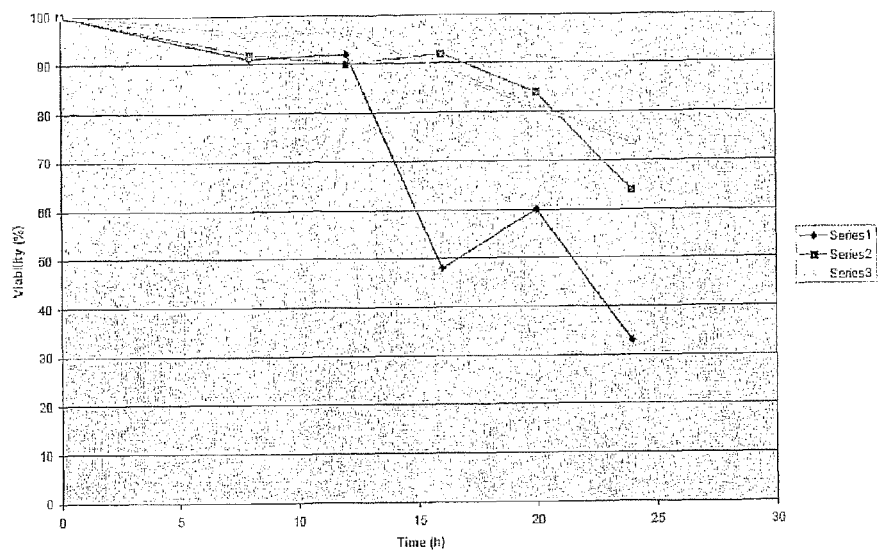
FIG. 41 is a representation of viability of heart cells at 3° C. and 4.4 mM of glycoproteins 15 and 30.
Figure 42:
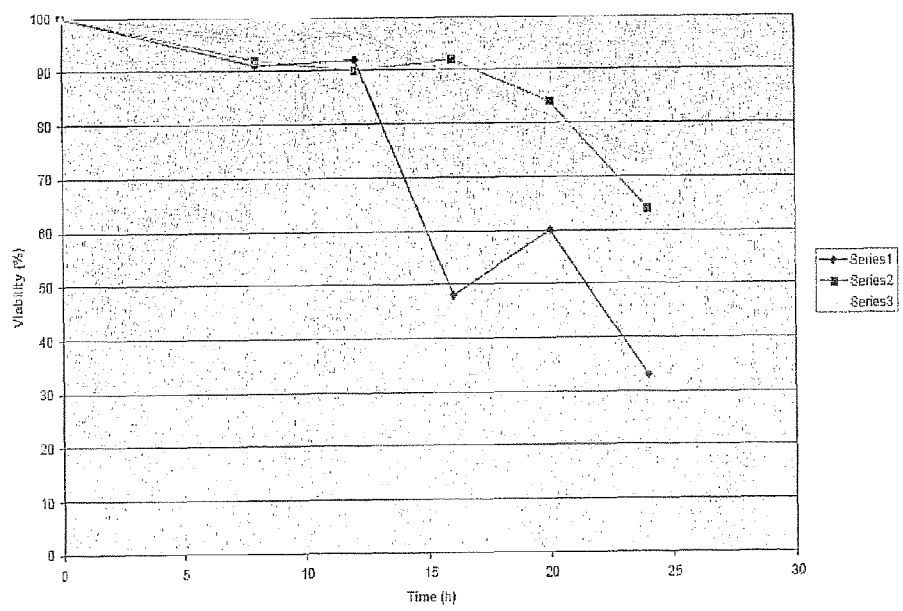
FIG. 42 is a representation of viability of heart cells at −3° C. and 4.4 mM of glycoproteins 15 and 30.

FIGS. 41 and 42 give the cell survival rate in the negative control, in the presence of monomer and dimer at 3° C. and −3° C. after 8, 12, 16, 20 and 24 hours.

According to FIGS. 41 and 42 the heart cells survive longer at −3° C. than at 3° C. After 24 hours, there is no survival at 3° C. whereas at −3° C. with the dimer a survival rate of 70% is observed.

In most cases, the monomer gives the same results as the dimer. FIG. 42 shows that at 3° C. the control falls to a survival rate of 19% after 8 hours, whereas it remains more than twice as high with the monomer and four times more with the dimer. AAGP therefore extends the survival of heart cells especially between 8 and 12 hours, but also up to 24 hours.

Figure 43:
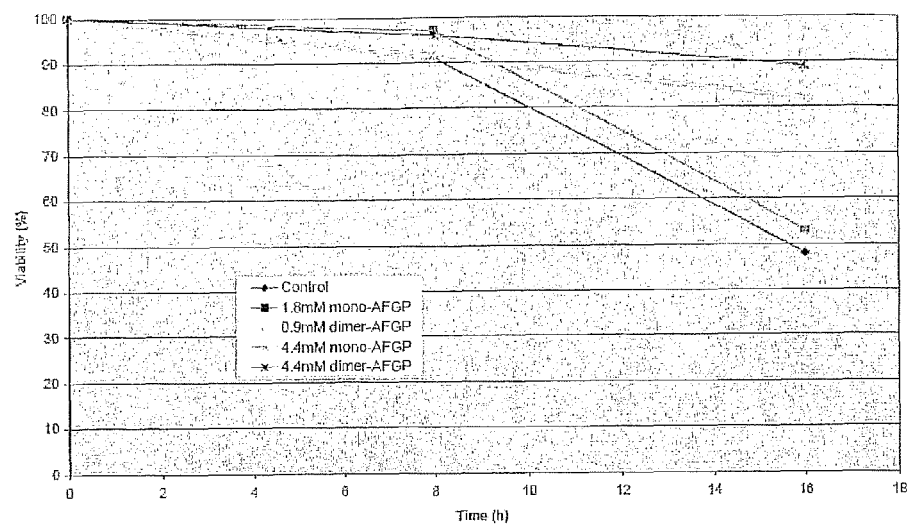
FIG. 43 is a representation of viability of heart cells at −3° C. with increasing concentration of glycoproteins 15 and 30.

In FIG. 43, the data from the preceding experiment at 1 mg/mL have been combined with the largest concentrations used for this experiment. These compounds 15 and 30 have greater efficacy at higher concentrations.

These results highlight the protective role of products 15 and 30 on cell survival in relation to concentration. The results of most interest appear in FIGS. 41 and 42. After 24 hours, approximately 75% of the myoblasts are still living with the dimer and 65% with the monomer, whereas only 30% remain in the control. Even after 16 hours, the monomer and dimer preserve approximately 90% of the cells.

In addition when the concentration of glycoproteins increases, cell survival is the same whether for the monomer or the dimer (FIG. 43).

The results therefore show that the cells derived from myoblasts are viable when preserved at low temperature in the presence of products 15 and 30.

E) Effect of Product 15 on the Preservation of Skin Fibroblasts

The purpose is to test product 15 on skin fibroblasts at different temperatures.

1) The cells are thawed and cultured until doubling is stable in DMEM medium with 5% $CO_2$ at 37° C.
2) The cells are amplified in a Petri dish
3) Cell concentration is brought to $0.27 \times 10^6$ cells/mL
4) 1.8 mL of cell suspension are completed with 90 μL AFGP mother solution at 100 mg/mL and evenly distributed in four cell culture plates, 100 μL per well.
5) 1.8 mL of cell suspension are completed with 90 μL of PBS solution and uniformly distributed over 4 cell culture plates, 100 μL per well.
6) One plate is incubated at 22° C., another at 3° C., another at −3° C., and the final plate at −20° C.
7) The cells are sampled at 8, 12, 20 and 30 hours to follow up cell viability using the Trypan Blue exclusion technique.

Materials

| | |
|---|---|
| Cells CCD-27Sk, ATCC Number CRL-1475, Adherent normal fetal fibroblast skin cells from human (1) | |
| DMEM 4 mM L-Glutamine | Incubators, 22, 3 and −3° C. |
| Pipetters | Micropipette tips |
| Hemacytometer | Trypan Blue |
| Microscope | Cell counter |
| Microtubes | Microtubes rack |
| Cell culture plate, Costar 96-wells, flat bottom, non-treated for cell culture. | |

Figure 44:
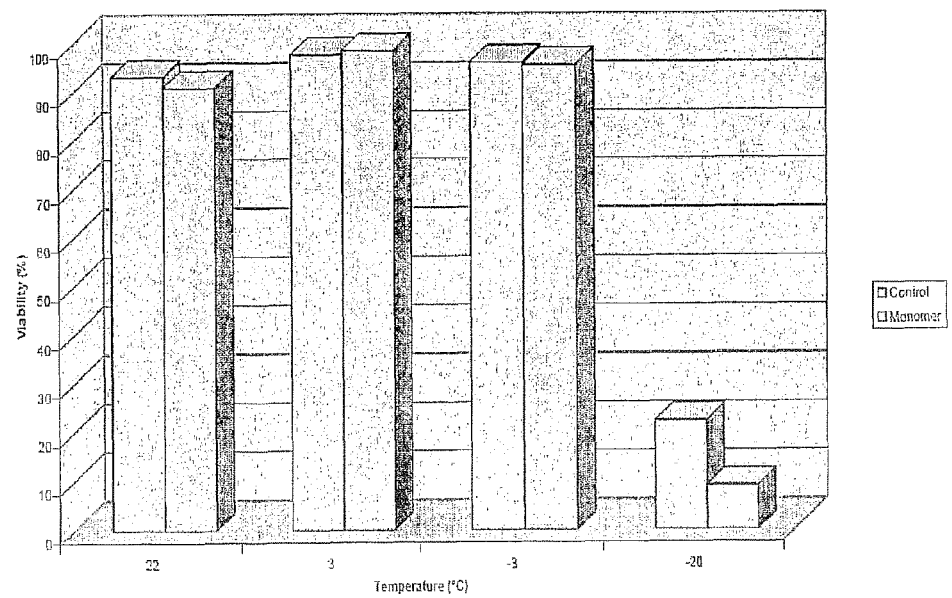
FIG. 44 is a representation of viability of skin cells after exposure of 8 hours of 5 mg/mL Monomer 15.
Figure 45:
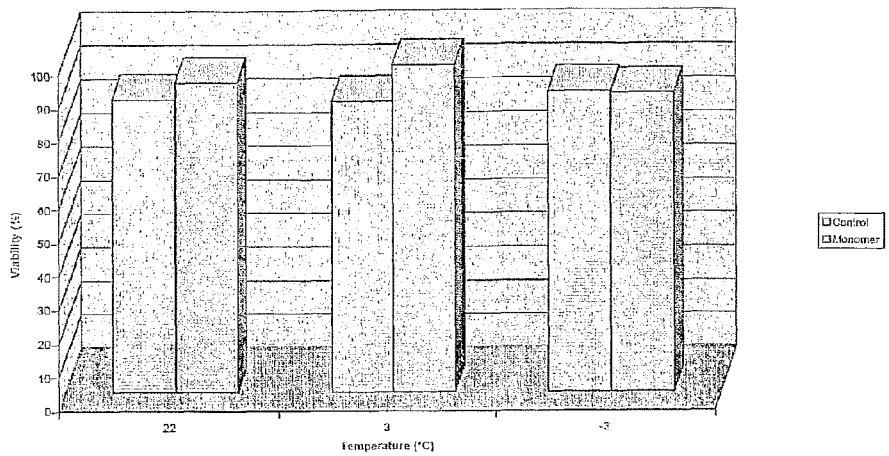
FIG. 45 is a representation of viability of skin cells after exposure of 12 hours of 5 mg/mL Monomer 15.

In FIG. 44, no difference is found between the cells preserved with or without product 15 over the entire temperature range. However, at −20° C. the samples freeze leading to death of the cells after thawing.

Figure 46:
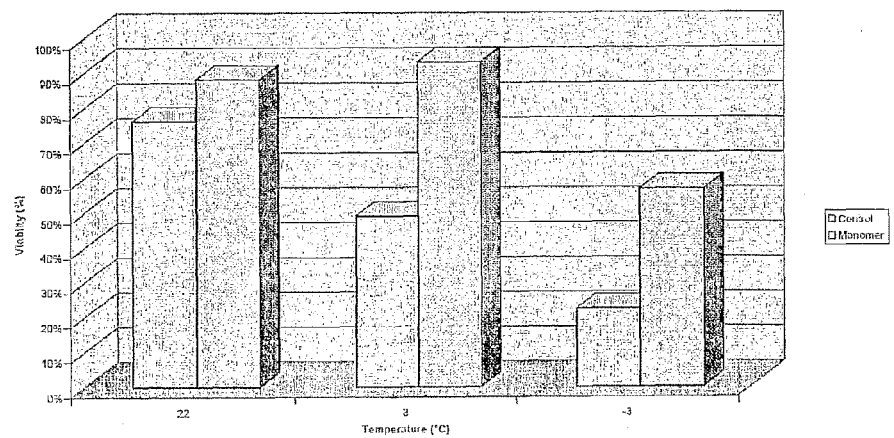
FIG. 46 is a representation of viability of skin cells after exposure of 20 hours of 5 mg/mL Monomer 15.
Figure 47:
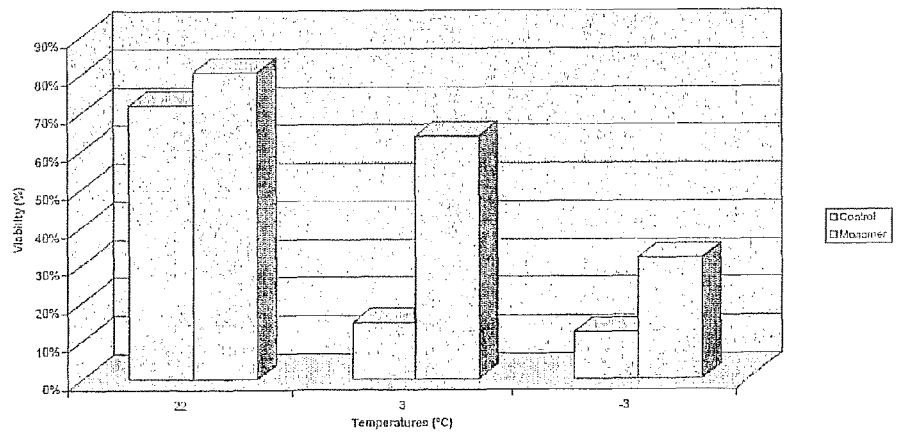
FIG. 47 is a representation of viability of skin cells after exposure of 30 hours of 5 mg/mL Monomer 15.

After 12 hours, still no major difference is seen over the range 22° C., 3° C. and −3° C., on the other hand better preservation is seen to occur with compound 15 at 22° C. and −3° C., In FIG. 46, results show a better cell survival rate with monomer 15 than with the control. Nonetheless, at −3° C., the survival rate decreases to 50% even in the presence of the monomer. After 30 hours (FIG. 47), the cells protected by product 15 show a distinct improvement especially at 3° C. At −3° C., even if the presence of the compound improves survival, it is reduced to 70%.

Figure 48:
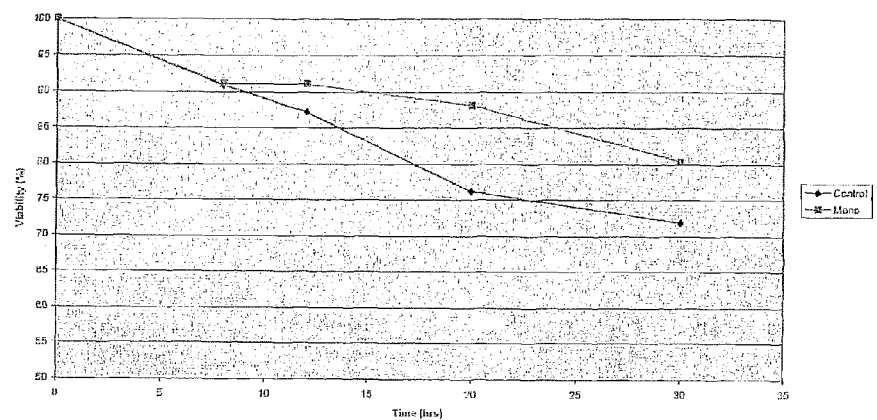
FIG. 48 is a representation of viability of skin cells over time at room temperature (22° C.) in presence of 5 mg/mL Monomer 15.
Figure 49:
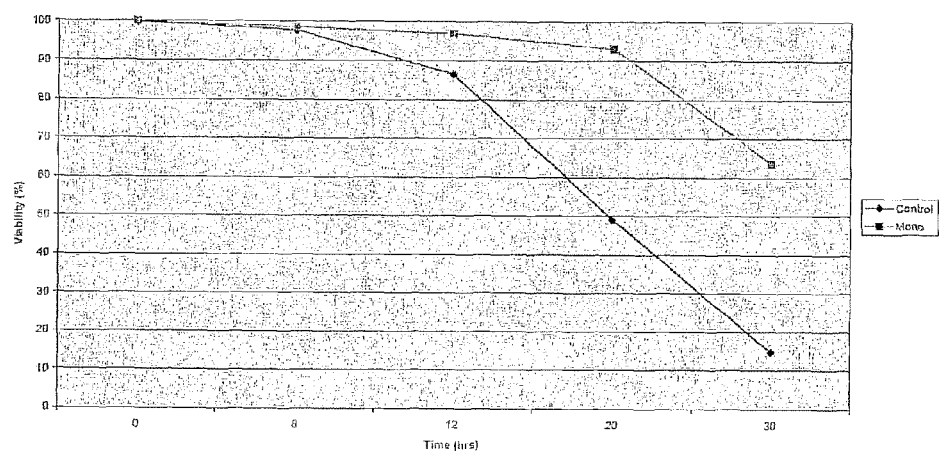
FIG. 49 is a representation of viability of skin cells over time at 3° C. in presence of 5 mg/mL Monomer 15.
Figure 50:
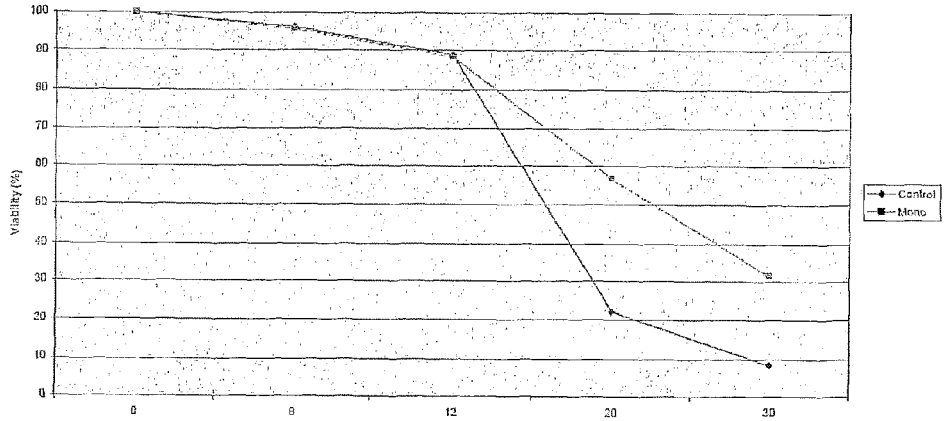
FIG. 50 is a representation of viability of skin cells over time at −3° C. in presence of 5 mg/mL Monomer 15.

If the trend over time is followed at the same temperature (FIGS. 48 to 50), it is noted that the control shows a rapid decrease in survival at −3° C., a decrease at 3° C. and a slow decrease at 22° C. The same type of pattern is found in the presence of product 15 but, by comparison, with much better survival rates.

The use of 5 mg/mL monomer 15 corresponds to 8.6 mM. This is the first experiment we have conducted at said concentration and results are extremely positive in that the skin fibroblasts show better preservation in the presence of product 15 at all temperatures except at −20° C. when the cells freeze and die whether or not the monomer is present. The best improvements are found at 3° C.

It was therefore decided to work at 3 and −3° C. but with higher concentrations of compound 15 of up to 15 mg/mL.

Figure 51:
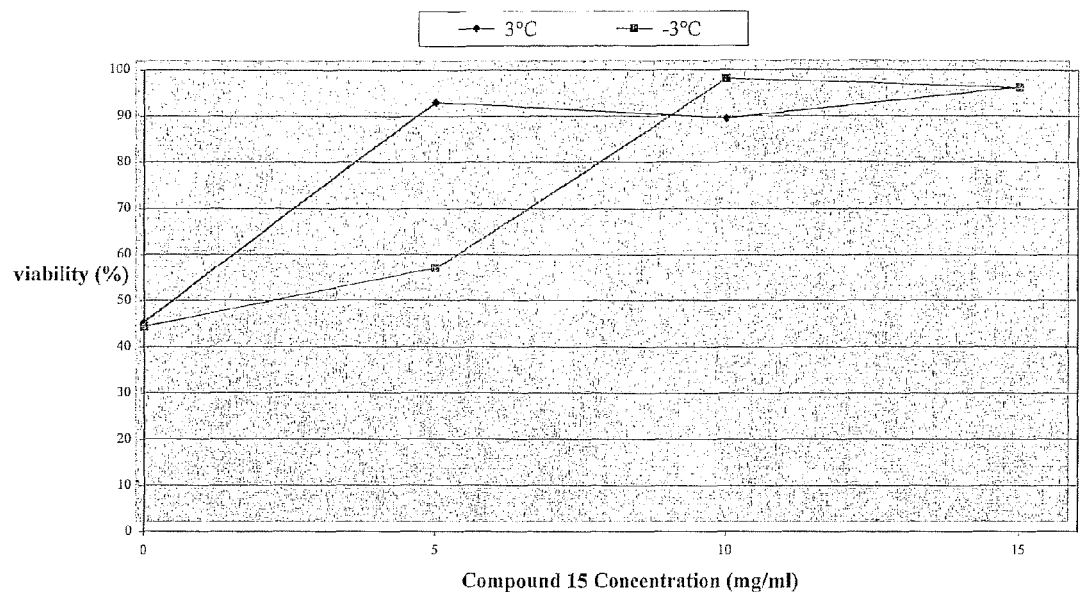
FIG. 51 is a representation of viability of skin cells after exposure of 20 hours at increasing concentrations of compound 15.
Figure 52:
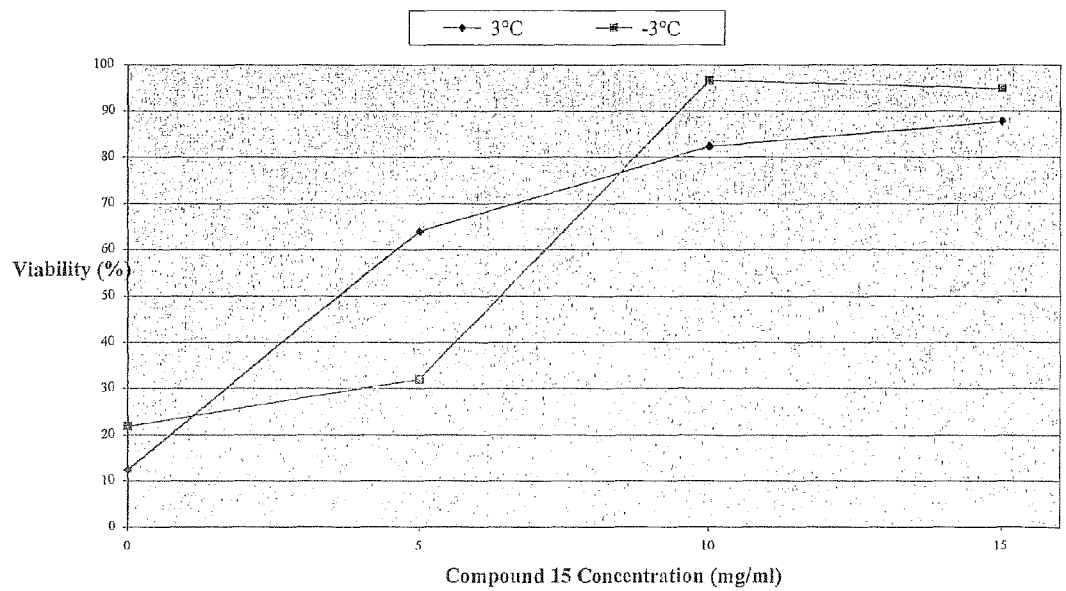
FIG. 52 is a representation of viability of skin cells after exposure of 34 hours at increasing concentrations of compound 15.

FIGS. 51 and 52 clearly indicate that the increase in concentration of product 15 improves cell survival rate at 3 and −3° C. These results show that compound 15 has a strong protective effect on cells that is close to 100% even after 34 hours.

The potential of these compounds (10 mg/mL) was also assessed on fibroblasts at 37° C. and 15° C., which could be of interest for the application of these compounds in cosmetology.

Figure 53:
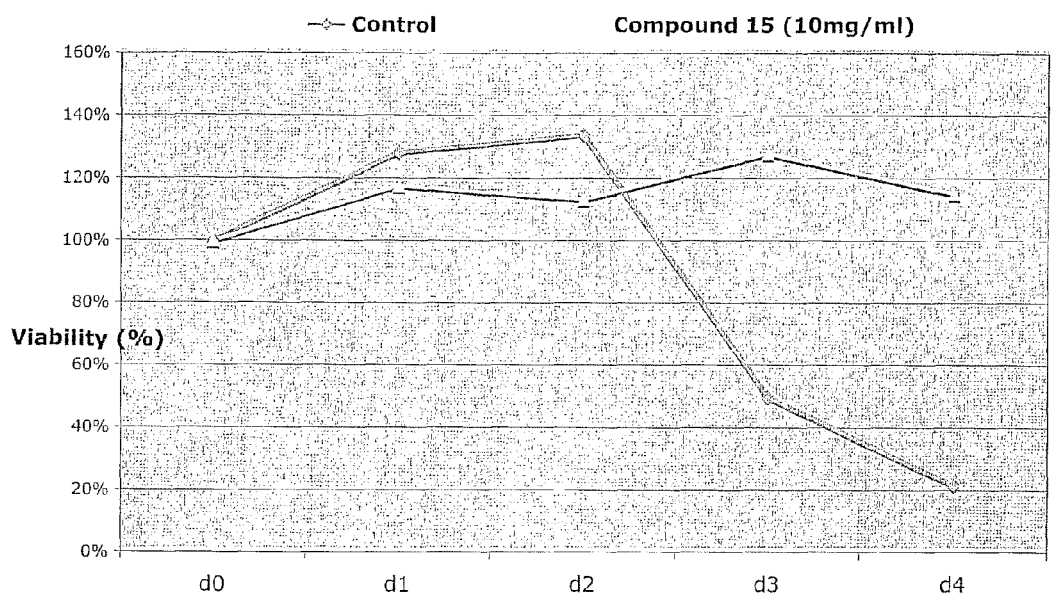
FIG. 53 is a representation of effects of 10 mg/ml of compound 15 on cell viability at 37° C. in low-serum media (Adherent Culture)

In this experiment, the aim was to study the efficacy of gem-difluoro glycoproteins under physiological conditions:

Compound 15 preserves approximately 100% of cells at 37° C. even after four days, whereas in the control the survival rate is 20%. This show a strong protective effect under physiological conditions (FIG. 53).

Figure 54:
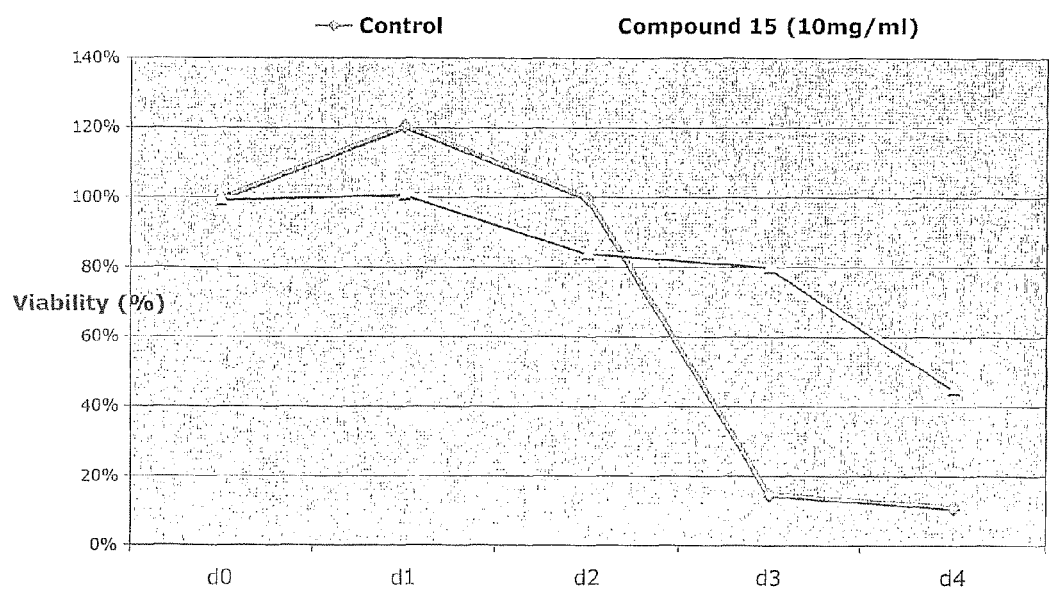
FIG. 54 is a representation of effects of 10 mg/ml of compound 15 on cell viability at 15° C. in low-serum media.

The monomer 15 also preserves cells (46% survival) at 15° C., whereas only 11% are found in the control after four days (FIG. 54).

Figure 55:
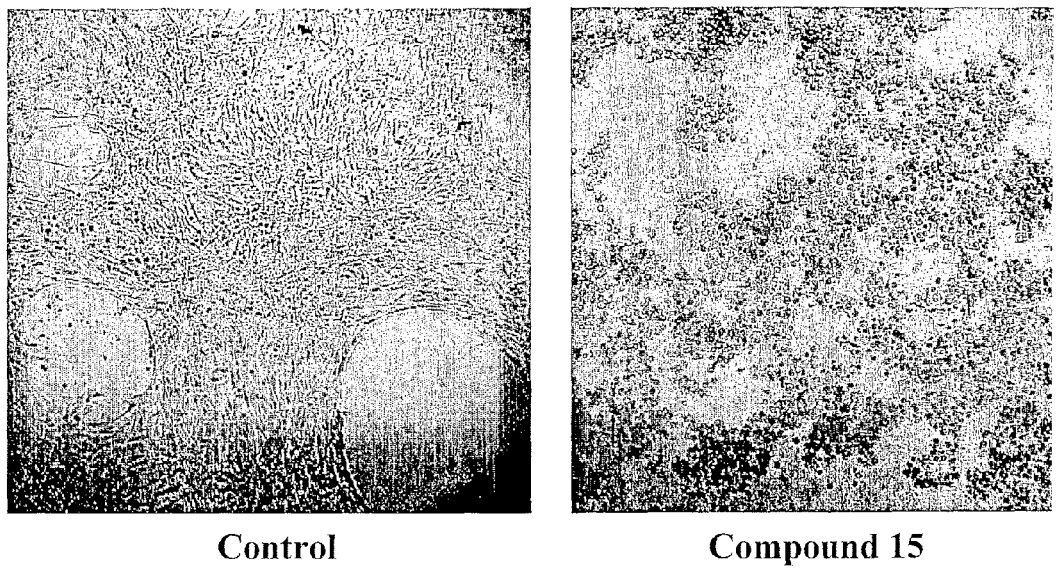
FIG. 55 is a representation of cells at Day 1.

The cells incubated with this compound preserve a spherical shape and maintain their integrity, whereas in the negative control the cells lose their structural morphology and become adherent (FIG. 55).

Preliminary Results on the Protection of Adult Primary Skin Fibroblasts By Compound 15

The preceding results have shown that the monomer 15 has a strong protective effect on embryonic skin fibroblasts over a varied temperature range. This test was extended to adult primary fibroblasts. In the following study, experiments were conducted at 15° C., 3° C., on adult fibroblasts, but also at 37° C. under $H_2O_2$ on embryonic fibroblasts.

Experimental Protocol

Culture Conditions:

For adult fibroblasts, a culture medium (rich in factors) is used,

For embryonic fibroblasts, a serum-free medium with 0.5 mM EDTA is used to prevent clustering. The cells are treated with 1 mM $H_2O_2$ to induce oxidizing stress. Samples are examined at 0, 1, 2, 3, 4 and 6 days for the experiments on adult fibroblasts, and at 2 and 10 hours on embryonic fibroblasts. The concentration of product 15 is 15 mg/mL.

Figure 56:
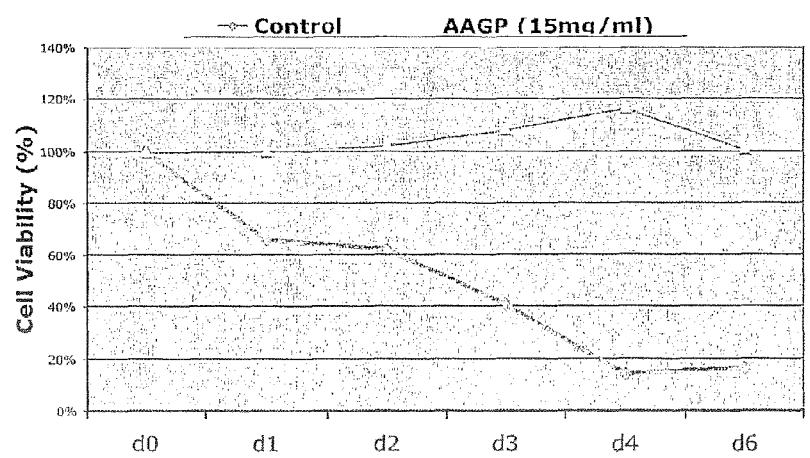
FIG. 56 is a representation of effects of 15 mg/ml of compound 15 on cell viability at 15° C. in culture media.
Figure 57:
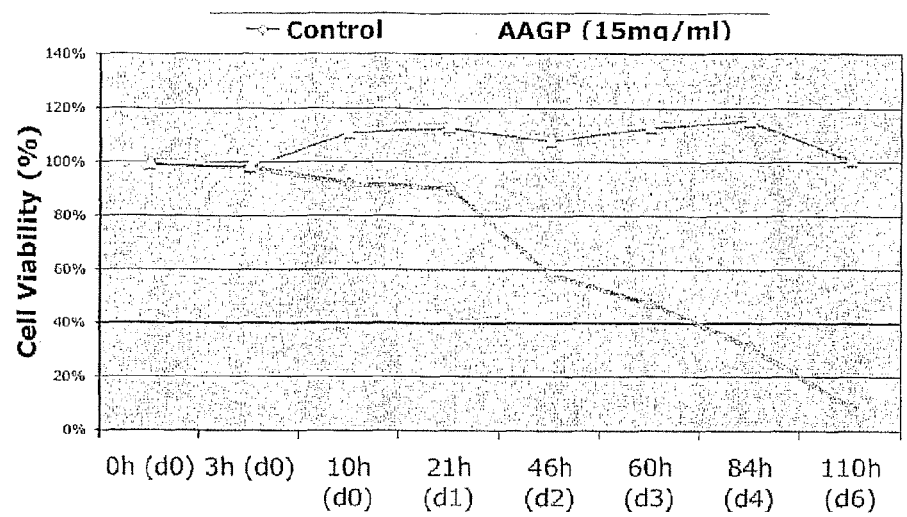
FIG. 57 is a representation of effects of 15 mg/ml of compound 15 on cell viability at 3° C. in culture media.

On the Adult Primary Fibroblasts:

At 15° C. (FIG. 56), compound 15 protects 100% of cells even after six days, whereas almost all the control cells are dead. At 3° C. (FIG. 57), 100% survival is also observed, and only 9% after six days in the control.

Figure 58:
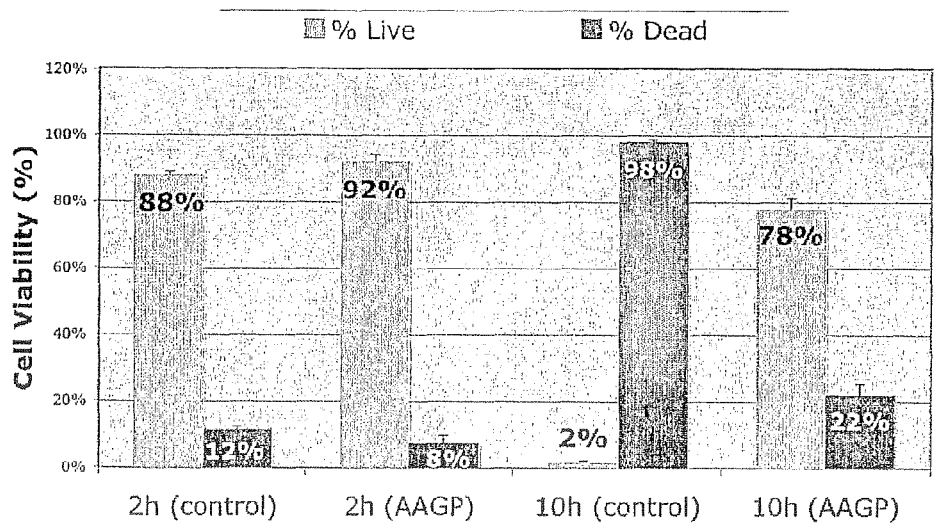
FIG. 58 is a representation of effects of $H_2O_2$ on cells treated with 15 mg/mL of compound 15 at 37° C.

On the Embryonic Fibroblasts:

The monomer 15 protects the cells with approximately 80% survival, compared with the control in which the cells are all dead after 10 hours (FIGS. 58 and 59). The difference is clearly seen between the cells treated with AAGP and the control (living cells shown in green, dead cells in red). Product 15 can therefore act as protective agent against oxidizing stress, a major problem in skin ageing and skin diseases.

and $R^1$, $R^2$, $R^3$ are independent groups in which two of $R^1$, $R^2$ and $R^3$ are selected from H, $CH_3$, $CH_2Ph$, $CH(CH_3)_2$, $CH_2CH(CH_3)_2$ or $CH(CH_3)CH_2CH_3$, and the remaining $R^1$, $R^2$, $R^3$ is

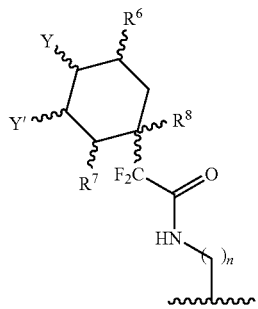

in which: n is an integer between 3 and 4,

---

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Residue may be modified by a Boc moiety at the
      N-terminus and may be modified with a Z moiety at the end of the
      side chain.
<220> FEATURE:
<221> NAME/KEY: misc_feature
<222> LOCATION: (6)..(6)
<223> OTHER INFORMATION: Residue may be modified by a OMe group.

<400> SEQUENCE: 1

Lys Ala Ala Lys Ala Ala
1               5
```

---

The invention claimed is:

1. Gem-difluorinated C-glycopeptide compound of general formula I:

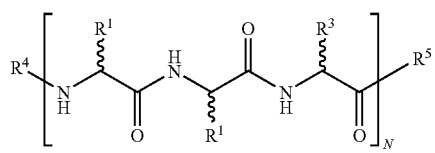

in which:

N is an integer between 1 and 5, $R^4$=H, $AA_1$, or $AA_1$-$AA_2$, $R^5$=OH, $AA_1$, or $AA_1$-$AA_2$, $AA_1$ and $AA_2$ independently represents amino acids with a non-polar side chain Y, Y' are independent groups in which Y, Y'=H, OR, $N_3$, NR'R", SR''', where R=H, benzyl, trimethylsilyl, tert-butyldimethylsilyl, tert-butyldiphenylsilyl, or acetate group, R', R" independently =H, alkyl, allyl, benzyl, tosylate group, C(=O)-alkyl, or C(=O)—Bn, R'''=H, alkyl, or acetate group, $R^6$ is H, $CH_3$, $CH_2OH$, $CH_2$-glycoside group, or $CH_2$-OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, and if $R^1$=$R^2$=H, $CH_3$, $CH_2Ph$, $CH(CH_3)_2$, $CH_2CH(CH_3)_2$, or $CH(CH_3)CH_2CH_3$ then $R^3=$

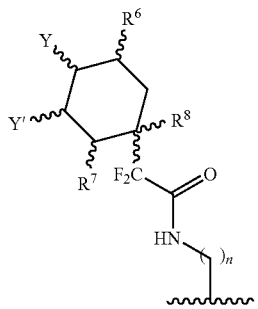

in which: n is an integer between 3 and 4,

Y, Y' are independent groups in which Y, Y'=H, OR, $N_3$, NR'R", SR''', where R=H, benzyl, trimethylsilyl, tert-butyldimethylsilyl, tert-butyldiphenylsilyl, or acetate group, R', R" independently =H, alkyl, allyl, benzyl, tosylate group, C(=O)-alkyl, or C(=O)—Bn, R'''=H, alkyl, acetate group, $R^6$ is H, $CH_3$, $CH_2OH$, $CH_2$-glycoside group, or $CH_2$-OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, if $R^1=R^3=$H, $CH_3$, $CH_2Ph$, $CH(CH_3)_2$, $CH_2CH(CH_3)_2$, or $CH(CH_3)CH_2CH_3$ then $R^2=$ in which: n is an integer between 3 and 4, Y, Y' are independent groups in which Y, Y'=H, OR, $N_3$, NR'R", SR''', or SR''', where R=H, benzyl, trimethylsilyl, tert-butyldimethylsilyl, tert-butyldiphenylsilyl, or acetate group, R', R" independently =H, alkyl, allyl, benzyl, tosylate group, C(=O)-alkyl, or C(=O)—Bn, R'''=H, alkyl, or acetate group, $R^6$ is H, $CH_3$, $CH_2OH$, $CH_2$-glycoside group, or $CH_2$-OGP group in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function, if $R^2=R^3=$H, $CH_3$, $CH(CH_3)_2$, $CH_2CH(CH_3)_2$, or $CH(CH_3)CH_2CH_3$ then $R^1=$ in which: n is an integer between 3 and 4, Y, Y' are independent groups in which Y, Y'=H, OR, $N_3$, NR'R", or SR''', where R=H, benzyl, trimethylsilyl, tert-butyldimethylsilyl, tert-butyldiphenylsilyl, or acetate group, R', R"=H, alkyl, allyl, benzyl, tosylate group, C(=O)-alkyl, or C(=O)—Bn, R'''=H, alkyl, or acetate group, $R^6$ is H, $CH_3$, $CH_2OH$, $CH_2$-glycoside group, or $CH_2$-OGP in which GP is a protector group selected from alkyl, benzyl, trimethylsilyl, tert-butyldimethylsilyl, tert-butyldiphenylsilyl, or acetate group, $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group, $R^8$ is a hydrogen atom H or a free or protected alcohol function.

2. A compound as in claim 1, characterized in that it comprises a compound of general formula II:

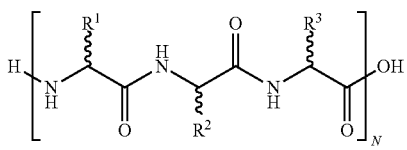

in which: N is an integer between 1 and 5, and $R^1$, $R^2$, $R^3$ are independent groups in which two of $R^1$, $R^2$ and $R^3$ are selected from H, or $CH_3$, and the remaining $R^1$, $R^2$ and $R^3$ is

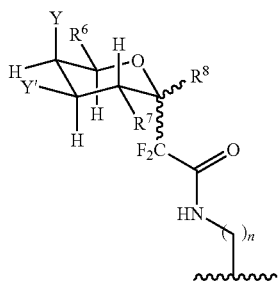

in which : n is an integer between 3 and 4,
Y, Y' are independent groups
  in which Y, Y'=H, OR, $N_3$, NR'R", or SR''',
    where R=H, benzyl, trimethylsilyl, tert-butyldimethylsilyl, tert-butyldiphenylsilyl, or acetate group,
    R', R" independently =H, alkyl, allyl, benzyl, tosylate group, C(=O)-alkyl, or C(=O)—Bn,
    R'''=H, alkyl, or acetate group,
  $R^6$ is selected from H, $CH_3$, $CH_2OH$, $CH_2$-OGP in which GP is a protector group selected from alkyl, benzyl, trimethylsilyl, tert-butyldimethylsilyl, tert-butyldiphenylsilyl, or acetate group,
  $R^2$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl, or acetate group,
  $R^8$ is a hydrogen atom H or a free or protected alcohol function,
and
if $R^1=R^2$=H or $CH_3$,
then $R^3$=

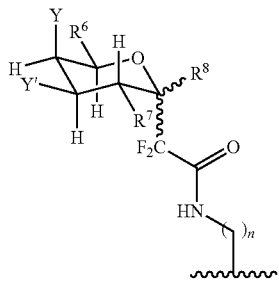

in which : n is an integer between 3 and 4,
Y, Y' are independent groups
  in which Y, Y'=H, OR, $N_3$, NR'R", or SR''',
    where R =H, benzyl, trimethylsilyl, tert-butyldimethylsilyl, tert-butyldiphenylsilyl, or acetate group, R', R" independently =H, alkyl, allyl, benzyl, tosylate group, C(=O)-alkyl, or C(=O)—Bn,
    R'''=H, alkyl, or acetate group,
  $R^6$ is selected from H, $CH_2$, $CH_2OH$, $CH_2$-OGP in which GP is a protector group selected from alkyl, benzyl, trimethylsilyl, tert-butyldimethylsilyl, tert-butyldiphenylsilyl, or acetate group,
  $R^7$=OH, OGP', $NH_2$, $N_3$, NHGP', NGP'GP" in which GP' and GP" are independently selected from alkyl, benzyl, trimethylsilyl, tert-butyldimethylsilyl, tert-butyldiphenylsilyl, or acetate group,
  $R^8$ is a hydrogen atom H or a free or protected alcohol function,
if $R^1=R^3$=H or $CH_3$, then $R^2$=

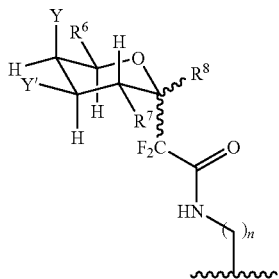

in which: n is an integer between 3 and 4,
Y, Y' are independent groups
  in which Y, Y'=H, OR, $N_3$, NR'R", SR''', where R =H, benzyl, trimethylsilyl, tert-butyldimethylsilyl, tert-butyldiphenylsilyl, or acetate group,
  R', R" independently =H, alkyl, allyl, Bn, tosylate, C(=O)-alkyl, or C(=O)—Bn,
  R'''=H, alkyl, or acetate group,
  $R^6$ is selected from H, $CH_2$, $CH_2OH$, or $CH_2$-OGP in which GP is a protector group selected from alkyl, benzyl, trimethylsilyl, tert-butyldimethylsilyl, tert-butyldiphenylsilyl, or acetate group,
  $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group,
  $R^8$ is a hydrogen atom H or a free or protected alcohol function,
if $R^2=R^3$=H or $CH_3$,
then $R^1$=

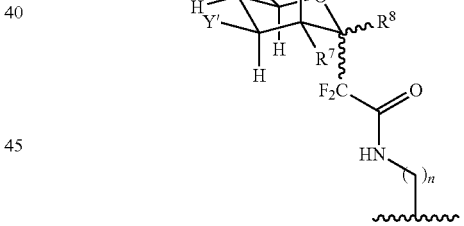

in which: n is an integer between 3 and 4,
Y, Y' are independent groups
  in which Y, Y'=H, OR, $N_3$, NR'R", or SR''',
    where R=H, benzyl, trimethylsilyl, tert-butyldimethylsilyl, tert-butyldiphenylsilyl, or acetate group,
    R', R" independently =H, alkyl, allyl, benzyl, tosylate group, C(=O)-alkyl, or C(=O)—Bn,
    R'''=H, alkyl, or acetate group,
  $R^6$ is selected from H, $CH_3$, $CH_2OH$, or $CH_2$-OGP in which GP is a protector group selected from alkyl, benzyl, trimethylsilyl , tert-butyldimethylsilyl, tert-butyldiphenylsilyl, or acetate group,
  $R^7$=OH, OGP', $NH_2$, $N_3$, NHGP', or NGP'GP" in which GP' and GP" are independently selected from alkyl, benzyl, trimethylsilyl, tert-butyldimethylsilyl, tert-butyldiphenylsilyl, or acetate group,
  $R^8$ is a hydrogen atom or a free or protected alcohol function.

3. A compound which is a pharmaceutically acceptable base, addition salt with an acid, hydrate or solvate of the compound of claim 1.

4. A method for preparing a gem-difluorinated compound according to claim 1, comprising a reaction between a compound with general formula IV:

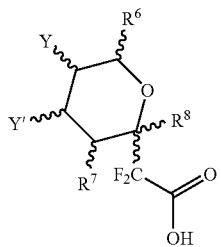

wherein Y, Y' are independent groups
in which Y, Y'=H, OR, $N_3$, NR'R'', or SR''',
where R=H, benzyl, trimethylsilyl, tert-butyldimethylsilyl, tert-butyldiphenylsilyl, or acetate group,
R', R'' independently =H, alkyl, allyl, Bn, tosylate, C(=O)-alkyl, or C(=O)—Bn,
R'''=H, alkyl, or acetate group,
$R^6$ is H, $CH_2$, $CH_2OH$, $CH_2$-glycoside group or $CH_2$-OGP in which GP is a protector group selected from alkyl, benzyl, trimethylsilyl, tert-butyldimethylsilyl, tert-butyldiphenylsilyl, or acetate,
$R^7$=OH, OGP', $NH_2$, $N_3$, NHGP', or NGP'GP'' in which GP' and GP'' are independently alkyl, benzyl, trimethylsilyl, tert-butyldimethylsilyl, tert-butyldiphenylsilyl, or acetate group,
$R^8$ is a hydrogen atom H or a free or protected alcohol function,
and a compound of general formula V :

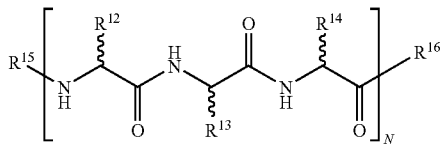

wherein N is an integer between 1 and 5,
$R^{15}$=H, $AA_1$, $AA_1$-$AA_2$ or a protective group,
$R^{16}$=OH, $AA_1$, $AA_1$-$AA_2$ or a protective group,
$AA_1$ and $AA_2$ are independent and represent amino acids, and
$R^{12}$, $R^{13}$, $R^{14}$ are independent groups in which two of $R^{12}$, $R^{13}$ and $R^{14}$ are selected from H, $CH_3$, $CH_2Ph$, $CH(CH_3)_2$, $CH_2CH(CH_3)_2$ or $CH(CH_3)$ $CH_2CH_3$, and the remaining $R^{12}$, $R^{13}$ and $R^{14}$ is $(CH_2)_n$—$NH_2$ where n is an integer between 3 and 4,
and
if $R^{12}$=$R^{13}$=H, $CH_3$, $CH_2Ph$, $CH(CH_3)_2$, $CH_2CH(CH_3)_2$, or $CH(CH_3)CH_2CH_3$
then $R^{14}$ is —$(CH_2)_n$—$NH_2$ where n is an integer between 3 and 4,
if $R^{12}$=$R^{14}$=H, $CH_3$, $CH_2Ph$, $CH(CH_3)_2$, $CH_2CH(CH_3)_2$, or $CH(CH_3)CH_2CH_3$
then $R^{13}$ is —$(CH_2)_n$—$NH_2$ where n is an integer between 3 and 4,
if $R^{13}$=$R^{14}$=H, $CH_3$, $CH_2Ph$, $CH(CH_3)_2$, $CH_2CH(CH_3)_2$, or $CH(CH_3)CH_2CH_3$
then $R^{12}$ is —$(CH_2)_n$—$NH_2$ where n is an integer between 3 and 4.

5. A composition which contains at least one compound as claimed in claim 1 or one of its salts obtained by addition to a pharmaceutically acceptable mineral or organic acid.

6. A composition as in claim 5, containing pharmaceutically acceptable, inert, non-toxic excipients.

7. The composition of claim 5, which can be used in cryosurgery.

8. The composition of claim 5, which can be used for the preservation of biological materials.

9. The composition of claim 5, which can be used for the preservation of kidney cells.

10. The composition of claim 5, which can be used for the preservation of erythrocytes.

11. The composition of claim 5, which can be used for the preservation of blood platelets.

12. The composition of claim 5, which can be used for the preservation of heart cells.

13. The composition of claim 5, which can be used for the preservation of fibroblasts.

14. The composition of claim 5, which can be used in cosmetology.

15. A cosmetic treatment process to protect against oxidizing stress, comprising applying a composition comprising a compound as claimed in claim 1 as a cosmetic.

16. The composition of claim 6, wherein the pharmaceutically acceptable, inert, non-toxic excipients are selected from distilled water, glucose, starch, lactose, talc, vegetable oils, ethylene glycol and/or preserving agents.

* * * * *